(12) United States Patent
Pantoja et al.

(10) Patent No.: US 10,309,927 B2
(45) Date of Patent: Jun. 4, 2019

(54) METHODS OF CONDUCTING BIOCHEMICAL REACTIONS WHILE REDUCING REACTIVE MOLECULAR SPECIES DURING ELECTROWETTING

(71) Applicant: Illumina, Inc., San Diego, CA (US)

(72) Inventors: Rigo Pantoja, San Diego, CA (US); Rachel M. Schowalter, San Diego, CA (US); Jimmy Perrott, San Diego, CA (US); Cyril Delattre, San Diego, CA (US); Allen E. Eckhardt, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 507 days.

(21) Appl. No.: 15/093,529

(22) Filed: Apr. 7, 2016

(65) Prior Publication Data

US 2016/0299101 A1  Oct. 13, 2016

Related U.S. Application Data

(60) Provisional application No. 62/145,891, filed on Apr. 10, 2015, provisional application No. 62/200,188, filed on Aug. 3, 2015.

(51) Int. Cl.
*G01N 27/447* (2006.01)
*C12Q 1/6869* (2018.01)
(Continued)

(52) U.S. Cl.
CPC .... *G01N 27/44791* (2013.01); *B01L 3/50273* (2013.01); *B01L 3/502715* (2013.01);
(Continued)

(58) Field of Classification Search
CPC ....... G01N 27/44791; G01N 27/44743; C12Q 1/6844; C12Q 1/686; C12Q 1/6869;
(Continued)

(56) References Cited

U.S. PATENT DOCUMENTS 5,874,046 A    2/1999   Megerle
2008/0053205 A1  3/2008   Pollack
(Continued)

FOREIGN PATENT DOCUMENTS

JP   2004117371 A    4/2004
WO   WO 98/13675 A1  4/1998
(Continued)

OTHER PUBLICATIONS

O. S. Ksenzhek, et al. "Electrochemical properties of some redox indicators", Bioelectrochemistry and Bioenergetics, 4(4): p. 346-357 (Year: 1977).*
(Continued)

*Primary Examiner* — J. Christopher Ball
(74) *Attorney, Agent, or Firm* — Illumina, Inc.

(57) ABSTRACT

Some embodiments disclosed herein provide methods of reducing reactive molecular species in a reaction carried out in a digital fluidics device having one or more electrodes by using a reaction mixture comprising an electron acceptor additive. In some embodiments, the presence of the electron acceptor additive reduces the presence of reactive molecular species in the reaction mixture. In some embodiments, the presence of the electron acceptor additive reduces the formation of gas bubbles in the digital fluidic device. Therefore, in preferred embodiments, the electron acceptor additive does not form a gas when reduced.

27 Claims, 29 Drawing Sheets

(51) Int. Cl.
  *B01L 3/00* (2006.01)
  *C12Q 1/686* (2018.01)
  *C12Q 1/6844* (2018.01)
(52) U.S. Cl.
  CPC .......... *C12Q 1/686* (2013.01); *C12Q 1/6844* (2013.01); *C12Q 1/6869* (2013.01); *G01N 27/44743* (2013.01); *B01L 2400/0421* (2013.01); *B01L 2400/0427* (2013.01)
(58) Field of Classification Search
  CPC .......... B01L 3/50273; B01L 3/502715; B01L 2400/0427; B01L 2400/0421
  See application file for complete search history.

(56) References Cited

U.S. PATENT DOCUMENTS

2013/0130936 A1\* 5/2013 Eckhardt .................. C12Q 1/25
                                                                       506/12
2014/0178862 A1 6/2014 Su

FOREIGN PATENT DOCUMENTS

WO     WO 2004/057685 A2     7/2004
WO     WO-2009021173 A1 \*    2/2009     ........ B01L 3/502792

OTHER PUBLICATIONS

"Silicon Fluids: Stable, Inert Media", 31 pages, obtained from https://www.gelest.com/wp-content/uploads/Goods-PDF-brochures-inert_silicones_2013.pdf (Year: 2012).\*
International Search Report and Written Opinion for PCT/US2016/026459 dated Jun. 17, 2016.

\* cited by examiner

Table 2. $R_s/R_c$ Values, Expected Sensitivity Factor $L$, and Dc Conductivity for Several Buffers, Adjusted to Specific pH Values with Different Acids or Bases

| buffer | titrated with | pH | $R_s/R_c$ | sensitivity factor $L$ | conductivity (mS/cm) |
|---|---|---|---|---|---|
| BIS—TRIS propane | HCl | 6.8 | 1.70 ± 0.04 | 0.27 | 19.34 |
|  | PIPES |  | 0.84 ± 0.03 | 0.37 | 8.75 |
| TRIS base | HCl | 8.0 | 0.88 ± 0.03 | 0.36 | 9.60 |
|  | TES |  | 0.60 ± 0.03 | 0.43 | 5.71 |
| sodium phosphate |  | 7.0 | 1.63 ± 0.04 | 0.28 | 17.34 |
| MOPS | BIS—TRIS propane | 7.0 | 0.22 ± 0.02 | 0.61 | 2.40 |
| bicine | NaOH | 8.0 | 0.28 ± 0.02 | 0.58 | 2.61 |
|  | TRIS base |  | 0.29 ± 0.02 | 0.56 | 2.50 |
| HEPES | BIS—TRIS propane | 7.0 | 0.31 ± 0.02 | 0.55 | 1.30 |
|  | NaOH |  | 0.41 ± 0.03 | 0.50 | 2.44 |

Figure 7A

Table 1. Buffer properties

| Buffer | Concentration | pKa[a] | pI | pH[b] | Conductivity (µS/cm) |
|---|---|---|---|---|---|
| glycine | 50 mM | 2.34, 9.60 | 5.97 | 6.01 | 2.5 ± 0.2 |
| glycine | 250 mM | 2.34, 9.60 | 5.97 | 6.11 | 7.8 ± 0.5 |
| β-alanine | 50 mM | 3.60, 10.19 | 6.90 | 6.71 | 3.6 ± 0.6 |
| GABA | 50 mM | 4.03, 10.56 | 7.30 | 6.76 | 5.6 ± 0.6 |
| cysteine | 50 mM | 1.71, 8.33, 10.78 | 5.02 | 5.08 | 9.0 ± 0.9 |
| cysteine | 250 mM | 1.71, 8.33, 10.78 | 5.02 | nd[d] | 21.8 ± 4.4 |
| 3(τ)-methylhistidine | 50 mM | 1.70, 5.87, 9.16[c] | 7.52 | 7.44 | 39.4 ± 0.4 |
| D-histidine | 50 mM | 1.78, 5.97, 8.97 | 7.47 | 7.70 | 57.1 ± 0.3 |
| L-histidine | 50 mM | 1.78, 5.97, 8.97 | 7.47 | 7.65 | 60.1 ± 0.1 |
| carnosine | 50 mM | 2.64, 6.83, 9.51 | 8.17 | 8.07 | 74.5 ± 5.5 |
| 1(π)-methylhistidine | 50 mM | 1.64, 6.46, 8.61[c] | 7.54 | 7.59 | 117 ± 2.8 |
| pyridine | 50 mM | 5.19 | — | 8.17 | 5.0 ± 0.8 |
| imidazole | 50 mM | 6.99 | — | 9.08 | 17.6 ± 1.6 |
| collidine | 50 mM | 6.69 | — | 9.85 | 33.0 ± 0.9 |

[a]Values obtained from Budavari, S. (1989) The Merck Index, 11th Ed., Merck & Co., Inc., Rahway, NJ, unless otherwise noted.
[b]pH of buffer solution measured in water at room temperature.
[c]Remelli, M., Munerato, C. and Pulidori, F. (1994) J. Chem. Soc. Dalton Trans., 2049–2056.
[d]nd, not determined.

Table 1. $R_x/R_c$ Values, Expected Sensitivity Factor $L$, and Dc Conductivity of Several Different Salts, All at 200 mM Concentration

| buffer | $R_x/R_c$ | sensitivity factor $L$ | conductivity (mS/cm) |
|---|---|---|---|
| pentasodium tripolyphosphate | 2.71 ± 0.04 | 0.22 | 31.3 |
| potassium chloride | 1.93 ± 0.04 | 0.26 | 23.3 |
| disodium phosphate (Na$_2$HPO$_4$) | 1.89 ± 0.04 | 0.28 | 22.0 |
| sodium pyrophosphate | 1.70 ± 0.04 | 0.27 | 20.2 |
| sodium chloride | 1.64 ± 0.04 | 0.28 | 18.1 |
| PIPES | 1.33 ± 0.04 | 0.30 | 14.8 |
| β-glycerophosphate | 1.31 ± 0.04 | 0.30 | 14.9 |
| potassium phosphate (KH$_2$PO$_4$) | 1.25 ± 0.04 | 0.31 | 14.1 |
| TRIS HCl | 1.24 ± 0.04 | 0.31 | 14.1 |
| BIS–TRIS HCl | 1.12 ± 0.03 | 0.33 | 13.62 |
| sodium acetate | 1.11 ± 0.03 | 0.33 | 12.2 |
| sodium phosphate (NaH$_2$PO$_4$) | 0.95 ± 0.03 | 0.35 | 11.0 |
| sodium TAPS | 0.90 ± 0.03 | 0.36 | 9.55 |
| sodium MES | 0.88 ± 0.03 | 0.36 | 10.18 |
| sodium MOPS | 0.88 ± 0.03 | 0.36 | 9.86 |
| sodium TES | 0.84 ± 0.03 | 0.37 | 9.41 |
| sodium HEPES | 0.84 ± 0.03 | 0.37 | 9.25 |
| tetrabutylammonium dihydrogen phosphate | 0.69 ± 0.03 | 0.40 | 9.08 |
| HEPES | 0.22 ± 0.02 | 0.62 | 0.86 |
| TAPS | 0.14 ± 0.02 | 0.70 | 0.29 |
| CAPS | 0.14 ± 0.02 | 0.70 | 0.7 |
| TES | 0.12 ± 0.02 | 0.73 | 0.25 |
| MOPS | 0.10 ± 0.02 | 0.76 | 0.04 |
| CHES | 0.08 ± 0.02 | 0.79 | 0.06 |
| MES | 0.08 ± 0.02 | 0.88 | 0.15 |
| betaine | 0.05 ± 0.02 | 0.86 | 0.031 |
| BIS–TRIS propane | 0.05 ± 0.02 | 0.88 | 0.022 |
| TRIS base | 0.03 ± 0.02 | 0.91 | 0.1 |
| BIS–TRIS | 0.02 ± 0.02 | 0.93 | 0.0230 |
| deionized-distilled H$_2$O | 0.01 ± 0.02 | 0.98 | 0.0023 |

Figure 14B

METHODS OF CONDUCTING BIOCHEMICAL REACTIONS WHILE REDUCING REACTIVE MOLECULAR SPECIES DURING ELECTROWETTING

RELATED APPLICATIONS

This application is based upon and claims the benefit under 35 U.S.C. § 119(e) of U.S. Provisional Patent Application Ser. No. 62/200,188, filed Aug. 3, 2015, and U.S. Provisional Patent Application Ser. No. 62/145,891, filed Apr. 10, 2015, the contents of which are incorporated herein by reference in their entireties for all purposes.

BACKGROUND

A droplet actuator is an example of digital microfluidics technology. A droplet actuator typically includes one or more substrates configured to form a surface or gap for conducting droplet operations. The one or more substrates establish a droplet operations surface or gap for conducting droplet operations and may also include electrodes arranged to conduct the droplet operations via electrowetting. The droplet operations substrate or the gap between the substrates may be coated or filled with a filler fluid that is immiscible with the liquid that forms the droplets. Digital microfluidics devices have been used to conduct a variety of molecular protocols such as amplification of nucleic acids (e.g., quantitative polymerase chain reaction (qPCR)) and nucleic acid sequencing. A digital microfluidic protocol for performing a biochemical reaction typically includes the electrowetting-induced transport and mixing of an aqueous sample and reagent droplets in an immiscible fluid, such as oil, in a droplet actuator.

SUMMARY

Some embodiments disclosed herein provide methods of reducing reactive molecular species in a reaction carried out in a digital fluidics device having one or more electrodes, the method comprising: providing a reaction mixture comprising one or more reagents and an electron acceptor additive; forming a reaction droplet from the reaction mixture; and activating the one or more electrodes to conduct a reaction, wherein the presence of the electron acceptor additive reduces the presence of reactive molecular species in the reaction mixture. In some embodiments, the electron acceptor additive comprises a redox potential lower than 830 mV. In some embodiments, the electron acceptor additive comprises phenazine ethosulfate (PES), phenazine methosulfate (PMS), or a combination thereof. In some embodiments, the electron acceptor additive prevents the electrolysis of water. In some embodiments, the electron acceptor additive is not a reactant in the reaction. In some embodiments, the electron acceptor additive does not form a gas when reduced. In some embodiments, the reaction mixture comprises low conductivity in a range of about 2.5±0.2 µS/cm to about 5±0.8 µS/cm. In some embodiments, the reaction mixture comprises low pH of about pH 2.0 to pH 7.0. In some embodiments, activating the one or more electrodes comprises selecting droplet electrowetting parameters that result in a reduction in the formation of reactive molecular species. In some embodiments, the droplet electrowetting parameters comprise one or more of droplet size, transport rate, and electrode exposure. In some embodiments, droplet size is less than 8 digital units. In some embodiments, the reaction is a sequencing-by-synthesis (SBS) reaction. In some embodiments, the reaction is a nucleic acid amplification reaction. In some embodiments, the reactive molecular species comprise reactive oxygen species (ROS) or hypochlorite. In some embodiments, the reduction in the formation of reactive molecular species reduces the formation of bubbles. In some embodiments, the methods further comprise surrounding the reaction droplet with an immiscible fluid. In some embodiments, the immiscible fluid comprises a modified polysiloxane polymer. In some embodiments, the modified polysiloxane polymer in the immiscible fluid has the following formula:

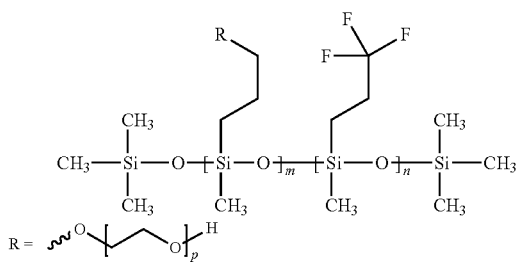

wherein PEG length=200 g/mol (5 EO units), m=1-300, n=1-300, and p=1-50. In some embodiments, the modified polysiloxane polymer in the immiscible fluid comprises POLY(3,3,3-TRIFLUOROPROPYLMETHYLSILOXANE), HYDROXYPROPYLENEOXYPROPYL) METHYL SILOXANE-DIMETHYL SILOXANE COPOLYMER, 1,3-BIS(TRIDECAFLUORO-1,1,2,2-TETRAHYDROOCTYL) TETRAMETHYLDISILOXANE, or a combination thereof. In some embodiments, the modified polysiloxane polymer has the following formula:

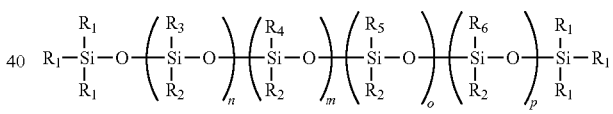

wherein each $R_1$ is, independently, hydrogen, $C_{1-8}$ alkyl, $C_{6-30}$ aryl, or $C_{1-15}$ alkyl-substituted $C_{6-30}$ aryl, and specific $R_1$ groups include hydrogen, methyl, ethyl, propyl, isopropyl, butyl, sec-butyl, t-butyl, isobutyl, isoamyl, and t-amyl, with methyl being particularly preferred; $R_2$ is, independently, $R_1$, $R_3$, $R_4$, $R_5$, or $R_6$; $R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination; $R_4$ is, independently, a polyalkylene glycol moiety, where the alkylene groups are, independently, $C_{2-4}$, and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof; $R_5$ is, independently, a dye selected from the group consisting of erioglaucine, Nile blue, methylene blue, methyl viologen, methyl brilliant green, popop brilliant green, caffeine dye, proton sponge dye, and DDT black, linked to the polymer at any position; $R_6$ is an electron acceptor; m is a whole number from 0 to about 300, n is a whole number from 0 to about 300, o is a whole number from 0 to about 300, and p is a whole number from 0 to about 300, wherein at least one of m, n, o, and p is not 0.

Some embodiments disclosed herein provide methods of reducing reactive molecular species in a reaction carried out in a digital fluidics device, the method comprising: providing biochemical reagents in a buffer in the presence of an activated electrode to form a reaction mixture, wherein the buffer comprises an electron acceptor additive; forming a reaction droplet from the reaction mixture; and conducting a reaction in the reaction droplet, wherein the presence of the electron acceptor additive reduces the presence of reactive molecular species in the reaction mixture. In some embodiments, the electron acceptor additive comprises a redox potential lower than 830 mV. In some embodiments, the electron acceptor additive comprises phenazine ethosulfate (PES), phenazine methosulfate (PMS), or a combination thereof. In some embodiments, the electron acceptor additive prevents the electrolysis of water. In some embodiments, the electron acceptor additive is not a reactant in the reaction. In some embodiments, the electron acceptor additive does not form a gas when reduced.

Some embodiments disclosed herein provide methods of reducing reactive molecular species in a reaction carried out in a digital fluidics device having one or more electrodes, the method comprising: providing a reaction droplet; surrounding the reaction droplet with an immiscible fluid comprising a modified polysiloxane polymer; and activating the one or more electrodes to conduct a reaction, wherein the presence of the electron acceptor additive reduces the presence of reactive molecular species in the reaction mixture. In some embodiments, the modified polysiloxane polymer in the immiscible fluid has the following formula:

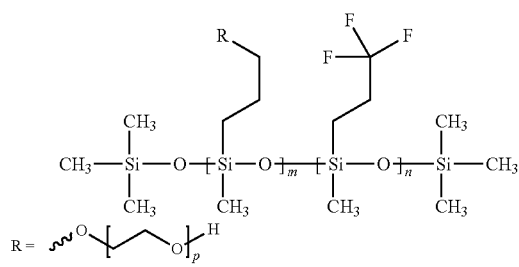

wherein PEG length=200 g/mol (5 EO units), m=1-300, n=1-300, and p=1-50. In some embodiments, the modified polysiloxane polymer in the immiscible fluid comprises POLY(3,3,3-TRIFLUOROPROPYLMETHYLSILOXANE), HYDROXYPROPYLENEOXYPROPYL) METHYL SILOXANE-DIMETHYL SILOXANE COPOLYMER, 1,3-BIS(TRIDECAFLUORO-1,1,2,2-TETRAHYDROOCTYL) TETRAMETHYLDISILOXANE, or a combination thereof. In some embodiments, the modified polysiloxane polymer has the following formula:

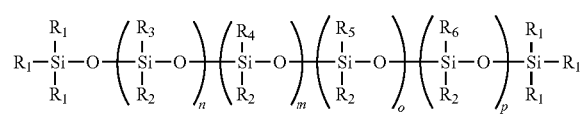

wherein each $R_1$ is, independently, hydrogen, $C_{1-8}$ alkyl, $C_{6-30}$ aryl, or $C_{1-15}$ alkyl-substituted $C_{6-30}$ aryl, and specific $R_1$ groups include hydrogen, methyl, ethyl, propyl, isopropyl, butyl, sec-butyl, t-butyl, isobutyl, isoamyl, and t-amyl, with methyl being particularly preferred; $R_2$ is, independently, $R_1$, $R_3$, $R_4$, $R_5$, or $R_6$; $R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination; $R_4$ is, independently, a polyalkylene glycol moiety, where the alkylene groups are, independently, $C_{2-4}$, and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof; $R_5$ is, independently, a dye selected from the group consisting of erioglaucine, Nile blue, methylene blue, methyl viologen, methyl brilliant green, popop brilliant green, caffeine dye, proton sponge dye, and DDT black, linked to the polymer at any position; $R_6$ is an electron acceptor; m is a whole number from 0 to about 300, n is a whole number from 0 to about 300, o is a whole number from 0 to about 300, and p is a whole number from 0 to about 300, wherein at least one of m, n, o, and p is not 0.

Some embodiments disclosed herein provide systems for conducting a reaction in the presence of an activated electrode while reducing the formation of reactive molecular species, the system comprising: a fluidics cartridge comprising an electrowetting array having a plurality of electrodes; a reaction droplet comprising a reaction mixture; an immiscible fluid surrounding the reaction droplet; and an electron acceptor additive in the reaction mixture. In some embodiments, the electron acceptor additive comprises a redox potential lower than 830 mV. In some embodiments, the electron acceptor additive comprises phenazine ethosulfate (PES), phenazine methosulfate (PMS), or a combination thereof. In some embodiments, the electron acceptor additive prevents the electrolysis of water. In some embodiments, the electron acceptor additive is not a reactant in the chemical reaction. In some embodiments, the electron acceptor additive does not form a gas when reduced. In some embodiments, the immiscible fluid comprises a modified polysiloxane polymer. In some embodiments, the modified polysiloxane polymer in the immiscible fluid has the following formula:

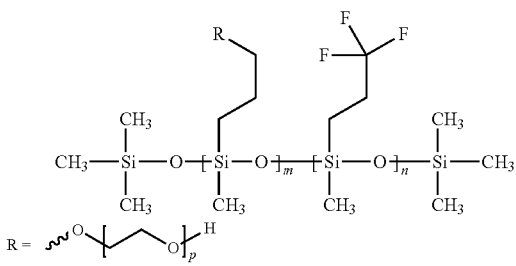

wherein PEG length=200 g/mol (5 EO units), m=1-300, n=1-300, and p=1-50. In some embodiments, the modified polysiloxane polymer in the immiscible fluid comprises POLY(3,3,3-TRIFLUOROPROPYLMETHYLSILOXANE), HYDROXYPROPYLENEOXYPROPYL)METHYLSILOXANE-DIMETHYLSILOXANE COPOLYMER, 1,3-BIS(TRIDECAFLUORO-1,1,2,2-TETRAHYDROOCTYL) TETRAMETHYLDISILOXANE, or a combination thereof. In some embodiments, the modified polysiloxane polymer has the following formula:

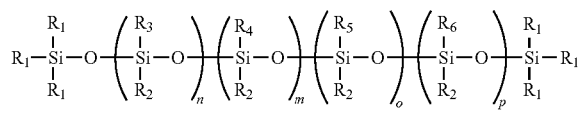

wherein each $R_1$ is, independently, hydrogen, $C_{1-8}$ alkyl, $C_{6-30}$ aryl, or $C_{1-15}$ alkyl-substituted $C_{6-30}$ aryl, and specific $R_1$ groups include hydrogen, methyl, ethyl, propyl, isopropyl, butyl, sec-butyl, t-butyl, isobutyl, isoamyl, and t-amyl, with methyl being particularly preferred; $R_2$ is, independently, $R_1$, $R_3$, $R_4$, $R_5$, or $R_6$; $R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination; $R_4$ is, independently, a polyalkylene glycol moiety, where the alkylene groups are, independently, $C_{2-4}$, and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof; $R_5$ is, independently, a dye selected from the group consisting of erioglaucine, Nile blue, methylene blue, methyl viologen, methyl brilliant green, popop brilliant green, caffeine dye, proton sponge dye, and DDT black, linked to the polymer at any position; $R_6$ is an electron acceptor; m is a whole number from 0 to about 300, n is a whole number from 0 to about 300, o is a whole number from 0 to about 300, and p is a whole number from 0 to about 300, wherein at least one of m, n, o, and p is not 0. In some embodiments, the fluidics cartridge comprises a substrate having a Cytop coating. In some embodiments, the Cytop coating has a thickness of greater than about 1,000 nm.

Some embodiments disclosed herein provide kits for conducting a reaction in the presence of an activated electrode while reducing the formation of reactive molecular species comprising a compartment comprising a reagent having an electron acceptor additive, wherein conducting a reaction in a reaction droplet comprising the reagent in the presence of an activated electrode results in reduced interference by reactive molecular species.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A and 7B show tables of different buffers and their conductivity that may be used in a "bubble free" formulation (BFF) for aqueous droplets;

FIGS. 14A and 14B show tables of potential salt solutions that may be used in the formulation of reaction buffers suitable for use in digital microfluidic applications, e.g., biochemical reactions performed on a droplet actuator;

DETAILED DESCRIPTION

Overview

Figure 1:
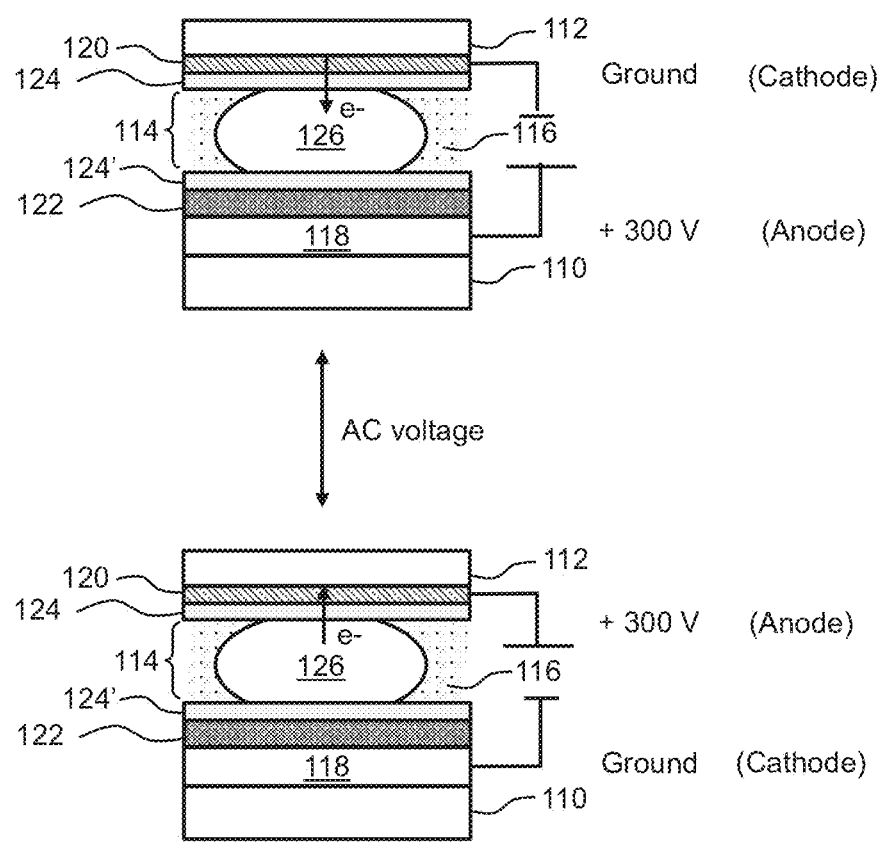
FIG. 1 is a schematic illustration that shows a side view of a portion of a droplet actuator and the problem of leakage current in a droplet actuator.

This disclosure relates to systems and methods of conducting a biochemical reaction in the presence of an electrode while reducing reactive molecular species that may become present in the reaction. In one embodiment, the reactive molecular species may be a reactive oxygen species (ROS) and/or hypochlorite (HOCl). The systems are typically digital microfluidics devices and the methods may use electrowetting to move the sample within the digital microfluidics devices. Within such an electrowetting device, an aqueous sample of reagent droplets are placed within immiscible fluids, such as oil, in the microfluidics cartridge. The microfluidics cartridge could be a droplet actuator. Embodiments of the invention generally involve combining the reactants necessary to form a reaction droplet and transporting and/or incubating the droplet within certain reaction zones of a droplet actuator. Embodiments relate to the discovery that reactive molecular species may be generated during electrowetting which may cause physical damage to device electrodes and dielectrics. These reactive molecular species may also damage biochemical reaction components, such as nucleic acids (e.g., DNA), enzymes, and reagents that are placed within the digital microfluidics device. Accordingly, embodiments relate to compositions and methods that reduce or eliminate these reactive molecular species in order to improve the operation and reliability of a fluidics device.

In one embodiment, an electron acceptor additive is used during operation of an electrowetting device to reduce the presence of reactive molecular species in the reaction mixture. The electron acceptor additive may comprise phenazine ethosulfate (PES), phenazine methosulfate (PMS), or a combination thereof. In some embodiments, the electron acceptor additive has a redox potential lower than 830 mV. In addition, the immiscible fluid used in the digital fluidics device may include an electron acceptor additive. Other embodiments that reduce the presence of reactive molecular species are discussed in more detail below.

Definitions

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the following terms have the meanings indicated.

As used herein, an electron acceptor is a chemical entity that accepts electrons transferred to it from another compound. As such, it is an oxidizing agent that, by virtue of its accepting electrons, is itself reduced in the process.

Examples include dithiothreitol, fullerene derivatives, such as $PC_{61BM}$ and $PC_{71BM}$, maleic anhydride, inorganic nanoparticles, oxadiazoles, discotic liquid crystals, carbon nanorods, inorganic nanorods, polymers containing CN groups, polymers containing $CF_3$ groups, and combinations thereof. Low molecular electron acceptors include, e.g. 1,3,5-tricyanobenzene, m-dinitrobenzene,1,2,4,5-tetracyanobenzene, tetrachlorophthalic anhydride, maleic anhydride, 2,4,6-trinitrotoluene, 1,3,5-trinitrobenzene, p-benzoquinone, pyromellitic anhydride, chloro-p-benzoquinone, 1,2-dicarboxy-1,2-dicyanoethylene, 2,3-dichloro-p-benzoquinone, 2,5-dichloro-p-benzoquinone, 2,6-dichloro-p-benzoquinone, 2,4,7-trinitro-9-fluorenone, trichloro-p-benzoquinone, p-iodoanil, p-bromanil, p-chloranil, o-chloranil, o-bromanil, tetracyano-p-benzoquinone, tetracyano-p-quinodimethane, 2,3-dicyano-p-benzoquinone, 2,6-dinitro-p-benzoquinone, tetracyanoethylene, 2,3-dichloro-5,6-dicyano-p-benzoquinone, and the like. High molecular electron acceptors include, e.g. vinyl butyral resin, maleic acid resin, ketonic resin, and cellulose esters, polyacetylenes, polypyrroles, polyanilines, poly(thienylenevinylene)s, polythiophenes, and poly(phenylenevinylene)s, and the like. These can be used singly or in combination of two or more.

As used herein, the term "alkyl," unless otherwise specified, refers to $C_{1-8}$ saturated straight, branched, or cyclic, primary, secondary, or tertiary hydrocarbons, including both substituted and unsubstituted alkyl groups. The alkyl group can be optionally substituted with any moiety that does not otherwise interfere with the chemistry described herein, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. Specifically included are —$CF_3$, —$CH_2CF_3$, —$CF_2CF_3$, —$CF_2CF_2CF_3$, —$CH_2CH_2CF_3$, —$CF_2CF_2CF_2CF_3$, —$CF_2CF_2CF_2CF_2CF_3$, —$CF_2CF_2CF_2CF_2CF_3$, —$CF_2CF_2CF_2CF_2CF_2CF_3$, —$CF_2CF_2CF_2CF_2CF_2CF_3$, —$CF_2CF_2CF_2CF_2CF_2CF_2CF_3$, —$CH_2CH_2CF_2CF_2CF_2CF_2CF_2CF_3$, etc.

In the text, whenever the term C(alkyl range) is used, the term independently includes each member of that class as if specifically and separately set out. It is understood to those of ordinary skill in the art that the relevant alkyl radical is named by replacing the suffix "-ane" with the suffix "-yl".

The term "protected" as used herein, and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the chemistry described herein, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from alkyl, alkoxyalkyl, including but not limited to methoxymethyl, aralkyl, including but not limited to benzyl, aryloxyalkyl such as phenoxymethyl, aryl, including but not limited to phenyl, optionally substituted with halogen (F, Cl, Br, I), alkyl or alkoxy, sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as a methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, thymine, cytosine, 6-azapyrimidine, 2-mercaptopyrimidine, uracil, and isoxazolyl.

The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine.

Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler., U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference. Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., Nature 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Determination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference.

Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates.

In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 µm, 100 µm, 200 µm, 250 µm, 275 µm or more. Alternatively or additionally the spacer height may be at most about 600 µm, 400 µm, 350 µm, 300 µm, or less. The spacer may, for example, be formed of a layer of projections form the top or bottom substrates, and/or a material inserted between the top and bottom substrates.

One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications.

In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap).

Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference.

One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.) especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.). Droplet transport voltage and frequency may be selected for performance with reagents used in specific assay protocols.

Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan.

Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference.

Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×- 3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

"Filler fluid," "immiscible fluid" and "immiscible liquid" are used interchangeably to refer to a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings. Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200C, viscosity=2.4 cSt, d=1.79), Galden HT230 (bp=230C, viscosity=4.4 cSt, d=1.82) (all from Solvay Solexis); those in the Novec line, such as Novec 7500 (bp=128C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)). Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc.

Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the present disclosure, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space. In some embodiments, the droplet actuator may be used in a vertical or substantially vertical position.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

The terms "fluidics cartridge," "digital fluidics cartridge," "droplet actuator," and "droplet actuator cartridge" as used throughout the description can be synonymous.

Reactive Molecular Species During Electrowetting

Leakage of electrons into aqueous droplets during electrowetting may lead to water electrolysis and, in the presences of salts, accompanying electrochemical reactions may generate reactive molecular species (e.g., ROS and/or hypochlorite). In addition to the generation of reactive molecular species, gas bubbles may be generated. The generation of gas bubbles may be used as a visible indicator of electrochemical reactions that may occur during electrowetting of aqueous droplets on a droplet actuator. Similarly, the absence of gas bubbles may be used as a visible indicator of reaction and/or electrowetting conditions that ameliorate water electrolysis and/or the generation of reactive molecular species.

Reactive molecular species generated during electrowetting may cause physical damage to device electrodes and dielectrics, and reaction components such as nucleic acids, enzymes, and reagents. For example, reactive molecular species may oxidize a conductive layer of a droplet actuator which may cause droplet "pinning" or pull-back as a droplet is transported in a droplet actuator. In another example, reactive molecular species may damage a dielectric layer on a droplet actuator. In yet another example, reactive molecular species may oxidize/degrade reagent components used in a biochemical reaction. In yet another example, reactive molecular species may inactivate an enzyme used in a biochemical reaction.

One consequence of the generation of gas bubbles during electrowetting of droplets in a biochemical reaction is sample loss, i.e., the failure to recover sample droplets for subsequent downstream processing and/or analysis. Another consequence of the generation of gas bubbles during electrowetting of droplets is the interference with droplet movement along a reaction path defined by the arrayed electrodes.

In the electrowetting environment of a droplet actuator, one potential source of electron leakage (i.e., an aberrant electric current) is the conductive layer on the top substrate of a droplet actuator. FIG. 1 is a schematic illustration that shows a side view of a portion of a droplet actuator 100 and illustrates the problem of leakage current in a droplet actuator.

Droplet actuator 100 includes a bottom substrate 110 and a top substrate 112 that are separated by a droplet operations gap 114. Droplet operations gap 114 is surrounded by a filler fluid 116. Filler fluid 116 is, for example, low-viscosity oil, such as silicone oil or hexadecane filler fluid. Bottom substrate 110 includes a droplet operations electrode 118 that can be used for electrowetting operations. In this example, a single droplet operations electrode 118 is shown, but any number of droplet operations electrodes 118 may be present. Droplet operations are conducted atop droplet operations electrode 118 on a droplet operations surface. A conductive layer 120 is disposed on a lower, inner layer of the top substrate 112. In one example, the conductive layer 120 is formed of poly(3,4-ethylenedioxythiophene) poly(styrenesulfonate) (PEDOT:PSS).

A dielectric layer 122 is disposed on an upper, inner surface of droplet operations electrode 118 that is facing into the droplet operations gap 114. In one example, the dielectric layer 122 is formed of Kapton®. A hydrophobic layer 124 is disposed on the lower, inner surface of the conductive layer 120 that is facing into the droplet operations gap 114. Similarly, another hydrophobic layer 124' is disposed on the upper surface of the insulating layer 122 that is facing droplet operations gap 114. In one example, the hydrophobic layers 124 and 124' are formed of CYTOP. An aqueous droplet 126 (e.g., a sample or reagent droplet) may be positioned at droplet operations electrode 118.

In an electrowetting operation, conductive layer 120 is switched from a ground (cathode) electrode to a positively charged (anode; e.g., 300 V) electrode. Similarly, droplet operations electrode 118 is switched from a positively charged (anode) electrode to a ground (cathode) electrode. In one example, the switching frequency is 30 Hz.

In a droplet actuator, one source of leakage current can be the current that flows through a droplet, such as an aqueous sample droplet or a reagent droplet, to ground, wherein the droplet can be an unintended conductive path to ground. Namely, electrons can leak from a conductive layer of the droplet actuator into the droplet that is being processed. In droplet actuator 100, as conductive layer 120 is switched from a cathode electrode to an anode electrode, electrons may leak from conductive layer 120 into aqueous droplet 126. Electron leakage from conductive layer 120 into aqueous droplet 126 may result in the electrolysis of water within aqueous droplet 126. In the presence of salts (e.g., NaCl), accompanying electrochemical reactions may generate reactive molecules (e.g., ROS and/or hypochlorite) and/or gas bubbles.

In FIG. 1, with AC current, electrochemistry occurs at both bottom substrate 110 and top substrate 112. Namely, in FIG. 1, it is assumed that current is flowing through the droplet from top-to-bottom or bottom-to-top. However, there is also the possibility that the conductive layer 120 on top substrate 112 alone is responsible for electrons accessing the aqueous droplet, which is the scenario shown below in FIG. 2.

Figure 2:
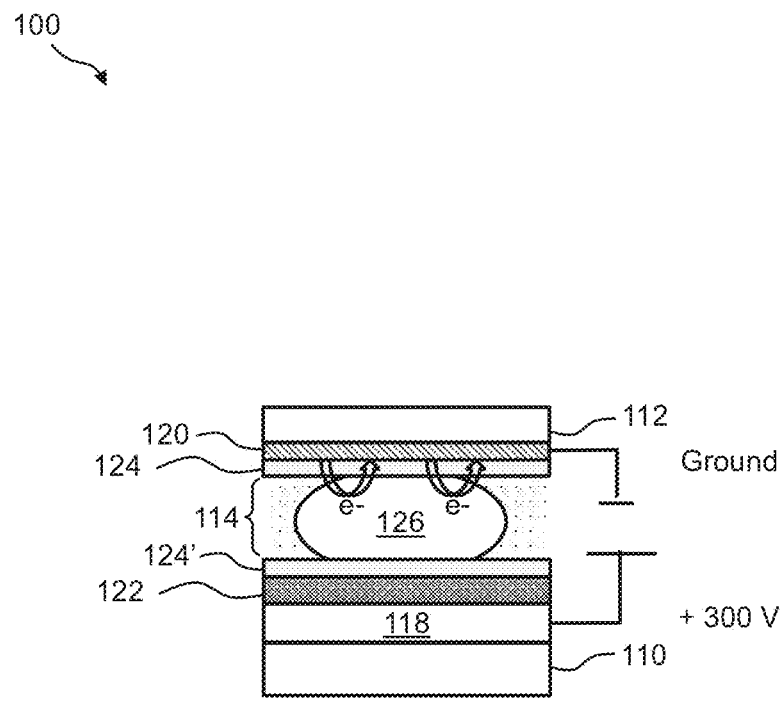
FIG. 2 is a schematic illustration that shows a side view of a portion of a droplet actuator with AC current and the possibility of electrochemistry occurring exclusively at the top substrate.

FIG. 2 is a schematic illustration that shows a side view of the droplet actuator 100 of FIG. 1 and, with AC current flowing, shows the possibility of electrochemistry occurring exclusively at the top substrate 112. Namely, the conductive layer 120 on the top substrate 112 alone is the source of electron leakage into the aqueous droplet 126.

At the cathode, a favorable reaction (e.g., $E^0=-0.83$ V) is the electrolysis of water ($H_2O$) and the generation of hydrogen gas. An example of the electrochemical reactions that may occur when the conductive layer 120 of the droplet actuator 100 of FIG. 1 is a cathode electrode is as follows.

$2H_2O$ (liq)$+2e-\rightarrow H_2$ (g)$+2$ OH— $E^0_{red}=-0.83$ V

Na+ (aq)$+e-\rightarrow$Na $E^0_{red}=-2.71$ V

At the anode, a favorable reaction is the generation of chlorine gas ($Cl_2$; $E^0=-1.36$ V). An example of the electrochemical reactions that may occur when the conductive layer 120 of the droplet actuator 100 of FIG. 1 is an anode electrode is as follows.

$2H_2O\rightarrow O_2$ (g)$+4H++4e-$ $E^0_{ox}=-1.23$ V $2Cl-\rightarrow Cl2$ (g)$+2e-$ $E^0_{ox}=-1.36$ V (½)$Cl_2$ (g)$+H_2O\rightarrow HOCl+e-$ $E^0_{ox}=-1.63$ V In the presence of water, chlorine gas generates hypochlorite (HOCl or bleach). Hypochlorite has been shown to substantially reduce the conductivity of PEDOT: PSS, such as used to form the conductive layer 120. In addition, the PEDOT:PSS in the conductive layer 120 may react with NaCl in the aqueous droplet that may result in doping/dedoping of the PEDOT: PSS (e.g., PEDOT$^+$PSS$^-$+Na$^+$ (aq)+ Cl$^-$ (aq)+e$^-$↔PEDOT$^0$+Na$^+$PSS$^-$+Cl$^-$ (aq)). Damage to the conductive layer 120 may lead to loss of droplet movement.
Methods of Reducing Reactive Molecular Species During Electrowetting Therefore, some embodiments disclosed herein provide methods of reducing reactive molecular species in a reaction carried out in a digital fluidics device having one or more electrodes by using a reaction mixture comprising an electron acceptor additive. In some embodiments, the presence of the electron acceptor additive reduces the presence of reactive molecular species in the reaction mixture. In some embodiments, the presence of the electron acceptor additive reduces the formation of gas bubbles in the digital fluidic device. Therefore, in preferred embodiments, the electron acceptor additive does not form a gas when reduced.

In some embodiments, the presence of the electron acceptor additive in the reaction mixture reduces the physical damage to the device electrodes and dielectrics, or the reaction components such as nucleic acids (e.g., DNA), enzymes, and reagents. For example, the presence of the electron acceptor additive in the reaction mixture reduces oxidation of a conductive layer of a droplet actuator which may cause droplet "pinning" or pull-back as a droplet is transported in a droplet actuator. In some embodiments, the presence of the electron acceptor additive in the reaction mixture reduces the damage to a dielectric layer on a droplet actuator. In some embodiments, the presence of the electron acceptor additive in the reaction mixture reduces the oxidation or degradation of reagent components used in a biochemical reaction, for example, THP, TCEP, etc. In some embodiments, the presence of the electron acceptor additive in the reaction mixture reduces inactivation of an enzyme used in a biochemical reaction.

In some embodiments, the presence of the electron acceptor additive in the reaction mixture reduces or prevents the electrolysis of water in the droplets. Therefore, in preferred embodiments the electron acceptor additive has a redox potential that is lower than 830 mV.

In some embodiments, the electron acceptor additive disclosed herein is not a reactant in the reaction. For example, the electron acceptor additive may comprise phenazine ethosulfate (PES), phenazine methosulfate (PMS), DTT, (±)-α-Lipoic acid, Nile Blue A (NBA), Methylene Blue (MB), Erioglaucine, or a combination thereof.

In some embodiments, the conductivity or pH of the reaction mixture may be optimized to reduce the formation of reactive molecular species during electrowetting. For example, the reaction mixture may have a conductivity that is, is about, is greater than, is less than, 2.0 µS/cm, 2.1 µS/cm, 2.2 µS/cm, 2.3 µS/cm, 2.4 µS/cm, 2.5 µS/cm, 2.6 µS/cm, 2.7 µS/cm, 2.8 µS/cm, 2.9 µS/cm, 3.0 µS/cm, 3.1 µS/cm, 3.2 µS/cm, 3.32 µS/cm, 3.4 µS/cm, 3.5 µS/cm, 3.6 µS/cm, 3.7 µS/cm, 3.8 µS/cm, 3.9 µS/cm, 4.0 µS/cm, 4.1 µS/cm, 4.2 µS/cm, 4.3 µS/cm, 4.4 µS/cm, 4.5 µS/cm, 4.6 µS/cm, 4.7 µS/cm, 4.8 µS/cm, 4.9 µS/cm, 5.0 µS/cm, or a range between any two of the above values. In some embodiments, the reaction mixture may have a conductivity that is in a range of about 2.5±0.2 µS/cm to about 5±0.8 µS/cm. In some embodiments, the reaction mixture may have a pH that is, is about, is lower than, pH 2.0, pH 2.1, pH 2.2, pH 2.3, pH 2.4, pH 2.5, pH 2.6, pH 2.7, pH 2.8, pH 2.9, pH 3.0, pH 3.1, pH 3.2, pH 3.3, pH 3.4, pH 3.5, pH 3.6, pH 3.7, pH 3.8, pH 3.9, pH 4.0, pH 4.1, pH 4.2, pH 4.3, pH 4.4, pH 4.5, pH 4.6, pH 4.7, pH 4.8, pH 4.9, pH 5.0, pH 6.0, pH 7.0, or a range between any two of the above pH values.

In some embodiments, the salt concentration, e.g., NaCl concentration, KCl concentration, KOAc concentration, NaOAc concentration, KG concentration, etc., of the reaction mixture may be optimized to reduce the formation of reactive molecular species during electrowetting. For example, the reaction mixture may have a salt concentration that is, is about, is less than, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 30 mM, 40 mM, 50 mM, 60 mM, 70 mM, 80 mM, 90 mM, 100 mM, or a range that is between any two of the above values.

In some embodiments, electrowetting parameters, such as droplet size (i.e., digital unit ("DU") size), transport rate and electrode exposure (i.e., the motion of a droplet across the droplet actuator), may be selected to substantially reduce or entirely eliminate bubble formation during electrowetting of droplets on a droplet actuator. The formation of gas bubbles is indicative of electrochemical reactions at the surface of a droplet actuator as described hereinabove with reference to FIGS. 1 and 2.

The methods and compositions disclosed herein may be used in a variety of nucleic acid applications, for example, hybridization, amplification, ligation, extension, washing, sequencing, etc. Common reagents are described in TruSeq® Enrichment Guide, Nextera® Enrichment Sample Preparation Guide, Nextera® Rapid Capture Enrichment Guide, TruSight™ Enrichment Sample Preparation Guide, MiSeq® Reagent Kit v3 Reagent Preparation Guide, HiSeq® Cluster Kit v4 Reference Guide, HiSeq® SBS Kit v4 Reference Guide, NextSeq® 500 System User Guide, TruSeq™ RNA Sample Preparation v2 Guide, Nextera XT DNA Library Preparation Guide, Nextera Mate Pair Sample Preparation Guide, TruSeq Nano DNA Sample Preparation Guide, TruSeq® Small RNA Sample Preparation Guide, TruSeq® Stranded mRNA Sample Preparation Guide, TruSeq® Stranded Total RNA Sample Preparation Guide, TruSeq® RNA Access Library Prep Guide, etc. (Illumina®, Inc., San Diego Calif.), which is incorporated by reference herein in its entirety.

Common reagents and/or ingredients include one or more of the following: Resuspension Buffer (RSB), Nestera® Capture Target Buffer 1 (NCT1), Elute Target Buffer 1 (ET1), Elute Target Buffer 2 (ET2), Enrichment Hybridization Buffer (EHB), Enrichment Elution Buffer 1 (EE1), enrichment Wash Solution (EWS), Wash Solution 1 (WS1), Wash Solution 2 (WS2), Wash Solution 3 (WS3), PCR Master Mix (TC#-PMM), Nextera® Enrichment Amplification Mix (NEM), Nextera® Library Amplification Mix (NLM), HT1 Hybridisation buffer, HT2 Wash Buffer, PR1 Wash Buffer, PR2 Wash Buffer, PR3 Wash Buffer, SB1 Wash Buffer, SB2 Wash Buffer, SB3 Wash Buffer, USM Universal Scan Mix, SRE Scan Reagent, SRM Scan Reagent, BB2 Wash Buffer, BB3 Wash Buffer, BB4 Wash Buffer, LNW1 (Library Normalization Wash 1), LNS1 (Library Normalization Storage Buffer 1), RSB (Resuspension Buffer), BWB (Bead Wash Buffer), EPM Enhanced PCR Mix, ELB Elution Buffer, etc. (Illumina®, Inc., San Diego Calif.). In some embodiments, the reagents disclosed herein may comprise an enzyme, such as a DNA polymerase (e.g., Taq polymerase, ULTIMA DNA polymerase, KOD DNA polymerase), an RNA polymerase, a reverse transcriptase (e.g., SuperScript III Reverse Transcriptase, SuperScript IV Reverse Transcriptase, MMLV Reverse Transcriptase, iScript Reverse Transcriptase, iScript Reverse Transcriptase, Omniscript Reverse Transcriptase, AMV Reverse Transcriptase), a ligase (e.g., E. coli DNA ligase, T4 DNA ligase, Ampligase, Taq DNA ligase, Pfu DNA ligase, 9 Degrees North DNA ligase), etc. In some embodiments, the reagents disclosed herein may comprise dNTPs. Other reagents include reagents common in nucleic acid applications, such as sample preparation and/or sequencing.

Electron Acceptor Additives in Immiscible Fluid

In some embodiments, one or more modified polysiloxane polymers may be included in the immiscible fluid to reduce reactive molecular species during electrowetting. For example, a modified polysiloxane polymer may function as an electron acceptor additive in the immiscible fluid to reduce the formation of gas bubbles in the digital fluidic device.

In some embodiments, the presence of the one or more modified polysiloxane polymers in the immiscible fluid reduces the physical damage to the device electrodes and dielectrics, or the reaction components such as nucleic acids (e.g., DNA), enzymes, and reagents. For example, the presence of the one or more modified polysiloxane polymers in the immiscible fluid reduces oxidation of a conductive layer of a droplet actuator which may cause droplet "pinning" or pull-back as a droplet is transported in a droplet actuator. In some embodiments, the presence of the one or more modified polysiloxane polymers in the immiscible fluid reduces the damage to a dielectric layer on a droplet actuator. In some embodiments, the presence of the one or more modified polysiloxane polymers in the immiscible fluid reduces the oxidation or degradation of reagent components used in a biochemical reaction, for example, THP, TCEP, etc. In some embodiments, the presence of the one or more modified polysiloxane polymers in the immiscible fluid reduces inactivation of an enzyme used in a biochemical reaction.

Modified Polysiloxane Polymers

It has been discovered that the addition of one or more modified polysiloxane polymers to the base oil, or the replacement of the base oil with such polymers, can dramatically reduce THP degradation. PDMS (polydimethyl siloxane) is one example of a suitable base oil, and the oil can include relatively small amounts of emulsifiers like Span 85 (sorbitan trioleate).

Representative emulsifiers include amphoteric, anionic, cationic and non-ionic emulsifiers, used alone or as a mixture, and optionally a co-emulsifier. Emulsifiers are typically chosen in an appropriate manner according to the emulsion to be obtained (W/O or O/W). The emulsifier and the co-emulsifier are generally present in the composition in a proportion ranging from 0.3% to 30% by weight, and preferably from 0.5% to 20% by weight relative to the total weight of the composition.

For the W/O emulsions, examples of emulsifiers include dimethicone copolyols such as the mixture of cyclomethicone and of dimethicone copolyol sold under the name "DC 5225 C" by the company Dow Corning, and alkyl dimethicone copolyols such as the laurylmethicone copolyol sold under the name "Dow Corning 5200 Formulation Aid" by the company Dow Corning and the cetyl dimethicone copolyol sold under the name "Abil EM 90®" by the company Goldschmidt. Surfactants for W/O emulsions that may also be used include a crosslinked elastomeric solid organopolysiloxane comprising at least one oxyalkylene group, such as those obtained according to the procedure of examples 3, 4 and 8 of U.S. Pat. No. 5,412,004, and of the examples of U.S. Pat. No. 5,811,487, in particular the product in example 3 (synthesis example) of U.S. Pat. No. 5,412,004, and such as those sold under the reference KSG 21 by the company Shin Etsu.

For the 0/W emulsions, examples of emulsifiers include non-ionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alkyl ethers; sugar esters, for instance sucrose stearate; and mixtures thereof such as the mixture of glyceryl stearate and of PEG-40 stearate.

Figure 27:
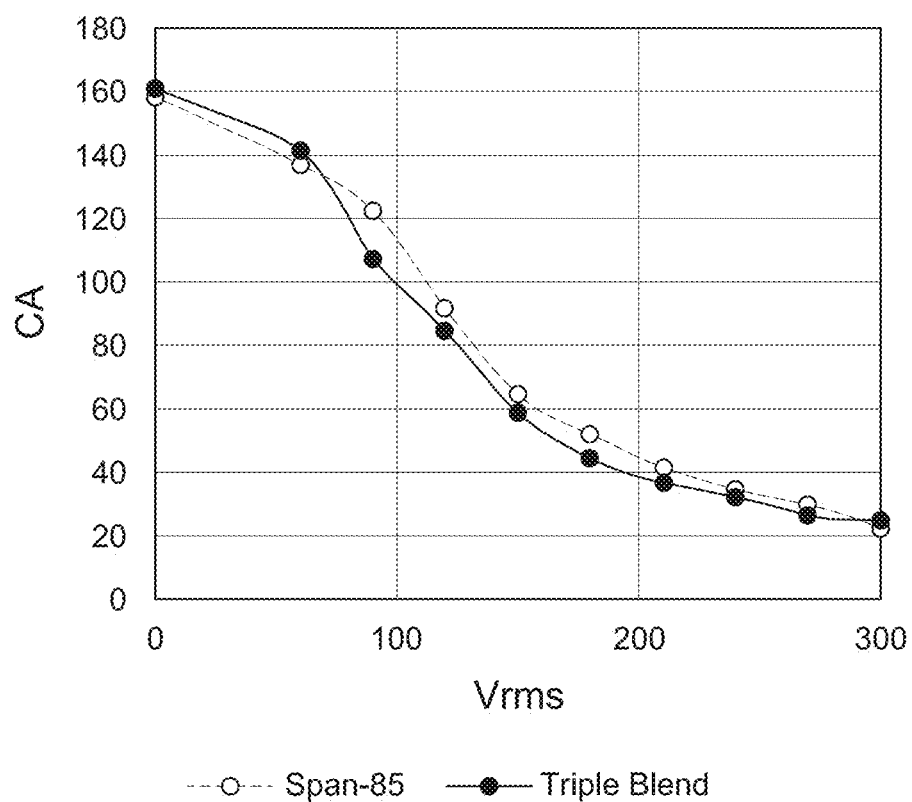
FIG. 27 shows comparable electrowetting curves for standard Mondrian filler fluid and the Triple Blend.

The modified polysiloxane polymers are typically present in the base oil in a range of between about 1 and about 90% by volume, with ranges of about 1 to about 20% by volume being more typical. However, the modified polysiloxane polymers can be present at up to 100% of the oil phase. The modified polysiloxane polymers can be present at any range that does not significantly change the electrowetting (EW) curve (FIG. 27). As used herein "significantly change" refers to more than a 5% variation in electrowetting, typically more than 10% variation in electrowetting, and most typically, more than a 20% variation in electrowetting, where electrowetting is defined as the modification of the wetting properties of a surface (which is typically hydrophobic) with an applied electric field.

The molecular weight of the polysiloxane polymers can range from between about 500 and about 1,000,000 Daltons, but is more typically in the range of between about 1,000 and 100,000 Daltons. Ideally, the polymers have a viscosity ranging from between about 1 and about 500,000 cSt, more typically, between about 1 and about 100,000 cSt, at 25° C.

The polysiloxane polymers are modified by including groups, such as a) fluorinated alkyl groups, b) polyalkylene glycol groups, c) electron acceptor groups, or d) dyes.

The polymers can be block or graft polymers. That is, the polymers can be prepared using a mixture of monomers, some of which form dialkyl, such as dimethyl siloxane units, and others of which form siloxane units with 0-1 alkyl groups and 1-2 fluoroalkyl, polyalkylene glycol, dye, or electron acceptor units, or combinations thereof. This tends to form random mixtures of the various units within a polydialkyl siloxane backbone.

In a graft copolymer, desired side chains with the various functional groups can be grafted onto a polydialkylsiloxane, if some portion of the alkyl groups contain a nucleophile or leaving group which can be reacted with a leaving group or nucleophile on the side chains to be grafted onto the polydialkylsiloxane side chain.

In a block copolymer, a first polymer or oligomer with a reactive group on the end can be reacted with a second polymer or oligomer with a reactive group on the end to form a covalent linkage between the two polymers. In some embodiments, the reactive groups do not react with each other, but both react with a common crosslinking agent to form covalent linkages.

In some embodiments, the modified polysiloxane polymer has the following formula:

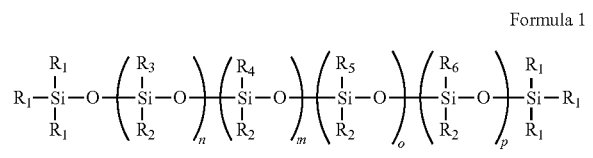

Formula 1 wherein each $R_1$ is, independently, hydrogen, $C_{1-8}$ alkyl, $C_{6-30}$ aryl, or $C_{1-15}$ alkyl-substituted $C_{6-30}$ aryl, and specific $R_1$ groups include hydrogen, methyl, ethyl, propyl, isopropyl, butyl, sec-butyl, t-butyl, isobutyl, isoamyl, and t-amyl, with methyl being particularly preferred;

$R_2$ is, independently, $R_1$, $R_3$, $R_4$, $R_5$, or $R_6$, and, in one embodiment, each $R_2$ is $R_1$;

$R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination, and in one embodiment, at least 30% of the hydrogen atoms in the alkyl moiety are replaced with fluorine, specifically including —$CH_2CH_2CF_3$, —$CH_2CH_2(CF_2)_3CF_3$, —$CF_2CF_3$, —$CF_2CF_2CF_3$, —$CH_2CH_2CF_3$, —$CF_2CF_2CF_2CF_3$, —$CF_2CF_2CF_2CF_2CF_3$, —$CF_2CF_2CF_2CF_2CF_3$, —$CF_2CF_2CF_2CF_2CF_2CF_3$, —$CF_2CF_2CF_2CF_2CF_2CF_2CF_3$, —$CF_2CF_2CF_2CF_2CF_2CF_2CF_2CF_3$, —$CH_2CH_2CF_2CF_2CF_2CF_2CF_2CF_3$;

$R_4$ is, independently, a polyalkylene glycol moiety, where the alkylene groups are, independently, $C_{2-4}$ alkylene groups and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof;

$R_5$ is, independently, a dye, which in one embodiment is erioglaucine, Nile blue, methylene blue, methyl viologen, methyl brilliant green, popop brilliant green, caffeine dye, proton sponge dye, or DDT black, linked to the polymer at any position;

$R_6$ is an electron acceptor, examples of which include dithiothreitol, which has the structure:

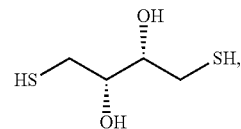

wherein the dithiothreitol moiety can be attached to the silicon atom at any of the carbons in the dithiothreitol moiety, phenazine ethosulfate and phenazine methosulfate, and +/−alpha-lipoic acid;

m is a whole number from 0 to about 300,
n is a whole number from 0 to about 300,
o is a whole number from 0 to about 300, and
p is a whole number from 0 to about 300,
wherein at least one of m, n, o, and p is not 0.

Subsets of polymers of Formula 1 including the following:

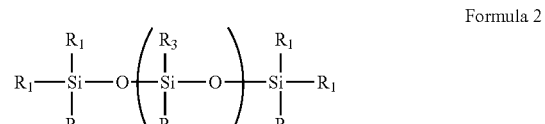

Formula 2

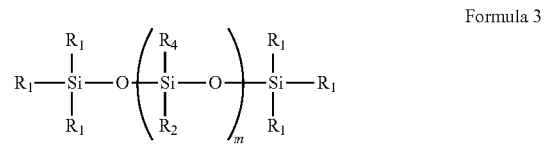

Formula 3

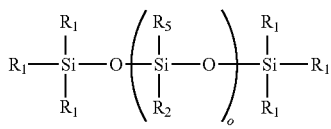

Formula 4

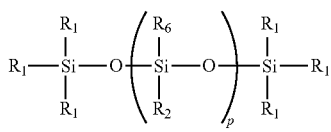

Formula 5

In Formulas 2-5, where $R_2$ is $R_1$, each polymer includes only one type of side chain, i.e., a fluorinated sidechain, a polyalkylene glycol side chain, a dye, or an electron acceptor. Where $R_2$ is any of $R_3$-$R_6$, the polymer can include two types of side chains.

One example of a polysiloxane modified to include (at least) two different types of side chains is shown below in Formula 6:

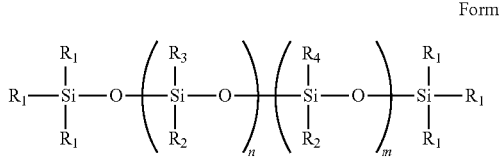

Formula 6

In Formula 6, where $R_2$ is $R_1$, and n and m are both greater than 0, the polymer includes both fluorinated and polyalkylene glycol side chains.

In some embodiments, the modified polysiloxane polymer is a block copolymer, rather than a graft copolymer, which includes a fluorinated, polyalkylene glycol, dye, or electron acceptor block (or moiety) at one or both ends of the polymer. Examples of representative polymers include those of Formulas 7 and 8, below:

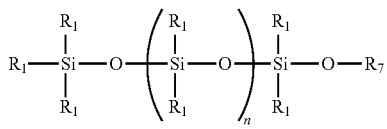

Formula 7

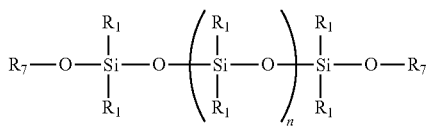

Formula 8

In Formulas 7 and 8, $R_1$ is as defined above, and $R_7$ is a $R_3$, $R_4$, $R_5$, or $R_6$ moiety coupled to the Si—O terminus of the polysiloxane, either directly or through a functional group that couples the polysiloxane to the moiety/moieties.

In other embodiments, rather than the polysiloxane terminating in an Si—O group, it terminates on one or both sides in an Si-functional group, which functional group (such as epoxy, carboxy, amine, carbonate, halide, thiol, ketone, aldehyde, imine, and the like) couples to the $R_3$, $R_4$, $R_5$, or $R_6$ moiety/moieties.

In other embodiments, one or more of the $R_1$ moieties in Formulas 7 or 8 is replaced with an $R_3$, $R_4$, $R_5$, or $R_6$ moiety.

Specific fluorinated polymers include FMS-121 and FMS-141. FMS-121 has a molecular weight of between about 900 and 1000, a viscosity of between about 80 and about 120 cSt, and includes at least one —$CH_2CH_2CF_3$ side chain. FMS-124 has a molecular weight of about 14k, a viscosity of about 10k cSt, and includes at least one —$CH_2CH_2CF_3$ side chain.

One example of a specific polyalkylene oxide-containing polysiloxane is FMS-736. FMS-736 has a viscosity of between about 400 and about 7k cSt, and includes one or more side chains that include four ethylene oxide units.

In one embodiment, in addition to the modified polysiloxanes described herein, the solutions can include one or more of the electron acceptors (not bound to the polysiloxanes) and/or low-conductivity buffers (e.g., about $5.5 \times 10^{-8}$ S/cm, about $10^{-7}$ S/cm, about $10^{-6}$ S/cm, etc.), and/or dyes (also not bound to the polysiloxanes), such as erioglaucine, Nile blue, or methylene blue.

In some embodiments, the modified polysiloxane polymer has the following formula:

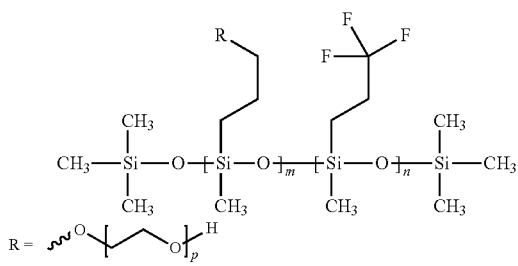

Formula 9 wherein PEG length=200 g/mol (5 EO units), m=1-300, n=1-300, and p=1-50. In some embodiments, the electron acceptor additive is FMS-141, CMS-222, SIB1816, or a combination thereof. As used herein "FMS-141" is also known as POLY(3,3,3-TRIFLUOROPROPYLMETHYLSILOXANE). As used herein, "CMS-222" is also known as (HYDROXYPROPYLENEOXYPROPYL)METHYLSILOXANE-DIMETHYLSILOXANE COPOLYMER. As used herein, "SIB-1816" is known as 1,3-BIS(TRIDECAFLUORO-1,1,2,2-TETRAHYDROOCTYL) TETRAMETHYLDISILOXANE. Each of these compositions are commercially available from Gelest, Inc (Morrisville, Pa.).

For example, FMS-141 may be present in the immiscible fluid at a concentration that is, is about, is less than, is more than, 1%, 2%, 3%, 4%, 5%, 6%, 7%, 8%, 9%, 10%, 15%, 20%, or a range between any two of the above values. For example, CMS-222 may be present in the immiscible fluid at a concentration that is, is about, is less than, is more than, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or a range between any two of the above values. For example, SIB1816 may be present in the immiscible fluid at a concentration that is, is about, is less than, is more than, 1%, 2%, 3%, 4%, 5%, 6%, 7%, 8%, 9%, 10%, 15%, 20%, or a range between any two of the above values.

In some embodiments, the modified polysiloxane polymers described herein are graft copolymers or block copolymers, which include polymer blocks or polymer chains that function as electron acceptors. Examples include copolymers of siloxanes with polyacetylenes, polypyrroles, polyanilines, poly(thienylenevinylene)s, polythiophenes, and poly(phenylenevinylene)s, any of which can be substituted or unsubstituted and branched or unbranched.

In some embodiments, the disclosure provides methods of conducting a sequencing reaction in the presence of an electrode while at the same time reducing reactive molecular species. In some embodiments, the sequencing reaction is a sequencing-by-synthesis (SBS) reaction. The methods include, among other things, the use of low conductivity buffers to substantially reduce or entirely eliminate the formation of reactive molecular species while conducting a sequencing reaction in the presence of an electrode. In some embodiments, electron acceptor additives are used to substantially reduce or entirely eliminate the formation of reactive molecular species while conducting a sequencing reaction in the presence of an electrode. In some embodiments, lower pH buffers are used to substantially reduce or entirely eliminate the formation of reactive molecular species while conducting a sequencing reaction in the presence of an electrode. In some embodiments, droplet electrowetting parameters (e.g., droplet size, transport rate, and/or electrode exposure) are selected to substantially reduce or entirely eliminate the formation of reactive molecular species while conducting a sequencing reaction in the presence of an electrode.

In some embodiments, the disclosure provides a method of conducting a DNA amplification reaction in the presence of an electrode while at the same time reducing reactive molecular species. In some embodiments, the DNA amplification reaction is a NuPCR amplification reaction (Illumina, Inc.). The methods include, among other things, the use of low conductivity buffers to substantially reduce or entirely eliminate the formation of reactive molecular species while conducting a DNA amplification reaction in the presence of an electrode. In some embodiments, electron acceptor additives are used to substantially reduce or entirely eliminate the formation of reactive molecular species while conducting a DNA amplification reaction in the presence of an electrode. In some embodiments, lower pH buffers are used to substantially reduce or entirely eliminate the formation of reactive molecular species while conducting a DNA amplification reaction in the presence of an electrode. In some embodiments, droplet electrowetting parameters (e.g., droplet size, transport rate, and/or electrode exposure) are selected to substantially reduce or entirely eliminate the formation of reactive molecular species while conducting a DNA amplification reaction in the presence of an electrode.

In some embodiments, the disclosure provides methods of substantially reducing or eliminating sample loss while conducting a biochemical reaction in the presence of an electrode. In some embodiments, sample loss is due to the formation of gas bubbles while conducting a biochemical reaction in the presence of an electrode. In some embodiments, the biochemical reaction is performed on a droplet actuator comprising multiple sample electrowetting lanes (e.g., 8 or 26 sample electrowetting lanes) that is used to perform a multiplexed biochemical reaction. The methods include, among other things, the use of low conductivity buffers to substantially reduce or entirely eliminate sample loss while conducting a biochemical reaction in the presence of an electrode. In some embodiments, electron acceptor additives are used to substantially reduce or entirely eliminate sample loss while conducting a biochemical reaction in the presence of an electrode. In some embodiments, lower pH buffers are used to substantially reduce or entirely eliminate sample loss while conducting a biochemical reaction in the presence of an electrode. In some embodiments, droplet electrowetting parameters (e.g., droplet size, transport rate, and/or electrode exposure) are selected to substantially reduce or entirely eliminate sample loss while conducting a biochemical reaction in the presence of an electrode.

In some embodiments, the disclosure provides methods of substantially reducing or eliminating damage and/or breakdown of electrowetting electrodes while conducting a biochemical reaction in the presence of an electrode. For example, reactive molecular species may oxidize a conductive layer on a droplet actuator which may cause droplet "pinning" or pull-back as the droplet is transported during a biochemical reaction. The methods include, among other things, the use of low conductivity buffers to substantially reduce or entirely eliminate damage and/or breakdown of electrowetting electrodes while conducting a biochemical reaction in the presence of an electrode. In some embodiments, electron acceptor additives are used to substantially reduce or entirely eliminate damage and/or breakdown of electrowetting electrodes while conducting a biochemical reaction in the presence of an electrode. In some embodiments, lower pH buffers are used to substantially reduce or entirely eliminate damage and/or breakdown of electrowetting electrodes while conducting a biochemical reaction in the presence of an electrode. In some embodiments, droplet electrowetting parameters (e.g., droplet size, transport rate, and/or electrode exposure) are selected to substantially reduce or entirely eliminate the damage and/or breakdown of electrowetting electrodes while conducting a biochemical reaction in the presence of an electrode.

Synthetic Methods

Block copolymers can be prepared, for example, by appending a functional group, such as an epoxy, carboxylic acid, amine, carbonate, halide, thiol, ketone, aldehyde, imine, and the like, to one or both ends of the polysiloxane. These functional groups can be used to covalently couple the polysiloxane, at one or both ends, to one or two $R_3$, $R_4$, $R_5$, or $R_6$ moiety/moieties. The choice of functional group will depend, among other things, on the reactive functional groups on the $R_3$, $R_4$, $R_5$, or $R_6$ moiety/moieties that are available for reaction with the functional group on the polysiloxane. Precursors for the $R_3$, $R_4$, $R_5$, or $R_6$ moiety/moieties can be used, where a leaving group or nucleophile not ordinarily found on these moieties can be present, and used to couple with the functional group on the polysiloxane.

Polysiloxanes functionalized with epoxy groups are described, for example, in U.S. Pat. No. 8,293,839. U.S. Pat. No. 4,754,014 discloses graft copolymers made by reacting an epoxy with a urethane-containing polysiloxane.

The organo-siloxane polymer having an epoxy or other suitable functional group, used to prepare the modified polysiloxanes described herein, typically has a viscosity of about 1 to about 100,000 centistokes (cSt), for example about 1 to about 10,000 centistokes, at about 25° C., though viscosities outside this range are acceptable.

Graft copolymers can be prepared, for example, by ring opening polymerization of appropriate precursors. A brief description of silicon organic chemistry is provided below to more fully explain the concept.

A siloxane is a functional group in organosilicon chemistry with the Si—O—Si linkage. The parent siloxanes include the oligomeric and polymeric hydrides with the formulae $H(OSiH_2)$. OH and $(OSiH_2)_1$. Siloxanes also include branched compounds, the defining feature of which is that each pair of silicon centers is separated by one oxygen atom. The siloxane functional group forms the backbone of silicones, the premier example of which is polydimethylsiloxane. The functional group (RO)₃Si is called siloxy.

The main route to siloxane functional groups is by condensation of two silanols:

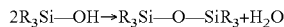
2R₃Si—OH→R₃Si—O—SiR₃+H₂O

Usually the silanols are generated in situ by hydrolysis of silyl chlorides. With a disilanol, R₂Si(OH)₂ (derived from double hydrolysis of a silyldichloride), the condensation can afford linear products terminated with silanol groups:

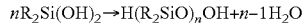
$nR_2Si(OH)_2 \rightarrow H(R_2SiO)_nOH + n-1H_2O$

Alternatively the disilanol can afford cyclic products:

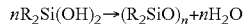
$nR_2Si(OH)_2 \rightarrow (R_2SiO)_n + nH_2O$

Cyclomethicones are a group of methyl siloxanes, a class of liquid silicones (cyclic polydimethylsiloxane polymers) that possess the characteristics of low viscosity and high volatility.

Random polysiloxane copolymers containing controlled number average molecular weights (Mns) and compositions with systematically varied concentrations of hydridomethylsiloxy- or vinylmethylsiloxy-units can be prepared via ring-opening equilibrations of cyclosiloxane tetramers.

These precursors can be functionalized with precise concentrations of pendent moieties via hydrosilation or free radical addition reactions. Hydrosilylation, also called catalytic hydrosilation, describes the addition of Si—H bonds across unsaturated bonds. Ordinarily the reaction is conducted catalytically and usually the substrates are unsaturated organic compounds. Alkenes and alkynes give alkyl and vinyl silanes; aldehydes and ketones give silyl ethers. Accordingly, one can append fluorinated side chains by using fluoro-alkenes in a hydrosilation reaction. Specific concentrations of hydrido- or vinyl-reactive sites can be crosslinked via hydrosilation to yield desired products. Vinylmethylsiloxy units can be reacted with free radicals to attach a side chain.

Further, organosilicon Grignard reagents react with halogen containing compounds in a dry solvent such as THF or THF/ether, where n=1-3, R=an organic group and X=Br or Cl:

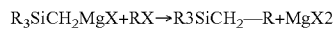
R₃SiCH₂MgX+RX→R3SiCH₂—R+MgX2

Accordingly, where the polysiloxane includes a halogen, such as a chloride, bromide, or iodide, either on the silicon, or on an alkylene, such as a methylene, group attached to the polysiloxane, a Grignard reagent can be formed, and this Grignard reagent used to couple to desired side chains.

Further, where the polysiloxane includes a halogen, either on the silicon, or on an alkylene, such as a methylene, group attached to the polysiloxane, the terminal hydroxy group on a polyalkylene glycol moiety can react with the halogen in a nucleophilic displacement reaction to attach a polyalkylene glycol side chain.

A representative synthesis of fluorosiloxanes is disclosed in U.S. Pat. No. 8,841,473, where fluorosilicone copolymers are prepared from epoxy group-containing polysiloxanes. A nucleophilic groups carries out a nucleophilic opening of the oxirane ring in the epoxy-functional polysiloxanes. One such nucleophilic group is the hydroxyl group in a fluorinated alcohols of the general formula:

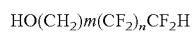
$HO(CH_2)_m(CF_2)_nCF_2H$ wherein n and m in this instance have the meaning specified in U.S. Pat. No. 8,841,473.

Using these general processes, and variations thereof within the skill of one of ordinary skill in the art, one can prepare polymers with fluorinated and/or polyalkylene glycol side chains.

Where dyes or electron acceptors are to be coupled to the polymers, variations of this chemistry can be used. In such a case, the dyes or electron acceptors can be modified to include one or more reactive groups capable of coupling with polysiloxanes using the reactions described herein, or variations thereof.

Systems

Some embodiments disclosed herein provide a system for conducting a reaction in the presence of an activated electrode while reducing the formation of reactive molecular species, which comprises a fluidics cartridge comprising an electrowetting array having a plurality of electrodes, a reaction droplet comprising a reaction mixture, and an immiscible fluid surrounding the reaction droplet. In some embodiments, the reaction mixture, the immiscible fluid, or both, may comprise an electron acceptor additive as disclosed herein.

In some embodiments, the fluidics cartridge may comprise a substrate having a CYTOP coating. The thickness of the CYTOP coating may be optimized to reduce reactive molecular species during electrowetting. For example, an increased thickness of the CYTOP coating may reduce the formation of gas bubbles in the digital fluidic device. In some embodiments, the CYTOP coating may have a thickness that is, is about, is greater than, 100 nm, 200 nm, 300 nm, 400 nm, 500 nm, 600 nm, 700 nm, 800 nm, 900 nm, 1,000 nm, 2,000 nm, 3,000 nm, 4,000 nm, or a range that is between any two of the above values.

In some embodiments, an increased thickness of the CYTOP coating reduces the physical damage to the device electrodes and dielectrics, or the reaction components such as nucleic acids (e.g., DNA), enzymes, and reagents. For example, an increased thickness of the CYTOP coating reduces oxidation of a conductive layer of a droplet actuator which may cause droplet "pinning" or pull-back as a droplet is transported in a droplet actuator. In some embodiments, an increased thickness of the CYTOP coating reduces the damage to a dielectric layer on a droplet actuator. In some embodiments an increased thickness of the CYTOP coating reduces the oxidation or degradation of reagent components used in a biochemical reaction, for example, THP, TCEP, etc. In some embodiments, an increased thickness of the CYTOP coating reduces inactivation of an enzyme used in a biochemical reaction.

Figure 21:
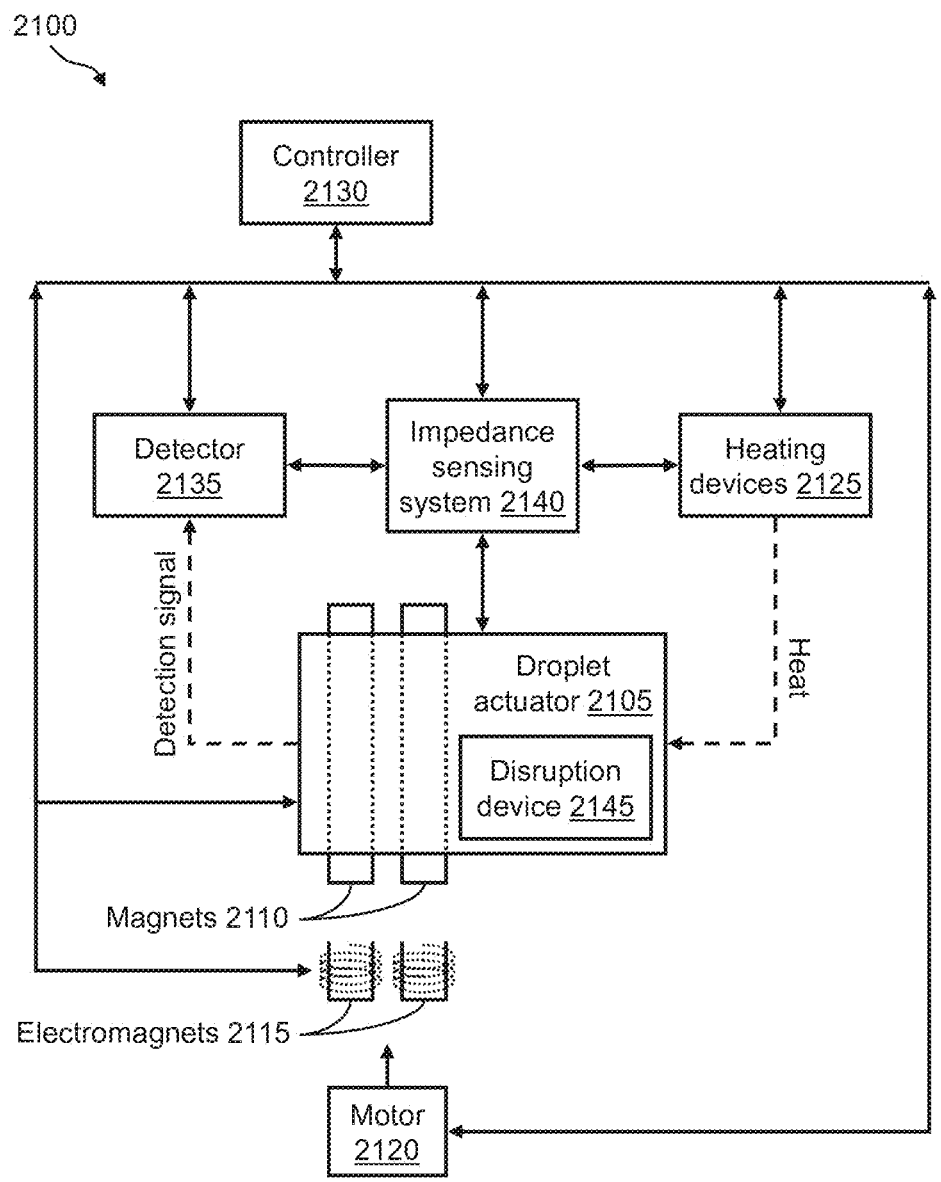
FIG. 21 is a functional block diagram of an exemplary microfluidics system that includes a droplet actuator.

FIG. 21 is a functional block diagram of an example of a microfluidics system 2100 that includes a droplet actuator 2105. Digital microfluidic technology conducts droplet operations on discrete droplets in the droplet actuator 2105, by electrowetting. roplet Droplet actuator 2105 may be designed to fit onto an instrument deck (not shown) of the microfluidics system 2100. The instrument deck may hold the droplet actuator 2105 and house other droplet actuator features, such as one or more magnets 2110, which may be permanent magnets. Optionally, the instrument deck may house one or more electromagnets 2115. Magnets 2110 and/or electromagnets 2115 are positioned in relation to droplet actuator 2105 for immobilization of magnetically responsive beads. The positions of magnets 2110 and/or electromagnets 2115 may be controlled by a motor 2120. Additionally, the instrument deck may house one or more heating devices 2125 for controlling the temperature within, for example, certain reaction and/or washing zones of droplet actuator 2105. In one example, the heating devices 2125 may be heater bars that are positioned in thermal contact with the droplet actuator 2105.

An electronic controller 2130 is configured to control the operations of the microfluidics system 2100 and is electrically coupled to various hardware components such as droplet actuator 2105, electromagnets 2115, motor 2120, and heating devices 2125. The electronic controller may also be connected to a detector 2135, an impedance sensing system 2140, and any other input and/or output devices (not shown). Controller 2130 controls the overall operation of microfluidics system 2100. Controller 2130 may, for example, be a general purpose computer, special purpose computer, personal computer, or other programmable data processing apparatus. Controller 2130 may be configured to provide processing capabilities, such as storing, interpreting, and/or executing software instructions, as well as controlling the overall operation of the system. Controller 2130 may be configured and programmed to control data and/or power aspects of these devices. For example, in one aspect, with respect to the droplet actuator 2105, the controller 2130 controls droplet manipulation by activating/deactivating electrodes.

In one example, the detector 2135 may be an imaging system that is positioned in relation to droplet actuator 2105. In one example, the imaging system may include one or more light-emitting diodes (LEDs) (i.e., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in Banerjee et al., U.S. Pat. No. 8,241,573, entitled "Systems and Devices for Sequence by Synthesis Analysis," issued on Aug. 14, 2012; Feng et al., U.S. Pat. No. 7,329,860, entitled "Confocal Imaging Methods and Apparatus," issued on Feb. 12, 2008; Feng et al., U.S. Pat. No. 8,039,817, entitled "Compensator for Multiple Surface Imaging," issued on Oct. 18, 2011; Feng et al., U.S. Patent Pub. No. 20090272914, entitled "Compensator for Multiple Surface Imaging," published on Nov. 5, 2009; and Reed et al., U.S. Patent Pub. No. 20120270305, entitled "Systems, Methods, and Apparatuses to Image a Sample for Biological or Chemical Analysis," published on Oct. 25, 2012, the entire disclosures of which are incorporated herein by reference. Such detection systems are particularly useful for nucleic acid sequencing embodiments.

An impedance sensing system 2140 may be any circuitry for detecting impedance at a specific electrode of the droplet actuator 2105. In one example, the impedance sensing system 2140 may be an impedance spectrometer. The impedance sensing system 2140 may be used to monitor the capacitive loading of any electrode, such as any droplet operations electrode, with or without a droplet thereon. For examples of suitable capacitance detection techniques, see Sturmer et al., International Patent Pub. No. WO/2008/101194, entitled "Capacitance Detection in a Droplet Actuator," published on Dec. 30, 2009; and Kale et al., International Patent Pub. No. WO/2002/080822, entitled "System and Method for Dispensing Liquids," published on Feb. 26, 2004, the entire disclosures of which are incorporated herein by reference.

The droplet actuator 2105 may also include a disruption device 2145. The disruption device 2145 may be any device that promotes disruption (lysis) of materials, such as tissues, cells and spores in a droplet actuator. The disruption device 2145 may, for example, be a sonication mechanism, a heating mechanism, a mechanical shearing mechanism, a bead beating mechanism, physical features incorporated into the droplet actuator 2105, an electric field generating mechanism, thermal cycling mechanism, and any combinations thereof. The disruption device 2145 may be controlled by the controller 2130.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electromagnetic, infrared, or semiconductor system, apparatus, device, or propagation medium. The computer readable medium may include transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code can be executed locally and/or remotely. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of the present disclosure are described with reference to various methods and method steps. It will be understood that each method step can be implemented by the program code and/or by machine instructions. The program code and/or the machine instructions may create means for implementing the functions/acts specified in the methods.

The program code can also be stored in a computer-readable memory that can direct the processor, computer, or other programmable data processing apparatus to function in a particular manner, such that the program code stored in the computer-readable memory produces or transforms an article of manufacture including instruction means that implement various aspects of the method steps.

The program code can also be loaded onto a computer or other programmable data processing apparatus to cause a series of operational steps to be performed to produce a processor/computer implemented process such that the program code provides steps for implementing various functions/acts specified in the methods of the present disclosure.

Kits

Some embodiments disclosed herein provide kits for conducting a reaction in the presence of an activated electrode while reducing the formation of reactive molecular species comprising a compartment comprising a reagent having an electron acceptor additive, wherein conducting a reaction in a reaction droplet comprising the reagent in the presence of an activated electrode results in reduced interference by reactive molecular species.

In some embodiments, the presence of the electron acceptor additive in the reaction mixture reduces or prevents the electrolysis of water in the droplets. Therefore, in preferred embodiments the electron acceptor additive has a redox potential that is lower than 830 mV.

In some embodiments, the electron acceptor additive disclosed herein is not a reactant in the reaction. For example, the electron acceptor additive may comprise phenazine ethosulfate (PES), phenazine methosulfate (PMS), DTT, (±)-α-Lipoic acid, Nile Blue A (NBA), Methylene Blue (MB), Erioglaucine, or a combination thereof.

Sequencing Methods

The devices, systems and methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

"Sequencing-by-synthesis ("SBS") techniques" generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminscent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in International Patent Pub. No. WO 04/018497 and U.S. Pat. No. 7,057,026, the disclosures of which are incorporated herein by reference in their entireties. This approach is being commercialized by Solexa (now Illumina Inc.), and is also described in International Patent Pub. No. WO 91/06678 and International Patent Pub. No. WO 07/123,744, the disclosures of which are incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference in its entirety). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Pub. No. 2007/0166705, U.S. Patent Pub. No. 2006/0188901, U.S. Pat. No. 7,057,026, U.S. Patent Pub. No. 2006/0240439, U.S. U.S. Patent Pub. No. 2006/0281109, International Patent Pub. No. WO 05/065814, U.S. Patent Pub. No. 2005/0100900, International Patent Pub. No. WO 06/064199, International Patent Pub. No. WO 07/010,251, U.S. U.S. Patent Pub. No. 2012/0270305 and U.S. Patent Pub. No. 2013/0260372, the disclosures of each of which are incorporated herein by reference in its entirety.

Some embodiments can utilize detection of four different nucleotides using fewer than four different labels. For example, SBS can be performed utilizing methods and systems described in U.S. Patent Pub. No. 2013/0079232, which is incorporated herein by reference in its entirety. As a first example, a pair of nucleotide types can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g., dATP having a label that is detected in the first channel when excited by a first excitation wavelength), a second nucleotide type that is detected in a second channel (e.g., dCTP having a label that is detected in the second channel when excited by a second excitation wavelength), a third nucleotide type that is detected in both the first and the second channel (e.g., dTTP having at least one label that is detected in both channels when excited by the first and/or second excitation wavelength) and a fourth nucleotide type that lacks a label that is not, or minimally, detected in either channel (e.g., dGTP having no label).

Further, as described in the incorporated disclosure of U.S. Patent Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation (SBL) techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBL systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as $\alpha$-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and $\gamma$-phosphate-labeled nucleotides as described, for example, in U.S. Pat. Nos. 7,329,492 and 7,211,414 (each of which is incorporated herein by reference in its entirety) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 and U.S. Patent Pub. No. 2008/0108082 (each of which is incorporated herein by reference in its entirety). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Patent Pub. No. 2009/0026082; U.S. Patent Pub. No. 2009/0127589; U.S. Patent Pub. No. 2010/0137143; or U.S. Patent Pub. No. 2010/0282617, each of which is incorporated herein by reference in its entirety. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at a density that is, is about, is less than, or is more than, 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or a density that is a range between any of these values, for example, 10 features/cm$^2$ to 5,000,000 features/cm$^2$, 100 features/cm$^2$ to 1,000,000 features/cm$^2$, 500 features/cm$^2$ to 100,000 features/cm$^2$, 1,000 features/cm$^2$ to 50,000 features/cm$^2$, 5,000 features/cm$^2$ to 10,000 features/cm$^2$, etc.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Patent Pub. No. 2010/0111768 A1 and U.S. patent application Ser. No. 13/273,666, each of which is incorporated herein by reference in its entirety. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. patent application Ser. No. 13/273,666, which is incorporated herein by reference in its entirety.

EXAMPLES

Example 1. Effect of Buffer Conductivity on Bubble (Gas) Formation

Table 1 below shows parameters that were used to define a set of experimental conditions used to examine the effect of buffer conductivity on gas bubble formation and droplet recovery during electrowetting of sample droplets. Parameters that were varied for each sample lane included electrowetting parameters of voltage (i.e., 100V or 300V), droplet transport rate (1 sec or 5 sec), and switching frequency (i.e., 1 Hz or 30 Hz), and droplet parameters of incubation temperature (i.e., 37° C. or 70° C.), sample buffer pH (i.e., ACES buffer at pH 7.0 or ethanolamine buffer at 9.9), and sample buffer conductivity (i.e., 0.1M NaCl or 0.01M NaCl). All buffers included 0.01% Tween® 20.

TABLE 1

Parameters used to define experimental conditions

| Pattern | Voltage | Temp ° C. | Time | pH | Conductivity | Transport Rate | Switching Frequency |
|---|---|---|---|---|---|---|---|
| --+-++- | 100 V | 37 | 4 Hr | 7.0 | 0.1M | 5 sec | 1 Hz |
| ------- | 100 V | 37 | 1 Hr | 7.0 | 0.01M | 1 sec | 1 Hz |
| -+--+-+ | 100 V | 70 | 1 Hr | 7.0 | 0.1M | 1 sec | 30 Hz |
| ++--++- | 300 V | 70 | 1 Hr | 7.0 | 0.1M | 5 sec | 1 Hz |
| -+-+-+- | 100 V | 70 | 1 Hr | 9.9 | 0.01M | 5 sec | 1 Hz |
| +++++++ | *300 V* | 70 | *4 Hr* | *9.9* | *0.1M* | *5 sec* | *30 Hz* |
| +-++-+- | 300 V | 37 | 4 Hr | 9.9 | 0.01M | 5 sec | 1 Hz |
| -++++-- | 100 V | 70 | 4 Hr | 9.9 | 0.1M | 1 sec | 1 Hz |
| +++---- | 300 V | 70 | 4 Hr | 7.0 | 0.01M | 1 sec | 1 Hz |
| +--++-- | 300 V | 37 | 1 Hr | 9.9 | 0.1M | 1 sec | 1 Hz |
| --++--+ | 100 V | 37 | 4 Hr | 9.9 | 0.01M | 1 sec | 30 Hz |
| ++=+--+ | 300 V | 70 | 1 Hr | 9.9 | 0.01M | 1 sec | 30 Hz |
| +----++ | 300 V | 37 | 1 Hr | 7.0 | 0.01M | 5 sec | 30 Hz |
| ---++++ | 100 V | 37 | 1 Hr | 9.9 | 0.1M | 5 sec | 30 Hz |
| -++--++ | 100 V | 70 | 4 Hr | 7.0 | 0.01M | 5 sec | 30 Hz |
| +=+-+-+ | 300 V | 37 | 4 Hr | 7.0 | 0.1M | 1 sec | 30 Hz |

The data shown in Table 1 also define a set of "stress" conditions, which are italicized in Table 1, that may be used to manipulate sample droplets for subsequent analysis of bubble formation, electron leakage, sample loss, and generation of reactive molecular species. The defined electrowetting parameters are 300 V, 4 hr incubation at 70° C., 30 Hz switching frequency, and a 5 sec droplet transport rate.

Table 2 below shows a summary of the effect of buffer conductivity on bubble formation and droplet recovery for the set of experimental conditions italicized in Table 1. The data showed that all sample lanes that contained droplets with higher conductivity buffers (i.e., 100 mM NaCl) had bubbles after 4 hours of incubation at 70° C. and substantial sample loss, i.e., no sample droplets were recovered for downstream analysis. In sample lanes that contained droplets with lower conductivity buffers (i.e., 10 mM NaCl), only 4 out of 8 lanes for each buffer type (i.e., ACES pH 7 and ethanolamine pH 9.9) had bubbles after 4 hours of incubation and no samples were recovered from these lanes for downstream analysis. Samples were recovered from all lanes with no bubbles.

TABLE 2

Effect of buffer conductivity on bubble formation and droplet recovery

| Buffer w/0.01% Tween ® 20 | Number of lanes with bubbles (1 hr) | Number of lanes with bubbles (4 hrs) |
|---|---|---|
| 10 mM ACES pH 7, 10 mM NaCl | 0 | 4 |
| 10 mM ACES pH 7, 100 mM NaCl | 0 | 8 (0 droplets recovered) |
| 10 mM ethanolamine pH 9.9, 10 mM NaCl | 0 | 4 |
| 10 mM ethanolamine pH 9.9, 100 mM NaCl | 0 | 8 (0 droplets recovered) |

The data shown in Table 2 indicates that higher salt conditions (e.g., 100 mM NaCl) and therefore high buffer conductivity contributed to the generation of bubbles during electrowetting and subsequent sample loss.

Figure 3:
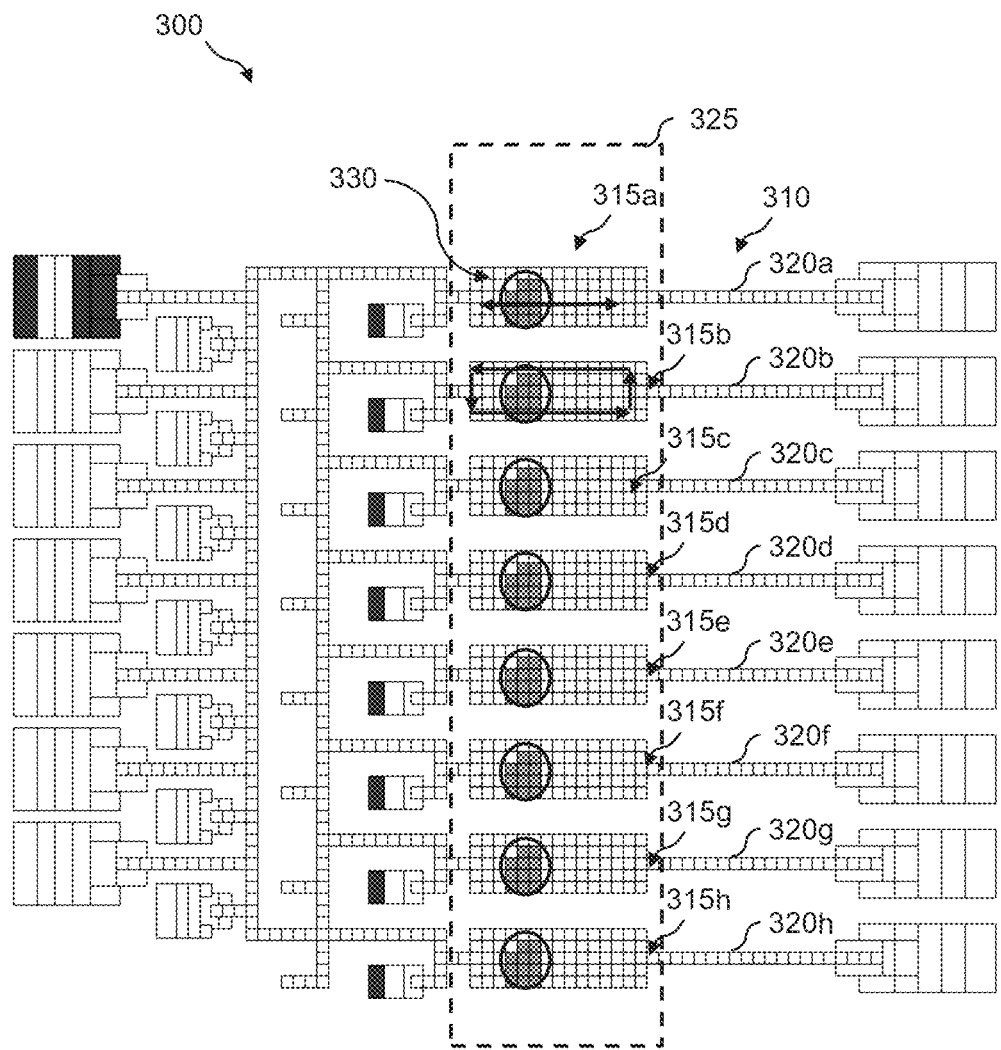
FIG. 3 is a schematic diagram illustrating an electrode arrangement suitable for evaluating the effect of different electrowetting parameters and reaction conditions on bubble formation during electrowetting of droplets.

FIG. 3 is a schematic plan view of an electrode arrangement 300 that is suitable for use in evaluating the effect of different electrowetting parameters and reaction conditions on bubble formation during electrowetting of sample droplets. Electrode arrangement 300 includes various lines of electrowetting electrodes 310 that feed various heating regions 315a through 315h in a temperature control zone 325. Droplet operations electrodes and heating regions 315a-h form 8 individual reaction lanes 320a through 320h. Droplet operations are conducted atop the droplet operations electrodes 310 on a the droplet operations surface. The temperature control zone 325 may be heated, for example, to a variety of different temperatures for carrying out desired reactions, including, for example, 50° C., 60° C., 70° C. or more. A droplet 330 may be positioned at each of the heating regions 315a-h. In one example, droplet 330 may be, for example, a slug of fluid of about 350 nL in volume. In one example, droplet 330 may be transported via droplet operations back and forth from one end of heating regions 315 to the other in repeated fashion. Transport of droplet 330 in a counterclockwise (circular) direction minimizes the amount of electrode exposure to the droplet solution. In another example, droplet 330 may be transported via droplet operations in a linear direction back and forth within heating regions 315.

Electrode arrangement 300 may be used, for example, to examine the effect of buffer composition, ionic strength, and/or conductivity on the generation of gas bubbles and reactive molecular species during electrowetting of aqueous droplets on a droplet actuator.

Electrode arrangement 300 was used to evaluate the effect of solution conductivity on gas bubble formation during electrowetting of sample droplets. Namely, the evaluation was performed during electrowetting of droplets over a three hour time course, wherein the droplets included solutions having different conductivity. Droplet solutions were loaded onto a droplet actuator and individual droplets were dispensed and transported using droplet operations to heating regions 315a-h. The droplets were transported using droplet operations in a counterclockwise (circular) direction within heating regions 315a-h using the electrowetting parameters described with reference to FIG. 2 (i.e., 300 V, incubation at 70° C., 30 Hz switching frequency, and a 5 sec droplet transport rate).

The solution compositions were, in order of lowest conductivity to highest conductivity: (1) water+0.01% Tween, (2) water+100 mM NaOAc, and (3) water+100 mM NaCl. In general, solutions that contained larger, less mobile ions, e.g., acetate ions (OAc), were less conductive than solutions that contain smaller ions, e.g., chloride ions (Cl). Thus, for the lowest conductivity solution of water+0.01% Tween, it was found that substantially no bubbles formed over a period of about 3 hours. For the next higher conductivity solution of water+100 mM NaOAc, bubbles formed at about 3 hours. For the highest conductivity solution of water+100 mM NaCl, bubbles formed at about 2 hours. Accordingly, the data show that fewer or no bubbles were formed during electrowetting of droplets having relatively lower conductivity compared with the amount of bubbles formed during electrowetting of droplets comprising a higher conductivity.

In another example, bubbles were generated during electrowetting of droplets comprising water or the sequencing buffer PR2. In this example, a single droplet actuator was used to perform three separate electrowetting runs: a first run with droplets comprising water+0.05% Tween® 20, a second run with droplets comprising PR2 buffer containing 50 mM NaCl, and a third run with droplets comprising water+0.05% Tween® 20. For each run, the droplets were transported from one end of a droplet actuator to the other end of the droplet actuator (i.e., transported in a linear direction) over a period of time. The electrowetting parameters were 300 V, 30 Hz switching frequency, 60° C. The droplet size was about 8 µL in volume. Any bubbles that were generated during each run were manually cleared from the droplet actuator prior to the subsequent run. The data showed that a substantial number of bubbles were generated during electrowetting of droplets comprising PR2 buffer containing 50 mM NaCl as compared with droplets comprising water+0.05% Tween® 20.

Table 3 shows a summary of bubble formation with increasing droplet buffer conductivity and time. In this example, droplets comprising solutions with increasing conductivity (i.e., water, 200 mM TrisOAc, 200 mM TrisCl, 100 mM NaOAc, water+100 mM NaCl, or water+100 mM KCl) were transported from one end of a droplet actuator to the other end of the droplet actuator (i.e., transported a slug in a circular direction). The electrowetting parameters were 300 V, incubation at 70° C., 30 Hz switching frequency, and a 5 sec droplet transport rate.

TABLE 3

Bubble formation with increasing buffer conductivity and time

| Buffer w/0.01% Tween ® 20 | Time | | | Bubble profile @ >3 hrs |
|---|---|---|---|---|
| | 1 hr | 2 hrs | 3 hrs | |
| Water | 0 | 0 | 1 | Large |
| 200 mM TrisOAc pH 8 | 0 | 0 | ND | |
| 200 mM TrisCl pH 8 | 0 | 0 | ND | |
| 100 mM NaOAc | 0 | 1 | 7 | Large |
| Water + 100 mM NaCl | 0 | 4 | 7 | Small (n = 2) |
| Water + 100 mM KCl | 0 | 4 | 7 | |

The conductivity (as reported in the literature or determined in-house (e.g., TrisOAc)) of the sample solutions were about: deionized water (0.0023 mS/cm), TrisOAc pH8 (3.53 mS/cm), TrisHCl pH8 (9.6 mS/cm), NaOAc (12.2 mS/cm), NaCl (18.1 mS/cm), and KCl (23.3 mS/cm). The data showed that, in general, sample solutions with higher conductivity (e.g., 100 mM NaCl or 100 mM KCl) generate more bubbles over time. In one example, the solution conductivity is about 0.0023 mS/cm.

In one example, a solution comprising a lower concentration of salt (e.g., 10 mM NaCl vs 100 mM NaCl) may be used to reduce the conductivity of a droplet and ameliorate bubble formation and/or interference with performing a biochemical assay using electrowetting on a droplet actuator. In another example, a low conductivity buffer has a conductivity lower than a 30 mM NaCl solution.

In another example, a solution comprising lower mobility/lower conductivity ions, (e.g., NaOAc vs NaCl), while maintaining the ionic strength of the solution, may be used to reduce the conductivity of a droplet and ameliorate bubble formation and/or interference with performing a biochemical assay using electrowetting on a droplet actuator.

In yet another example, the formation of bubbles was observed during active electrowetting (300V, 30 Hz, 5 sec transport rate) on a droplet actuator filled with 100 mM NaCl (i.e., filler fluid was absent) (data not shown).

Additional sources of gas formation during electrowetting were examined. For example, the formation of bubbles was not detected during active electrowetting (300V, 30 Hz, 5 sec transport rate) on a droplet actuator filled with 5 cSt silicone oil (PDMS) filler fluid in the absence of aqueous droplets (data not shown).

Example 2. Electron Transfer from Droplet Actuator Electrode to Droplet Solution Examples of using the electrode arrangement 300 to evaluate the transfer of electrons from the conductive layer (electrode) of a droplet actuator to a droplet solution are described with reference to FIG. 4.

Figure 4:
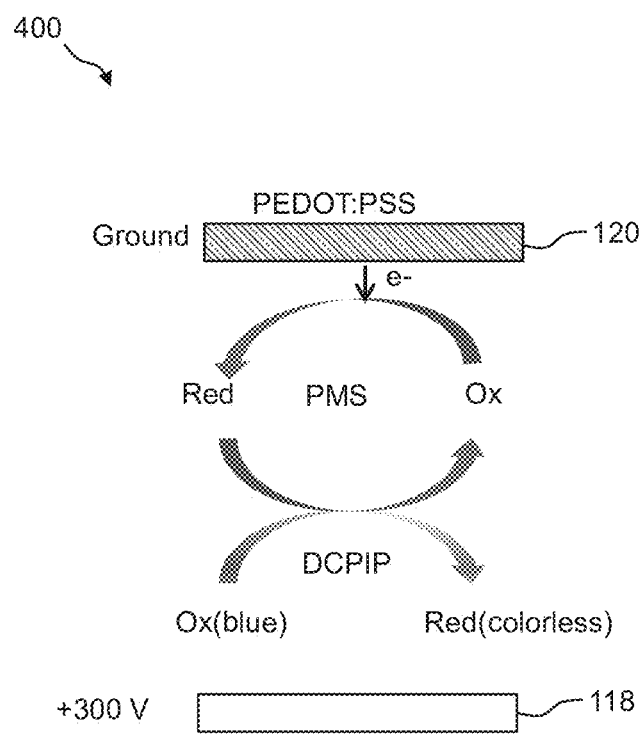
FIG. 4 is a schematic diagram illustrating a colorimetric assay used to demonstrate the transfer of electrons from the conductive layer of a droplet actuator to a droplet during electrowetting.

FIG. 4 is a schematic diagram 400 of a colorimetric assay that was used to demonstrate the transfer of electrons from the conductive layer of a droplet actuator to a droplet solution during electrowetting. In this assay, phenazine methosulfate (PMS) was used as an intermediate electron carrier and 2,6-dichlorophenolindopenol (DCPIP) is used as an electron acceptor. DCPIP is a redox dye that is blue in the oxidized state (Ox (blue)) and is colorless in the reduced state (Red (colorless)). In the presence of free electrons (e.g., from conductive layer 120), PMS is reduced and transfers the electron to DCPIP. As DCPIP accepts the electron, the color of the solution changes from blue to colorless.

In this assay, a droplet solution comprising PMS (40 mM) and DCPIP (1 mM) was loaded onto a droplet actuator comprising electrode arrangement 300 of FIG. 3. Eight individual droplets (n=8) were dispensed and transported using droplet operations to heating regions 315*a-h*. The droplets were transported using droplet operations back and forth in a counterclockwise direction within heating regions 315 for a total of 9 minutes using the electrowetting parameters described with reference to FIG. 2 (i.e., 300 V, 4 hr incubation at 70° C., 30 Hz switching frequency, and a 5 sec droplet transport rate).

Further, in the colorimetric assay described in FIG. 4, at about the 2 minute time point, all droplets were dark (blue) in color, i.e., DCPIP was in the oxidized state. At about the 9 minute time point, all droplets are colorless, i.e., DCPIP was in the reduced state. The data demonstrate transfer of electrons from the droplet actuator electrode to the droplets during electrowetting. The colorimetric assay described in FIG. 4 was also used to estimate the leakage current during electrowetting of droplets.

Figure 5:
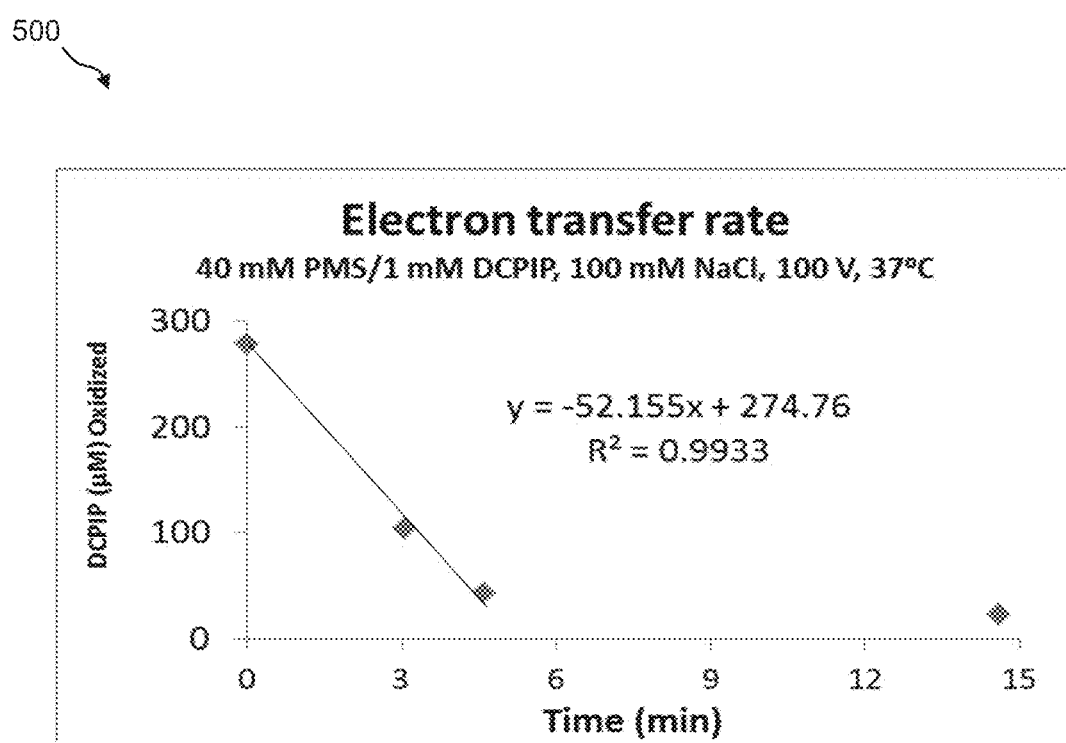
FIG. 5 is an exemplary plot of the electron transfer rate as a function of the amount of oxidized 2,6-dichlorophenolindopenol (DCPIP) and time.

FIG. 5 shows a plot 500 of the electron transfer rate as a function of the amount of oxidized DCPIP and time. In this example, a droplet solution comprising PMS (40 mM), DCPIP (1 mM), and 100 mM NaCl was loaded onto a droplet actuator comprising electrode arrangement 300 of FIG. 3. Individual droplets (about 350 nL=1 DU "1 digital unit") were dispensed and transported using droplet operations to heating electrodes regions 315. Heating electrode region 315 was heated to a temperature of 37° C. The electrowetting voltage was 100 V. Droplets (about 10 nL) were recovered from the droplet actuator over a 15 minute time course and the amount of DCPIP (oxidized; blue) present in each recovered droplet volume was determined at 600 nm. The extinction coefficient of DCPIP is $2.1\times10^4$ $M^{-1}$ $cm^{-1}$ at 600 nm. The estimated leakage current is about 59.2 nA/DU (i.e., 52 µM DCPIP/min→104.4 µM e–/min→59.2 nA/DU; 1 DU~350 nL). The data demonstrate the flow of electrons into the droplets.

Example 3. Electron Acceptor Additives Inhibit Bubble Generation

Embodiments of the methods disclosed herein use the addition of electron acceptor additives in aqueous droplets to scavenge electrons and substantially reduce or entirely eliminate the electrolysis of water and accompanying electrochemical reactions. A suitable electron acceptor additive has a redox potential that is lower than the redox potential of water (i.e., 830 mV). In another example, a suitable electron acceptor additive does not form a gas when reduced. In one example, the electron acceptor additive is phenazine methosulfate (PMS) with a redox potential of about 82 mV.

To evaluate the effect of PMS on formation of gas bubbles, a droplet solution comprising PMS (100 mM) was loaded onto a droplet actuator comprising electrode arrangement 300 of FIG. 4. Individual droplets (n=8) were dispensed and transported using droplet operations to heating regions 315*a-h*. The droplets were transported using droplet operations back and forth in a counterclockwise direction within heating regions 315*a-h* for a total of 4 hours using the electrowetting parameters described with reference to FIG. 3 (i.e., 300 V, 4 hr incubation at 70° C., 30 Hz switching frequency, and a 5 sec droplet transport rate). After 2, 3, and 4 hours of electrowetting, no bubbles were observed on the droplet actuator (data not shown).

Figure 6A:
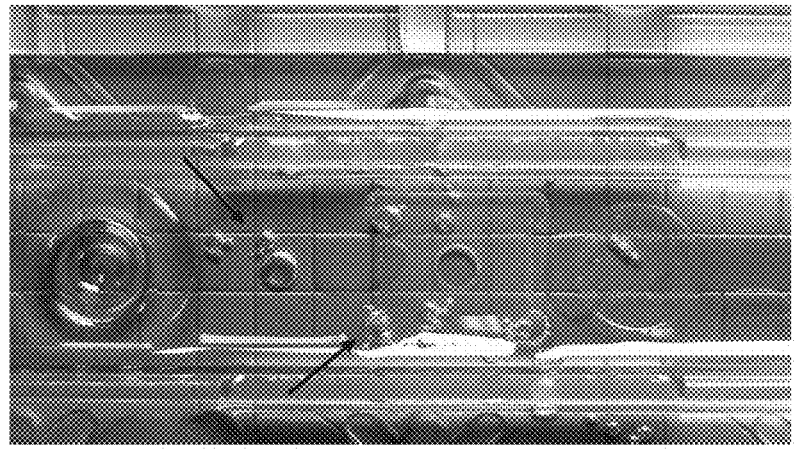
FIGS. 6A and 6B are exemplary photographs of bubble formation during electrowetting of droplets comprising PR2 buffer and of droplets comprising PR2 buffer plus phenazine methosulfate (PMS)
Figure 6B:
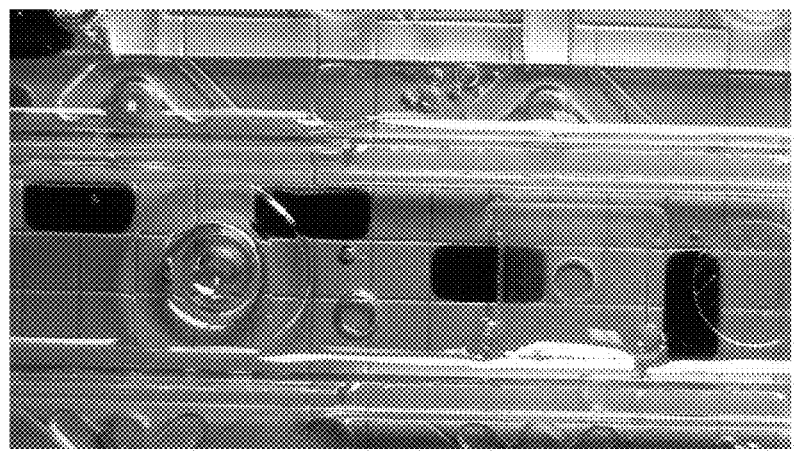

FIGS. 6A and 6B are photographs of bubble formation during electrowetting of droplets comprising PR2 buffer and of droplets comprising PR2 buffer plus phenazine methosulfate (PMS). PR2 buffer is a sequencing reaction buffer that includes 50 mM NaCl. Electrowetting of aqueous droplets comprising PR2 buffer resulted in the generation of a substantial number of bubbles. In this example, droplets were transported from one end of a droplet actuator to the other end of the droplet actuator (i.e., transported in a linear direction). The images in FIGS. 6A and 6B were taken after 3 minutes of droplet transport. Referring to FIG. 6A, the arrow indicates the presence of bubbles. Observations show that a substantial number of bubbles were generated during electrowetting of droplets comprising PR2 buffer containing 50 mM NaCl (FIG. 6A). Referring to FIG. 6B, the addition of PMS to droplet solution comprising PR2 buffer substantially reduced bubble formation during electrowetting.

A number of different reagent additives were evaluated for their ability to inhibit or substantially reduce gas bubble formation during electrowetting of aqueous droplets. Reagents were selected based on their redox potential (i.e., their ability to accept electrons). Table 4 below shows a list of the reagent additives that were evaluated and their effect on inhibiting bubble formation. In this example, the electrowetting parameters were as described with reference to FIG. 3 (i.e., 300 V, 4 hr incubation at 70° C., 30 Hz switching frequency, and a 5 sec droplet transport rate).

TABLE 4

Reagent additives and their effect on bubble (gas) formation

| Reagent | Description | Redox potential | Bubble (gas) formation inhibition |
|---|---|---|---|
| DTT | Oxidized form | −327 mV | YES* (Oxidized THP) |
| (±)-α-Lipoic acid | Oxidized form | −288 mV | YES* (Oxidized THP) |
| L-Glutathione oxidized (GSSG) | Oxidized form | −230 mV (−259 mV) | NO |
| Coenzyme Q10 | | | NO |
| 2,6 Dichlolorindolphenol sodium salt hydrate (DCPIP) | | +217 mV | NO |
| Phenazine ethosulfate | PES | +55 mV | YES (Oxidized THP) |
| Phenazine methosulfate | PMS | +82 mV | YES |
| 1-Methoxy-5-methylphenazinium | | +63 mV | NO |
| (L)-Dehydroascorbic acid | Oxidized form | −80 mV @ pH 6.43 (pH dependent) | NO |
| α-Thioglycerol | | | NO |
| Methyl Orange (MO) | | +1 V (E0 = +0.961 V vs NHE) | NO |
| Neutral Red (NR) | | Em = −325 mV | NO |
| Evans Blue (EB) | | | NO |
| Nile Blue A (NBA) | | | YES* |
| Methylene Blue (MB) | | | YES (Oxidized THP) |
| Methyl viologen (MV) dichloride | | | NO |
| Erioglaucine | | | YES |

*partial inhibition

FIGS. 7A and 7B show tables of different buffers and their conductivity that may be used in a "bubble free" formulation (BFF) for aqueous droplets. In one example, a bubble free buffer formulation comprises a suitable low conductivity buffer and/or an electron acceptor additive. In one example, a suitable buffer has a conductivity range of about 2.5±0.2 μS/cm to about 5±0.8 μS/cm. In another example, a suitable buffer is selected to have a relatively low conductivity and maintain the biochemical activity of reaction components (e.g., enzymes and other reagent molecules). The table in FIG. 7A is based on Kelly et al, J. Am. Chem. Soc. 2002; 124 (40): 12013-12019; the entirety of which is incorporated herein by reference. The table in FIG. 7B is based on Edman et al, Nucleic Acids Research, 1997; 25 (24): 4907-4914; the entirety of which is incorporated herein by reference.

Example 4. Effect of Buffer Conductivity on Formation of Reactive Molecular Species The methods disclosed herein use low conductivity buffers to substantially reduce or entirely eliminate the formation of reactive molecular species (e.g., ROS and/or hypochlorite) during electrowetting of aqueous droplets on a droplet actuator. Reactive molecular species may be formed during the electrolysis of water in the presence of salts during electrowetting of an aqueous droplet as described hereinabove with reference to FIGS. 1 and 2. Reactive molecular species (e.g., ROS and/or hypochlorite) generated during electrowetting may react with various reagents used in a biochemical reaction. For example, tris(-3 hydroxypropyl)phosphine (THP) and (tris(2-carboxyethyl) phosphine) (TCEP) are reducing agents frequently used in biochemistry and molecular biology applications, such as an SBS reaction. In the presence of ROS or hypochlorite, THP and TCEP may be oxidized and loose activity over time.

Shown below is a colorimetric assay that can be used to detect unreacted (i.e., reduced) THP or TCEP in an aqueous droplet.

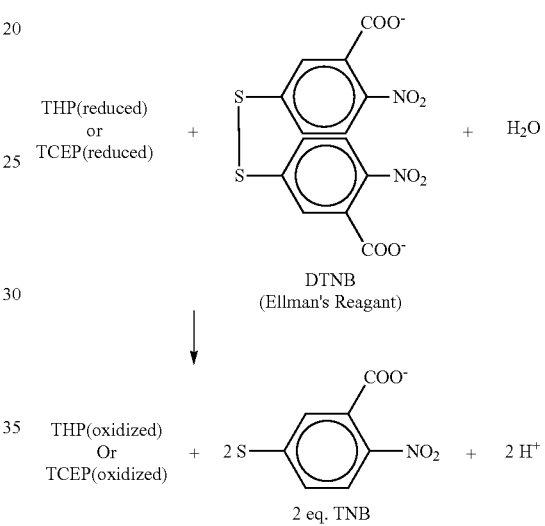

The colorimetric assay used 5,5'-dithio-bis-[2-nitrobenzoic acid] (DTNB or Ellman's reagent) to detect unreacted (i.e., reduced) THP (or TCEP) in an aqueous droplet. THP (or TCEP) reacts with DTNB in a 1:1 ratio to generate 1 molecule of oxidized THP (or TCEP) and 2 equivalents of TNB. The amount of TNB in a droplet is determined by measuring the absorbance of the droplet solution at 412 nm and the concentration calculating from the molar extinction coefficient of TNB (E=14150 $M^{-1}$ $cm^{-1}$ at 412 nm). The amount of TNB in the droplet solution is used to calculate the amount of reduced THP (or TCEP) in the droplet solution.

The type of reactive species (e.g., ROS such as hydrogen peroxide ($H_2O_2$), or hypochlorite ion ($OCl^-$) present in a droplet solution may be determined by adjusting the reaction pH. A pH dependent assay that may be used to determine the type of reactive molecular species present in an aqueous droplet is as follows.

TCEP+OCl−→TCEPoxide+Cl− (constant pH 2 to pH 10), or

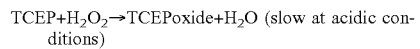
TCEP+$H_2O_2$→TCEPoxide+$H_2O$ (slow at acidic conditions)

In this example, at a low pH (e.g., pH 2 or pH 4.2) the oxidation rate of TCEP by $H_2O_2$ is relatively slow. In contrast, the oxidation of rate TCEP by hypochlorite is independent of pH, i.e., the oxidation of TCEP is constant in a pH range of pH 2 to pH 10.

Figure 8A:
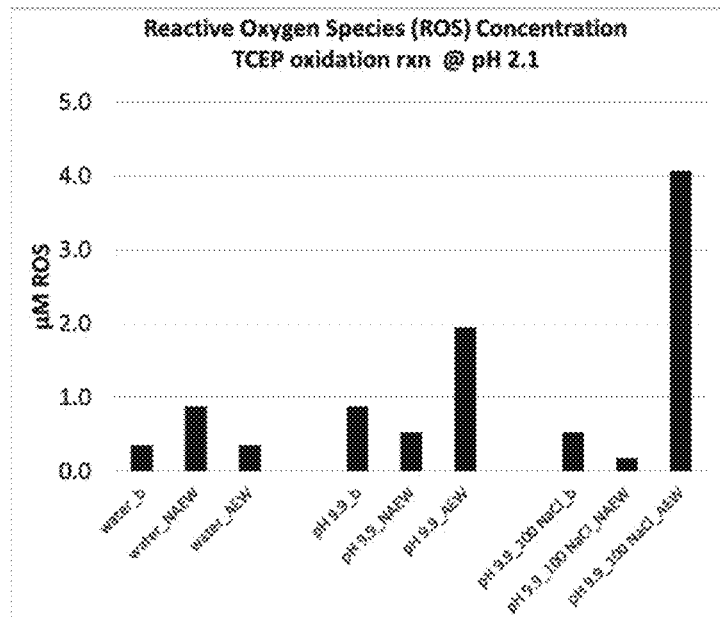
FIGS. 8A and 8B are bar graphs showing (tris(2-carboxyethyl)phosphine) (TCEP) oxidation at pH 2.1 and of TCEP oxidation at pH 8, respectively, by droplet solutions recovered after 2 hours of electrowetting.
Figure 8B:
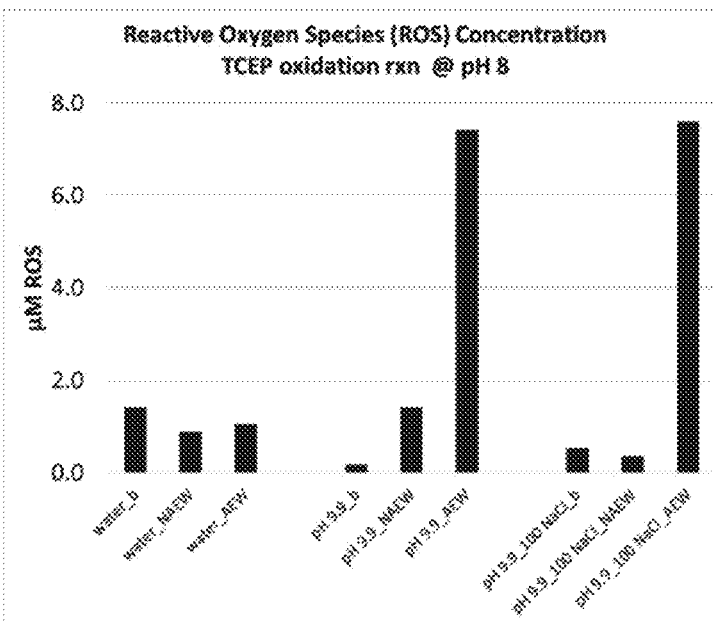

FIGS. 8A and 8B are bar graphs of (tris(2-carboxyethyl) phosphine) (TCEP) oxidation at pH 2.1 and of TCEP oxidation at pH 8, respectively, by droplet solutions recovered after 2 hours of electrowetting. In this example, three different droplet solutions were used: a "water" solution comprising 18 MS2 water and 0.01% Tween® 20; a "pH 9.9" solution comprising 10 mM ethanolamine, 5.5 mM HCL, pH9.9, and 0.01% Tween® 20, and a "pH 9.9_100 NaCl" solution comprising 10 mM ethanolamine, 5.5 mM HCl, pH 9.9, 100 mM NaCl, and 0.01% Tween® 20. Droplet solutions were loaded onto a droplet actuator comprising electrode arrangement 300 of FIG. 3. Individual droplets were dispensed and transported using droplet operations to heating regions 315a-h. The droplets were transported using droplet operations back and forth in a counterclockwise direction within heating regions 315 for a total of 2 hours using the electrowetting parameters described with reference to FIG. 2 (i.e., 300 V, incubation at 70° C., 30 Hz switching frequency, and a 5 sec droplet transport rate). After the 2 hour electrowetting period, droplets were recovered from the droplet actuator. TCEP (0.05 mM) was added to each recovered droplet solution and the amount of TCEP oxidation determined. The amount of TCEP oxidation was then used to calculate the amount of hypochlorite and/or ROS that were present in the recovered droplet solutions.

Referring to FIGS. 8A and 8B, the samples are designated as solution electrowetting condition, wherein the solution is either "water", "pH 9.9", or "pH 9.9_100 NaCl" and the electrowetting condition is either "b" (bench, i.e., the experiment was performed off-actuator), "NAEW" (non-active electrowetting, i.e., droplets that were exposed to filler fluid but were not subjected to active electrowetting), or "AEW" (active electrowetting i.e., droplets that were subjected to active electrowetting).

Referring to FIG. 8A, higher levels of reactive molecular species were detected in actively electrowetted droplet solutions with a higher pH (i.e., pH 9.9_AEW) compared to actively electrowetted droplet solutions with a lower pH (i.e., water_AEW). The data also show that droplet solutions comprising 100 mM NaCl (i.e., pH9.9_100 NaCl_AEW) have higher levels of reactive molecular species compared to droplet solutions without additional NaCl (i.e., pH 9.9_AEW). Because the TCEP oxidation reaction was performed at pH 2.1, the reactive species in the recovered droplet solutions may be identified as hypochlorite.

Referring to FIG. 8B, the rate of TCEP oxidation by all reactive species (i.e., ROS (e.g., hydrogen peroxide, hydroxyl ion, hydroxyl radical, and superoxide anion) and/or hypochlorite) was increased when the reaction was performed at a higher pH (i.e., pH 8). Higher levels of reactive molecular species were detected in actively electrowetted droplet solutions with a higher pH (i.e., pH 9.9_AEW) compared to actively electrowetted droplet solutions with a lower pH (i.e., water_AEW).

Figure 9:
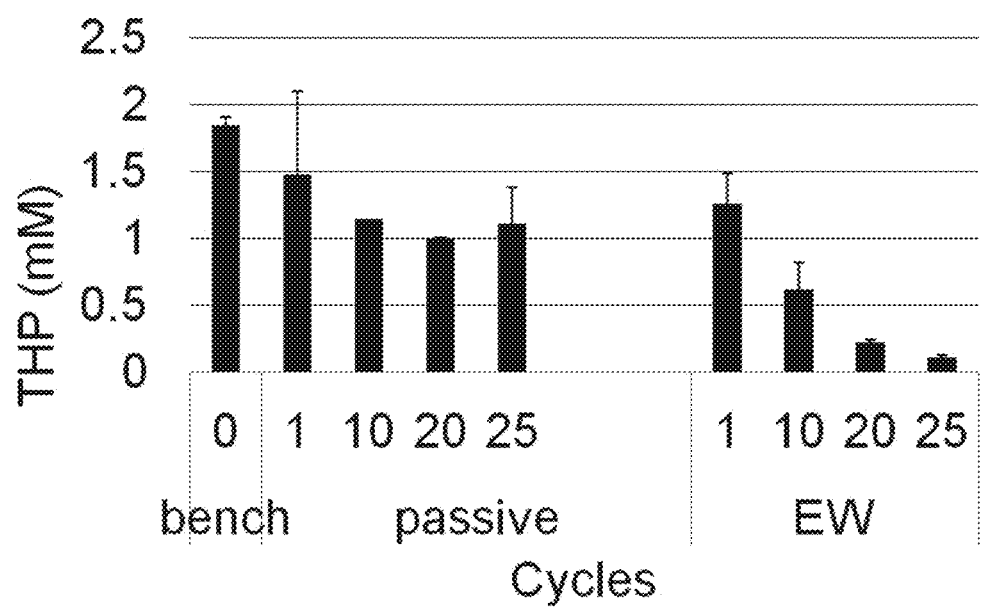
FIG. 9 is a bar graph showing the effect of droplet electrowetting on tris(-3hydroxypropyl)phosphine (THP) degradation.

FIG. 9 is a bar graph showing of the effect of droplet electrowetting on THP degradation. THP is a reducing agent used in dye cleavage and nucleotide deblocking reactions during SBS. In this example, the sample droplet solution is a dye cleavage solution comprising 2 mM THP, 0.2 mM ascorbate, 5 mM Tris-HCl pH 7.5, 1 M NaCl, 0.5 mM EDTA, and 0.01% Tween® 20. Three different incubation conditions were used: an on "bench" control where the droplet solution was not exposed to filler fluid or a droplet actuator, "passive" where the droplet solution was exposed to filler fluid on a droplet actuator inlet port but did not undergo active electrowetting, and "EW" where the droplet solution was exposed to active electrowetting. The passive and EW sample solutions were loaded onto a droplet actuator comprising electrode arrangement 300 of FIG. 3. The electrowetting parameters were 70° C., 30 Hz switching frequency, and a 5 second droplet transport rate. The droplet size was 16 DU. Individual sample droplets were dispensed and transported using droplet operations to heating regions 315. For the actively electrowetted samples, the droplets were transported using droplet operations back and forth in a counterclockwise direction within heating regions 315 for 1, 10, 20, and 25 transport cycles. Sample droplets were recovered from the droplet actuator and the amount of unreacted (i.e., reduced) THP in the recovered sample droplets was determined using the colorimetric assay described above. The data show that in the absence of active electrowetting (i.e., "passive" incubation on a droplet actuator), about one-half of the THP in the droplet solutions was lost over time (i.e., 20 and 25 "passive" cycles). The loss of THP in the "passive" condition may represent diffusion of THP into the filler fluid over time. The data also show that the loss of unreacted THP in droplets that were exposed to active electrowetting ("EW) was accelerated; at the end of 25 cycles of active electrowetting most (about 95%) of the THP in the droplet solution has been degraded or oxidized.

Figure 10:
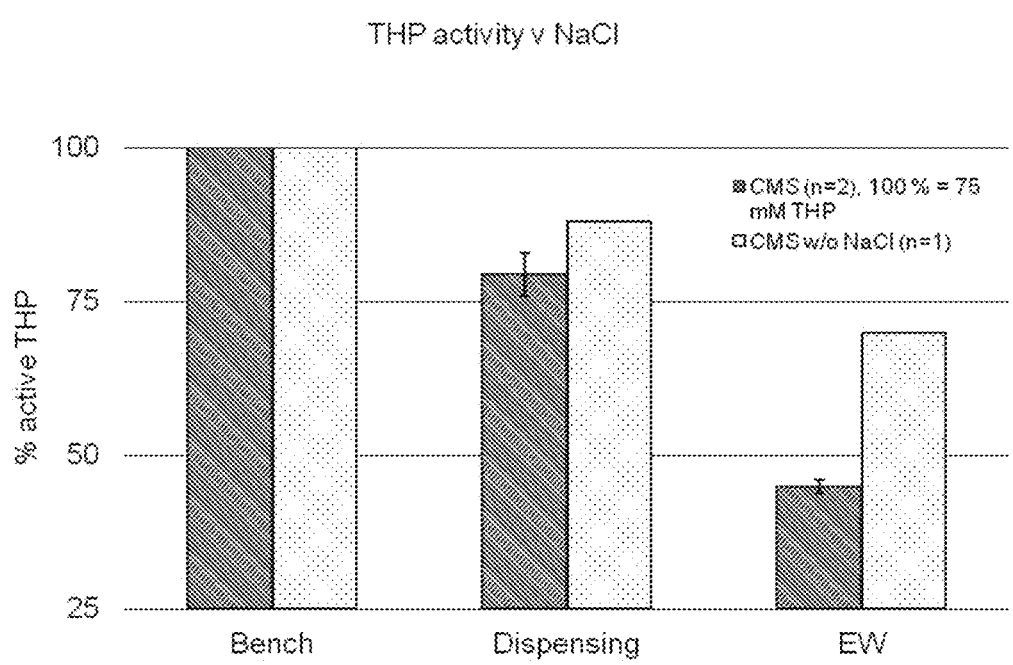
FIG. 10 is a bar graph showing the effect of NaCl on THP activity loss in a sequencing-by-synthesis (SBS) deblocking solution exposed to active electrowetting.

FIG. 10 is a bar graph showing the effect of NaCl on THP activity loss in an SBS deblocking solution exposed to active electrowetting. In this example, two different THP solutions were used: a first high conductivity THP solution comprising 100 mM THP, 100 mM ethanolamine pH 9.9, 10 mM ascorbate, 1 M NaCl, and 0.05% Tween® 20, and a second lower conductivity THP solution without the addition of 1 M NaCl. Three different incubation conditions were used: an on "bench" control where the droplet solution was not exposed to filler fluid or a droplet actuator, "dispensing" where the droplet solution was exposed to filler fluid in a dispensing reservoir on a droplet actuator but did not undergo active electrowetting, and "EW" where the droplet solution was exposed to active electrowetting. The sample solution was loaded onto a droplet actuator comprising electrode arrangement 300 of FIG. 3. The electrowetting parameters were 70° C., 30 Hz switching frequency, and a 5 second droplet transport rate. The droplet size was 16 DU. For the EW sample droplets, individual sample droplets were dispensed and transported using droplet operations to heating regions 315. The sample droplets were transported using droplet operations back and forth in a counterclockwise direction within heating regions 315 for 25 transport cycles (57 minutes). Sample droplets were recovered from the droplet actuator and the amount of active THP in the recovered sample droplets was determined using the colorimetric assay described above. The data show that the percentage of active THP is higher in recovered sample droplets comprising THP solution without NaCl compared to the level of active THP in recovered sample droplets comprising the high conductivity THP solution that includes 1 M NaCl.

Figure 11:
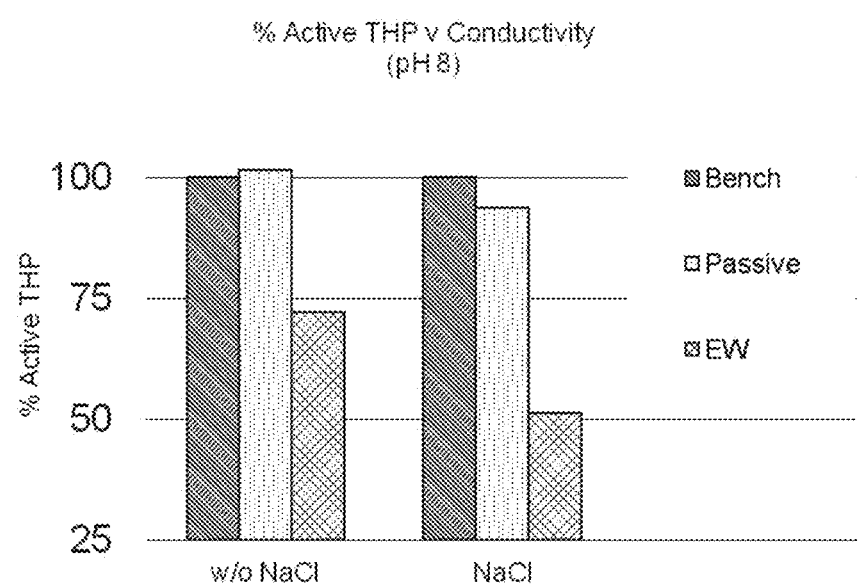
FIG. 11 is a bar graph showing the effect of reducing buffer ionic strength on THP activity in droplets exposed to active electrowetting.

FIG. 11 is a bar graph showing the effect of reducing buffer ionic strength on THP activity in droplets exposed to active electrowetting. In this example, two different THP solutions were used: a first high conductivity THP solution (designated "NaCl") comprising 2 mM THP, 0.2 mM ascorbate, 5 mM Tris-HCl pH 8, 1M NaCl, 0.5 mM EDTA, and 0.01% Tween® 20, and a second lower conductivity THP solution without the addition of 1 M NaCl (designated "w/o NaCl"). Three different incubation conditions were used: an on "bench" control where the droplet solution was not exposed to filler fluid or a droplet actuator, "passive" where the droplet solution was exposed to filler fluid in a droplet actuator but did not undergo active electrowetting, and "EW" where the droplet solution was exposed to active electrowetting. The passive and EW sample solutions were loaded onto a droplet actuator comprising electrode arrangement 300 of FIG. 3. The electrowetting parameters were 70° C., 30 Hz switching frequency, and a 5 second droplet transport rate. The droplet size was 16 DU. Individual sample droplets were dispensed and transported using droplet operations to heating regions 315. For the actively electrowetted samples (EW), the droplets were transported using droplet operations back and forth in a counterclockwise direction within heating regions 315 for 10 transport cycles. Sample droplets were recovered from the droplet actuator and the amount of active THP in the recovered sample droplets was determined using the colorimetric assay described above. The data show that the percentage of active THP is higher in recovered sample droplets comprising THP solution without NaCl (i.e., a lower conductivity buffer) compared to the level of active THP in recovered sample droplets comprising the higher conductivity THP solution that includes 1 M NaCl. Decreasing the ionic strength of the THP buffer reduced THP activity loss.

Figure 12:
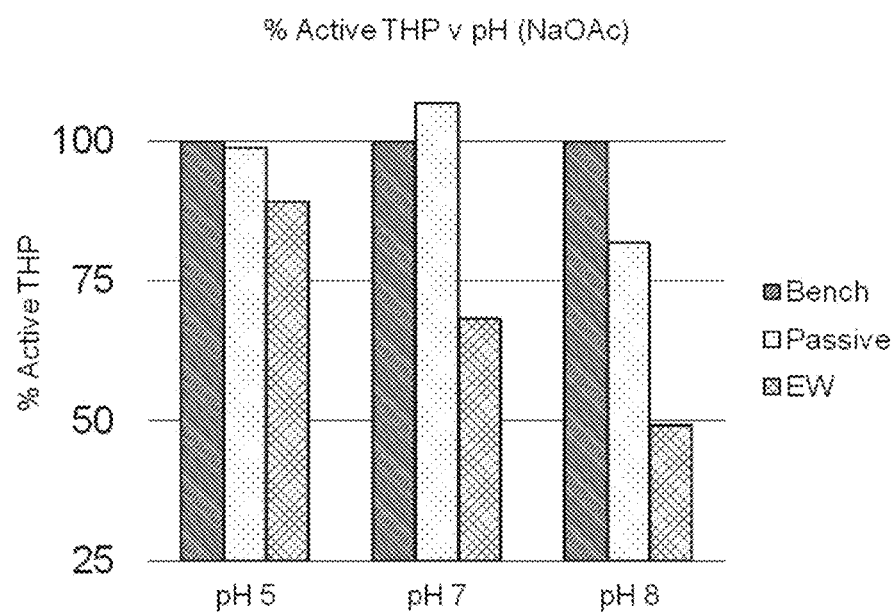
FIG. 12 is a bar graph showing the effect of lowering buffer pH on THP activity in droplets exposed to active electrowetting.

FIG. 12 is a bar graph showing the effect of reducing buffer pH on THP activity in droplets exposed to active electrowetting. In this example, three THP solutions comprising 2 mM THP, 0.2 mM ascorbate, 5 mM Tris-HCl, 1M NaOAc, 0.5 mM EDTA, and 0.01% Tween® 20 were used: a first THP solution at pH 5 (i.e., 5 mM Tris-HCl pH 5), a second THP solution at pH 7 (i.e., 5 mM Tris-HCl pH 7), and a third THP solution at pH 8 (i.e., 5 mM Tris-HCl pH 8). The incubation conditions, electrowetting parameters and determination of THP activity were as described with reference to FIG. 17. The data showed that reducing the pH of the THP solution from pH 8 to pH 5 reduces THP activity loss.

Example 5. Modification of Electrowetting Parameters to Reduce Bubble Formation

Figure 13:
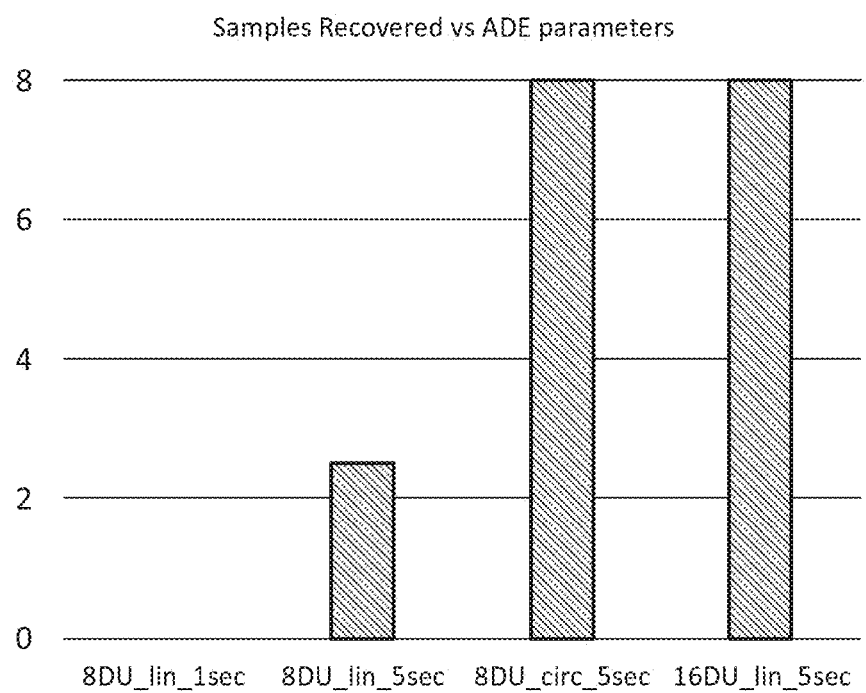
FIG. 13 is a bar graph showing the number of samples recovered as a function of droplet electrowetting parameters.

FIG. 13 is a bar graph showing of the number of samples recovered as a function of droplet electrowetting parameters. The number of samples recovered from a droplet actuator after active electrowetting of droplets is used as an indicator of bubble formation, i.e., the presence of a substantial number of bubbles interferes with droplet recovery. In this example, a droplet solution was loaded onto a droplet actuator comprising electrode arrangement 300 of FIG. 3. Electrode arrangement 300 comprises 8 sample lanes (n=8). In this example, each bar in the graph represents an experiment performed (n=8 samples) using a different set of electrowetting parameters. The electrowetting parameters that were varied between experiments are designated by "droplet size ("digital unit" (DU)_electrode exposure_droplet transport rate". For example, a set of electrowetting parameters labeled "8DU_lin_1 sec" designates transport of an 8 DU size droplet in a linear motion (i.e., back and forth in a liner direction) at a 1 second transport rate. A set of electrowetting parameters labeled "8DU_circ_5 sec" designates transport of an 8 DU size droplet in a counterclockwise circular motion at a 5 second transport rate. All experiments were performed using an activation voltage of 300V, a switching frequency of 30 Hz, a temperature of 70° C., and a total electrowetting time of 1 hour. The data show that increasing the droplet transport rate (e.g., reducing the transport time over the same distance) from 5 seconds (i.e., 8DU_circ_5 sec or 16DU_lin_5 sec) to 1 second (i.e., 8DU_lin_1 sec) substantially reduces the number of samples that are recovered from a droplet actuator after electrowetting. The data also show the number of samples recovered after electrowetting is substantially higher for samples that were transport in a counterclockwise (circular) direction (i.e., 8DU_circ_5 sec) compared to samples transported in a linear direction (i.e., 8DU_lin_5 sec).

Figure 14A:
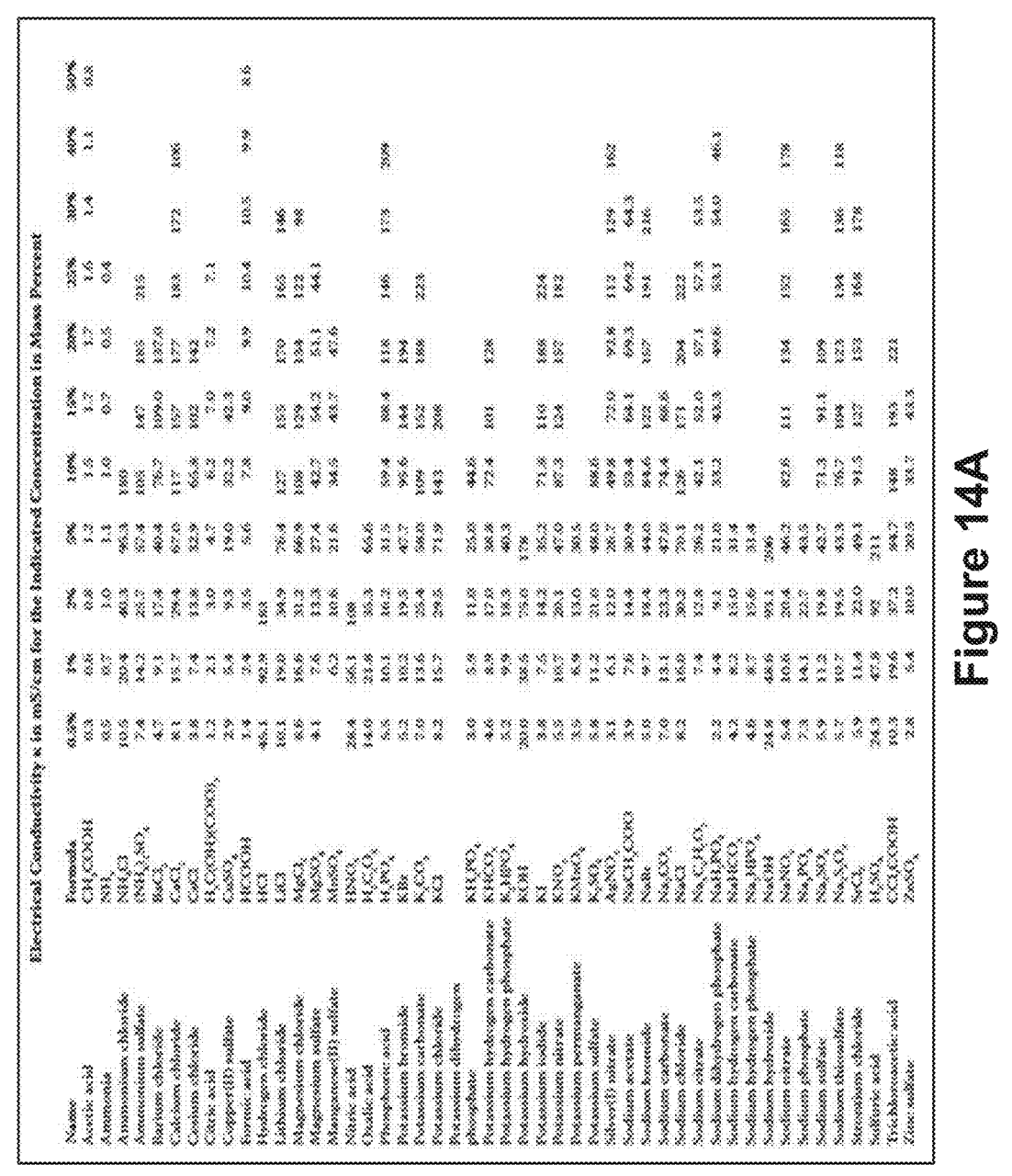

FIGS. 14A and 14B shows tables of lists of potential salt solutions that may be used in the formulation of reaction buffers suitable for use in digital microfluidic applications, e.g., biochemical reactions performed on a droplet actuator. The table in FIG. 14A is based on (1) CRC Handbook of Chemistry, and Physics, 70th Edition, Weast, R. C., Ed., CRC Press, Boca Raton, Fla., 1989 and (2) Wolf, A. V., Aqueous Solutions and Body Fluids, Harper and Row, New York, 1966; the entireties of which are incorporated herein by reference. The table in FIG. 14B is based on Kelly et al, J. Am. Chem. Soc. 2002; 124 (40): 12013-12019; the entirety of which is incorporated herein by reference.

Example 6. Reducing Gas Bubble Formation During NuPCR

During a DNA amplification reaction (e.g., a NuPCR reaction (Illumina, Inc.) performed in aqueous droplets on a droplet actuator, gas bubbles may be formed. One consequence of the generation of bubbles during electrowetting of droplets in a DNA amplification reaction is sample loss. The present disclosure provides methods of substantially reducing or eliminating the generation of gas bubbles during a DNA amplification reaction performed in aqueous droplets on a droplet actuator.

Tests were performed with respect to bubble formation. For example, an evaluation was performed (hereafter called test #1) with respect to bubble formation during electrowetting of droplets comprising a standard PCR buffer. Additionally, an evaluation was performed (hereafter called test #2) with respect to bubble formation during electrowetting of droplets comprising a modified PCR buffer. The formulation of the standard PCR buffer was 25 mM KCl, 50 mM Tris-HCl pH 8.5, and 8 mM $MgCl_2$. The formulation of the modified PCR buffer was 50 mM TrisOAc pH 8.5 and 8 mM $MgSO_4$. In this example, droplet solutions comprising the standard PCR buffer or the modified PCR buffer were loaded onto a droplet actuator comprising electrode arrangement 300 of FIG. 4. Eight individual droplets (n=8) were dispensed and transported using droplet operations to heating regions 315. The droplets were transported using droplet operations back and forth in a linear direction into and out of heating regions 315 over 3 heater bars. The electrowetting parameters were 92° C., 1 hour, 100V, 1.5-10 second incubation. The electrowetting protocol was NuPCR_8DU_slug_30 Hz_100V_92C_30i_lin.ade. The data show that a substantial number of bubbles were generated during electrowetting of droplets comprising the standard PCR buffer containing 25 mM KCl, 50 mM Tris-HCl pH 8.5, and 8 mM $MgCl_2$ (FIG. 10A). By contrast, eliminating KCl and chloride and replacing the buffer components with 50 mM TrisOAc pH 8.5 and 8 mM MgSO$_4$ in the modified PCR buffer substantially reduces bubble formation during electrowetting.

Figure 15:
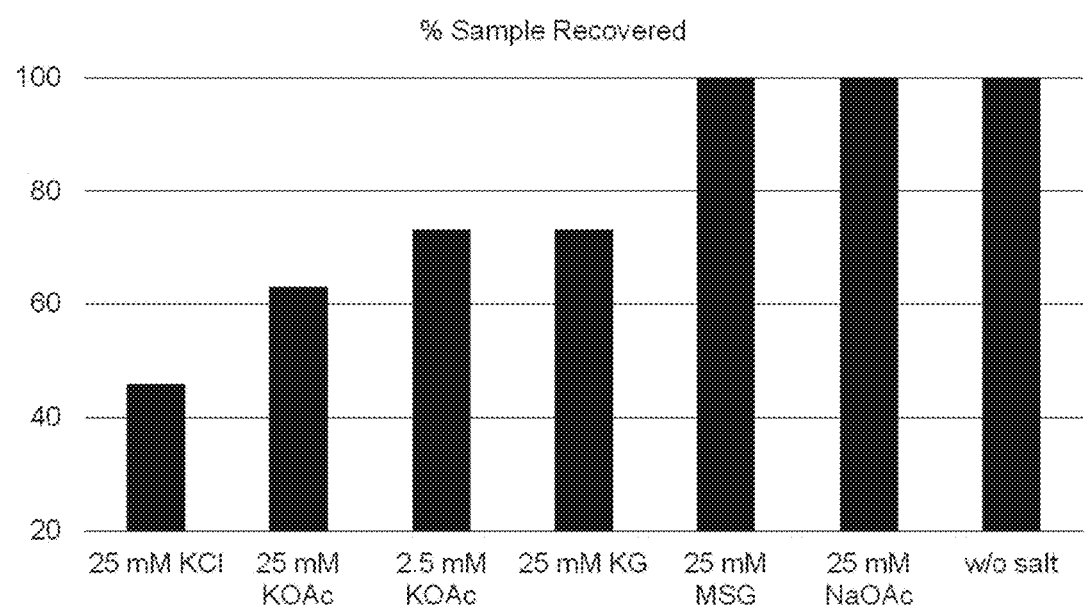
FIG. 15 is a bar graph showing sample recovery after electrowetting of sample droplets comprising different (lower conductivity) salt solutions.

FIG. 15 is a bar graph showing sample recovery after electrowetting of sample droplets comprising different (lower conductivity) salt solutions. The different salt solutions were 25 mM potassium acetate (KOAc), 2.5 mM KOAc, 25 mM potassium glutamate (KG), 25 mM monosodium glutamate (MSG), and 25 mM acetate (NaOAc). Buffers comprising 25 mM KCl (a high conductivity buffer) and no salt (w/o salt) were used as control samples. The droplet actuator and electrowetting parameters were as described above with reference to test #1 and test #2. The data show that as the sample buffer conductivity is decreased (e.g., from 25 mM KCl to 25 mM NaOAc), the percent sample recovery is increased. In one example, referring to FIG. 20A, a 0.5% w/v KCl has a conductivity of 8.2 mS/cm and a 0.5% w/v NaOAc has a conductivity of 3.9 mS/cm. The conductivity of a buffer may be reduced, for example, by using lower mobility ions (e.g., NaOAc) and/or by reducing the salt concentration (25 mM KOAc vs 2.5 mM KOAc).

Figure 16:
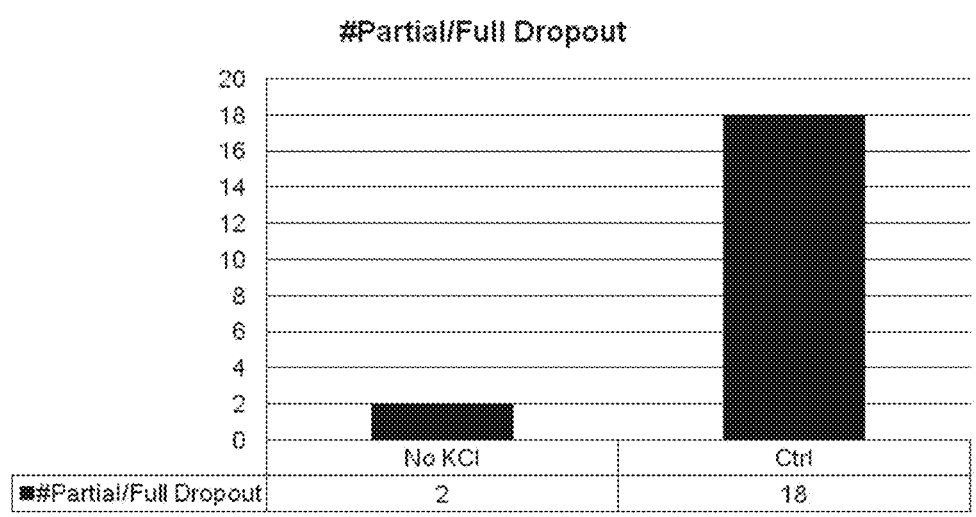
FIG. 16 is a bar graph showing the number of partial and full sample dropouts (lost samples) in a NuPCR reaction after electrowetting of sample droplets comprising a KCl-free buffer formulation.

FIG. 16 is a bar graph showing the number of partial and full sample dropouts (lost samples) in a NuPCR reaction after electrowetting of sample droplets comprising a KCl-free buffer formulation. A total of 208 samples comprising a KCl-free buffer were electrowetted on 8 droplet actuator cartridges and scored manually for sample dropout. A buffer solution comprising 25 mM KCl was used as a control. The electrowetting parameters were 92° C., 1 h, 100 V, 1.5-10 sec incubation. Full sample dropout is defined as complete sample loss over the time course of the experiment. Partial sample dropout is defined as a substantial decrease in the number of digital units (droplets) that were visually detected. The number of partial/full dropouts in the KCl-free buffer samples was 2 (0.98%) compared to 18 partial/full dropouts in the control samples. Videos of the electrowetting operations also confirmed that the formation of bubbles and the fraction of immobile bubbles were substantially reduced during electrowetting of droplets comprising the KCl-free buffer solution compared to the control samples. Mobile bubbles readily migrated to the vent port on the droplet actuator and were released.

Several PCR reaction conditions were evaluated to identify parameters that reduce bubble formation and improve sample recovery while maintaining the efficiency of a DNA amplification reaction (e.g., enzymatic activity in a NuPCR reaction).

Table 5 below shows data of the amplification metrics from a NuPCR experiment performed using different buffer formulations comprising potassium or sodium salts. The different buffer formulations evaluated were KCl_MgSO4_TrisOAc, MSG_MgSO4_TrisOAc, NaO_AcMgSO4_TrisOAc, and NoKCl_MgSO4_TrisOAc. The droplet actuator and electrowetting parameters were as described above with reference to test #1 and test #2. The data show that PCR amplification using buffers comprising Na (i.e., MSG_MgSO4_TrisOAc and NaOAc_MgSO4_TrisOAc buffers) or no KCL (i.e., NoKCl_MgSO4_TrisOAc) have a higher percentage of sample recovery (% Recovered) compared to a control buffer comprising 25 mM KCl. The data also show that the PCR efficiency was lower for amplification reactions using buffers comprising Na compared to control and KCl_MgSO4_TrisOAc buffers.

TABLE 5

Data of the amplification metrics from a NuPCR experiment performed using different buffer formulations comprising potassium or sodium salts

| Condition | Ctrl | KCl_MgSO4_TrisOAc | MSG_MgSO4_TrisOAc | NaOAc_MgSO4_TrisOAc | NoKCl_MgSO4_TrisOAc |
|---|---|---|---|---|---|
| Salt1 (K or replacement) | KCl | KCl | MSG | NaOAc | NoKC |
| Salt1 Final Conc | 25 mM | 25 mM | 25 mM | 25 mM | 0 mM |
| Salt2 (Mg Salt) | MgCl2 | MgSO4 | MgSO4 | MgSO4 | MgSO4 |
| Salt2 Final Conc | 8 mM | 8 mM | 8 mM | 8 mM | 8 mM |
| Tris pH 8.5 | TrisHCl | TrisOAc | TrisOAc | TrisOAc | TrisOAc |
| Tris Final Conc | 50 mM | 50 mM | 50 mM | 50 mM | 50 mM |
| % Recovered | 45% | NA | 100% | 100% | 100% |
| PCR Efficiency | 100% | 102% | 93% | 85% | 90% |
| Slope | −3.33 | −3.28 | −3.49 | −3.74 | −5.59 |
| Y intercept | 21.141 | 21.975 | 23.906 | 24.764 | 22.83 |
| R Squared | 0.9988 | 0.9948 | 0.9804 | 0.9928 | 0.9970 |
| 100 pM | 14.40 | 15.57 | 17.16 | 17.47 | 15.82 |
| 33.33 pM | 16.16 | 16.69 | 18.11 | 18.84 | 17.25 |
| 11.11 pM | 17.75 | 18.63 | 20.29 | 20.99 | 18.90 |
| 3.7 pM | 19.16 | 20.21 | 22.39 | 22.35 | 20.77 |
| 1.23 pM | 20.85 | 21.64 | 23.35 | 24.63 | 22.64 |
| CT Sample | 15.6 | 15.7 | 18.1 | 18.7 | 16.9 |
| CT Sample Rep | 14.7 | 16.4 | 17.5 | 17.7 | 18.0 |

Table 6 below shows data of the amplification metrics from a NuPCR experiment performed on a droplet actuator using buffers comprising different concentrations of potassium salts (i.e., KOAc or KCl). The cycling parameters were 92° C. for 1 minute, then 92° C. for 10 seconds, 50° C. for 30 seconds, and 72° C. for 30 seconds, for 25 cycles with detection after each 50° C. step. The data show that as the concentration of KCl is decreased 100-fold from 25 mM KCl to 0.25 mM KCl, the PCR efficiency remains about the same, enzymatic activity is maintained.

TABLE 6

Data of the amplification metrics from a NuPCR experiment performed on a droplet actuator using buffers comprising different concentrations of potassium salts (i.e., KOAc or KCl)

| Condition | 1 | 2 | 3 | 4 | 5 | 6 | 7 | 8 |
|---|---|---|---|---|---|---|---|---|
| Salt1 (K or replacement) | MSG | MSG | KOAc | KOAc | KOAc | KCl | KCl | KCl |
| Salt1 Final Conc | 25 mM | 25 mM | 0.25 mM | 2.5 mM | 25 mM | 0.25 mM | 2.5 mM | 25 mM |
| Salt2 (Mg Salt) | MgSO4 | MgCl2 | MgSO4 | MgSO4 | MgSO4 | MgSO4 | MgSO4 | MgSO4 |
| Salt2 Final Conc | 8 mM | 8 mM | 8 mM | 8 mM | 8 mM | 8 mM | 8 mM | 8 mM |
| Tris pH 8.5 | TrisOAc | TrisHCl | TrisOAc | TrisOAc | TrisOAc | TrisOAc | TrisOAc | TrisOAc |
| Tris Final Conc | 50 mM | 50 mM | 50 mM | 50 mM | 50 mM | 50 mM | 50 mM | 50 mM |
| *PCR Efficiency* | *80%* | *83%* | *93%* | *95%* | *79%* | *103%* | *99%* | *96%* |
| Slope | −3.93 | −3.82 | −3.51 | −3.45 | −3.95 | −3.24 | −3.34 | −3.42 |
| Y intercept | 23.53 | 21.41 | 21.40 | 22.69 | 24.56 | 21.24 | 21.87 | 22.00 |
| R Squared | 0.9998 | 0.9953 | 0.9938 | 0.9908 | 0.9926 | 0.9985 | 0.9956 | 0.9919 |
| 100 pM | 15.7 | 13.7 | 14.2 | 15.9 | 16.5 | 14.8 | 15.2 | 15.2 |
| 33.33 DM | 17.5 | 15.7 | 16.2 | 17.4 | 18.6 | 16.3 | 16.9 | 16.6 |
| 11.11 DM | 19.4 | 17.5 | 17.8 | 19.2 | 20.6 | 17.7 | 18.1 | 18.6 |
| 3.7 DM | 21.4 | 18.9 | 19.7 | 20.3 | 22.6 | 19.4 | 20.0 | 20.4 |
| 1.23 pM | 23.2 | 21.3 | 20.8 | 22.6 | 23.9 | 21.0 | 21.6 | 21.4 |
| CT Sample | 17.3 | 15.2 | 15.2 | 17.0 | 18.9 | 15.8 | 15.7 | 16.5 |
| CT Sample Rep | 17.2 | 15.1 | 15.5 | 16.9 | 19.0 | 15.7 | 16.2 | 15.7 |

Figure 17:
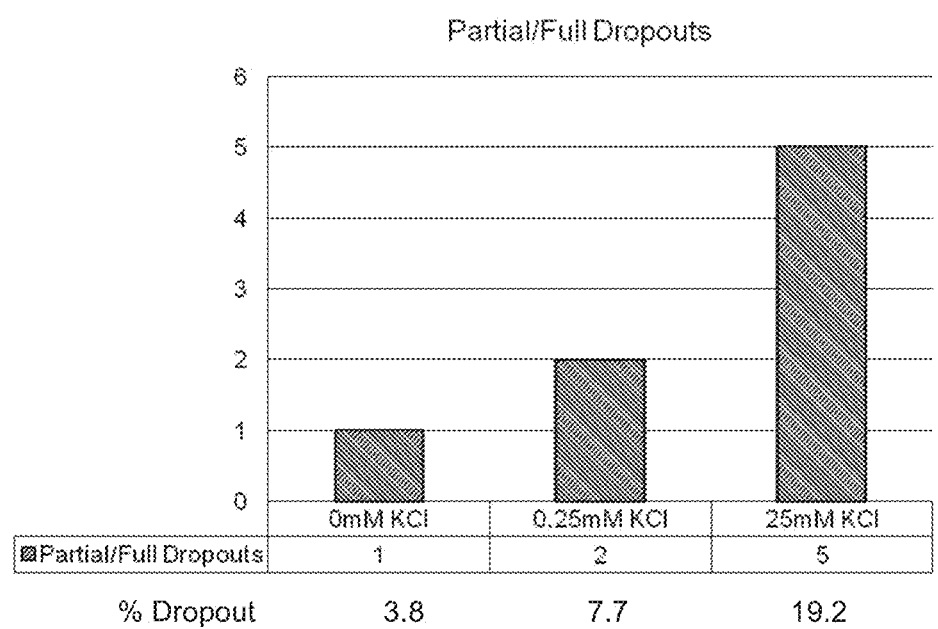
FIG. 17 is a bar graph showing the number of partial and full sample dropouts in NuPCR reactions after electrowetting of sample droplets comprising different concentrations of KCl.

FIG. 17 is a bar graph showing the number of partial and full sample dropouts in NuPCR reactions after electrowetting of sample droplets comprising different concentrations of KCl. The concentrations of KCl in the PCR buffer were 0, 0.25, and 25 mM. The PCR buffer 50 mM TrisHCl pH 8.5, 8 mM $MgCl_2$, 100 mM Trehalose, 4% w/v PEG 8000, 0.25 mg/mL BSA, 1% w/v Glcyerol, 0.2 mM dNTP, 0.02% w/v ProClin, 0.06 U/uL AptaTaq, 0.00375% w/v Detergent N, and 0.005% w/v Blu dye. The total number of samples evaluated for each buffer formulation was 26 (n=26). The cycling parameters were 92° C. for 1 minute, then 92° C. for 10 seconds, 50° C. for 30 seconds, and 72° C. for 30 seconds, for 25 cycles with detection after each 50° C. step. The data show that decreasing the KCl concentration from 25 mM KCl to 0.25 mM reduced sample dropout from 19.2% to 7.7%. Decreasing the KCl concentration to 0 mM, further reduced the sample dropout to 3.8%.

Table 7 below shows data of the of the amplification metrics from the NuPCR experiment of FIG. 17. The PCR efficiency for the 0 mM KCl buffer formulation was 0.92. The PCR efficiency for the 0.25 mM KCl buffer formulation was 0.98. The Ct values (threshold cycle) are higher for the 25 mM KCl samples (about 17) compared to the Ct values for the 0.25 mM KCl (about 15) and the 0 mM KCl (about 15) samples. A difference of about 2 Ct values indicates a decrease in DNA yield (about a factor of 4) at each cycle in the 25 mM KCl samples compared to samples comprising lower concentrations of KCl.

TABLE 7

Data of the amplification metrics from the NuPCR experiment of FIG. 17

| | Lane | 0 mM KCL | 0.25 mM KCl | 25 mM KCl |
|---|---|---|---|---|
| Left | 1 | 15.53 | 15.31 | 16.80 |
| | 2 | 15.60 | 15.44 | 16.81 |
| | 3 | 15.56 | 15.51 | |
| | 4 | 15.73 | 15.50 | 16.85 |
| | 5 | 15.54 | 15.49 | 16.81 |
| | 6 | 15.77 | 15.48 | 16.85 |
| | 7 | 15.74 | 15.25 | 16.87 |
| | 8 | 15.00 | 15.00 | 16.00£ |

TABLE 7-continued

Data of the amplification metrics from the NuPCR experiment of FIG. 17

| | Lane | 0 mM KCL | 0.25 mM KCl | 25 mM KCl |
|---|---|---|---|---|
| | Average | 15.56 | 15.37 | 16.71 |
| | StDev | 0.25 | 0.18 | 0.32 |
| | CV | 1.6% | 1.2% | 1.9% |
| Right | 9 | 15.41 | 15.30 | 16.97 |
| | 10 | 15.62 | 15.40 | 17.36 |
| | 11 | 15.59 | 15.47 | 17.24 |
| | 12 | 15.69 | 15.57 | 17.51 |
| | 13 | 15.53 | 15.48 | 17.63 |
| | 14 | 15.69 | 15.40 | 17.46 |
| | 15 | 15.51 | | 17.08 |
| | 16 | 15.42 | 15.37 | 16.95 |
| | Average | 15.56 | 15.43 | 17.27 |
| | StDev | 0.11 | 0.09 | 0.26 |
| | CV | 0.7% | 0.6% | 1.5% |
| Standard (Average of sides) | 100 pM | 14.14 | 13.47 | 15.74 |
| | 33.33 pM | 16.39 | 15.91 | 16.98 |
| | 11.11 pM | 18.38 | 17.52 | |
| | 3.7 pM | 19.77 | | 19.89 |
| | 1.23 pM | 20.86 | 20.10 | 21.63 |
| | Y | 21.59 | 20.68 | 21.78 |
| | Slope | −3.52 | −3.37 | −3.08 |
| | Efficiency | 0.92 | 0.98 | 1.11 |

Table 8 below shows data of the amplification metrics from a NuPCR experiment performed on a droplet actuator using a sample buffer comprising 0.25 mM KCl. The experiment was performed on 6 droplet actuators for a total sample size of 156 (n=156). The total number of dropouts detected was 4 (i.e., a 2.6% dropout rate) and the PCR efficiency range was maintained at 0.98-1.07.

TABLE 8

Data of the amplification metrics from a NuPCR experiment performed on a droplet actuator using a sample buffer comprising 0.25 mM KCl.

| | Lane | 0.25 mM KCl | 0.25 mM KCl | 0.25 mM KCl | 0.25 mM KCl | 0.25 mM KCl | 0.25 mM KCl |
|---|---|---|---|---|---|---|---|
| Left | 1 | 15.31 | 15.74 | 16.13 | 15.93 | 15.84 | 15.86 |
| | 2 | 15.44 | 15.93 | 16.26 | 15.76 | 15.91 | 15.91 |
| | 3 | 15.51 | 16.37 | 16.15 | 19.12 | 16.09 | 16.04 |
| | 4 | 15.50 | 15.99 | 16.34 | 15.86 | 15.88 | 15.93 |
| | 5 | 15.49 | 16.24 | 16.13 | 16.12 | 15.86 | 15.92 |
| | 6 | 15.48 | 16.32 | 16.13 | 15.82 | 16.00 | 15.77 |
| | 7 | 15.25 | 16.24 | 15.88 | 15.83 | 15.88 | 15.79 |
| | 8 | 15.00 | 15.00 | Lost | 15.00 | 15.00 | 15.00 |
| | Average | 15.37 | 15.98 | 16.14 | 16.18 | 15.81 | 15.78 |
| | StDev | 0.18 | 0.45 | 0.14 | 1.23 | 0.34 | 0.32 |
| | CV | 1.2% | 2.8% | 0.9% | 7.6% | 2.1% | 2.1% |
| Right | 9 | 15.30 | 15.57 | 15.74 | 15.67 | 15.84 | 15.74 |
| | 10 | 15.40 | 15.93 | 16.72 | 16.11 | 15.91 | 15.89 |
| | 11 | 15.47 | 16.13 | CT Issue | 15.83 | Lost | 16.80 |
| | 12 | 15.57 | 15.97 | 15.66 | 15.82 | 16.01 | 16.07 |
| | 13 | 15.48 | 15.93 | 15.84 | 15.77 | 16.07 | 16.16 |
| | 14 | 15.40 | 15.84 | 15.78 | 15.77 | 15.99 | 15.60 |
| | 15 | Lost | 15.84 | 15.81 | 15.94 | 16.04 | 16.04 |
| | 16 | 15.37 | 15.61 | 15.72 | 15.78 | 15.82 | 15.93 |
| | Average | 15.43 | 15.85 | 15.90 | 15.84 | 15.95 | 16.03 |
| | StDev | 0.09 | 0.19 | 0.37 | 0.14 | 0.10 | 0.36 |
| | CV | 0.6% | 1.2% | 2.3% | 0.9% | 0.6% | 2.2% |
| Standard (Average of sides) | 100 pM | 13.47 | 14.76 | 14.63 | 15.15 | 14.73 | 14.54 |
| | 33.33 pM | 15.91 | 16.02 | 17.44 | 17.74 | 16.74 | 16.60 |
| | 11.11 pM | 17.52 | Dispense | 19.94 | 19.05 | 18.41 | 18.06 |
| | 3.7 pM | Lost | 19.76 | 20.54 | 21.06 | 19.59 | 19.69 |
| | 1.23 pM | 20.10 | 20.61 | 21.03 | 21.08 | 20.85 | 20.90 |
| | Y | 20.68 | 21.16 | 22.20 | 22.14 | 21.37 | 21.42 |
| | Slope | −3.37 | −3.23 | −3.33 | −3.18 | −3.16 | −3.31 |
| | Efficiency | 0.98 | 1.04 | 1.00 | 1.06 | 1.07 | 1.00 |

Figure 18:
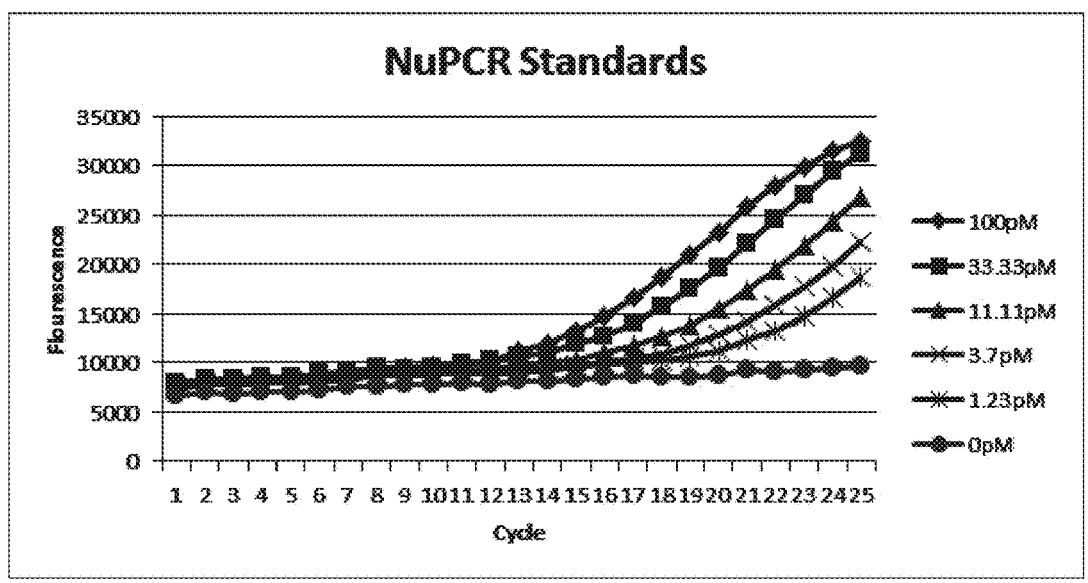
FIG. 18 is a plot of the raw readout for the amplification metrics from a NuPCR experiment performed on a droplet actuator using a sample buffer comprising 0.25 mM KCl.

FIG. 18 is a plot showing the raw readout for amplification of the NuPCR standards shown in Table 8.

Table 9 below shows a summary of examples of aqueous buffer formulations that were evaluated for their efficacy in reducing gas bubble generation and/or improving PCR efficiency.

TABLE 9

Summary of examples of aqueous buffer formulations that were evaluated for their efficacy in reducing gas bubble generation and/or improving PCR efficiency

| Test | Details | Outcome |
|---|---|---|
| Replace TrisHCl with TrisOAc | Same concentrations swap | Equal PCR efficiency |
| Replace MgCl2 with MgSO4 | Same concentrations swap | Equal PCR efficiency |
| Titrate KCl | 0, 0.125, 0.25, 2.5, 25 mM | Best PCR efficiency performance is 0.25, 2.5, 25 mM. Least bubbles with 0, 0.125, 25 mM. |
| Titrate KOAc | 0.25, 2.5, 25 mM | Best efficiency with 2.5 mM. 0.25 nM and 25 mM has unacceptable efficiency. Too many bubbles even at 2.5 mM. |
| NaOAc | Same concentrations swap | No bubbles but low efficiency |
| Na glutamate | Same concentrations swap | No bubbles but low efficiency |
| Add Propylene Glycol to 25 mM KCl | 1M and 2.5M | Did not reduce bubbles |
| Add 1-thioglycerol to 25 mM KCl | 5% | Did not reduce bubbles |
| NH4SO4 | Same concentrations swap | Killed PCR |

Example 6. Effect of Active Electrowetting on THP and TCEP

Reactive molecular species (e.g., ROS and/or hypochlorite) generated during electrowetting may react with various reagents used in a biochemical reaction. For example, tris(-3 hydroxypropyl)phosphine (THP) and (tris(2-carboxyethyl) phosphine) (TCEP) are reducing agents frequently used in biochemistry and molecular biology applications, such as an SBS reaction. In the presence of ROS or hypochlorite, THP and TCEP may be oxidized and lose activity over time.

Figure 19:
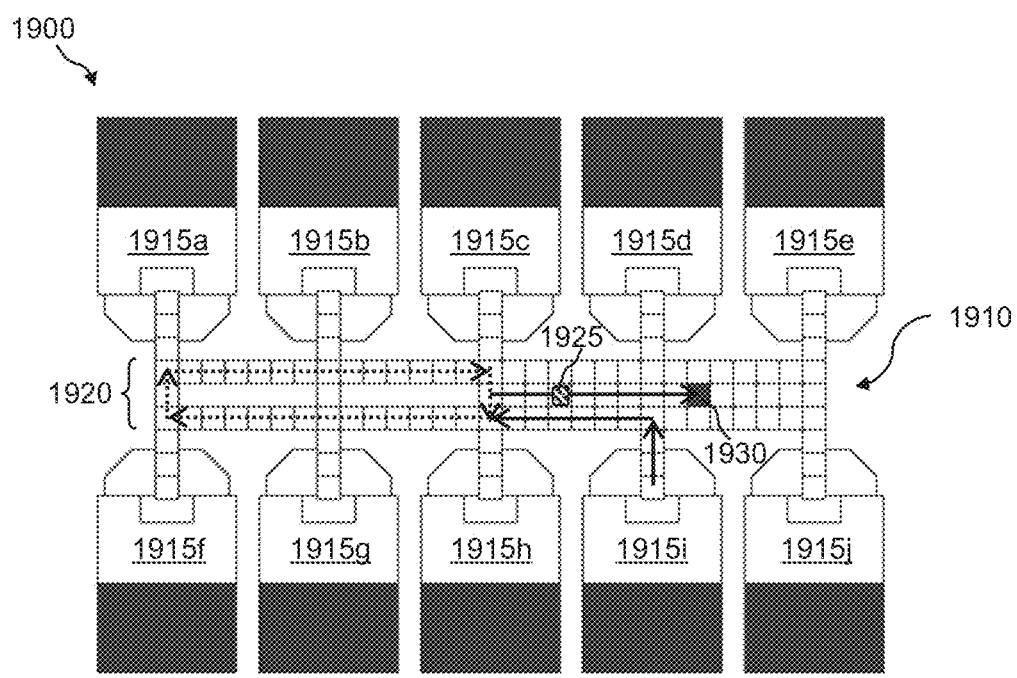
FIG. 19 is a schematic illustration of an electrode arrangement that is suitable for use in evaluating the effect of electrowetting on THP and TCEP activity over time.

FIG. 19 is a schematic plan view of an electrode arrangement 1900 that is suitable for use in evaluating the effect of electrowetting on THP and TCEP activity over time. The electrode arrangement 1900 includes various lines of electrowetting electrodes 1910 that feed various reservoir electrodes 1915a through 1915j. Droplet operations are conducted atop droplet the operations electrodes 1910 on a droplet operations surface. A looped track 1920 is formed by an arrangement of droplet operations electrodes 1910. An incubation pedestal 1925 is provided at a certain droplet operations electrode 1910 in proximity of looped track 1920. A collection port 1930 is arranged in proximity of incubation pedestal 1925.

A sample solution (not shown) may be loaded onto one of the reservoir electrodes 1915*a-j* and then dispensed. The droplet is then transported using droplet operations to the incubation pedestal 1925. Then, the droplet is incubated for a period of time and subsequently transported to collection port 1930 for manual retrieval. In another example, one or more sample droplets (not shown) may be dispensed from one or more reservoir electrodes 1915*a-j*. Then, the droplets are transported using droplet operations along looped track 1920 for a predetermined period of time prior to transporting to incubation pedestal 1925 and collection port 1930.

Figure 20A:
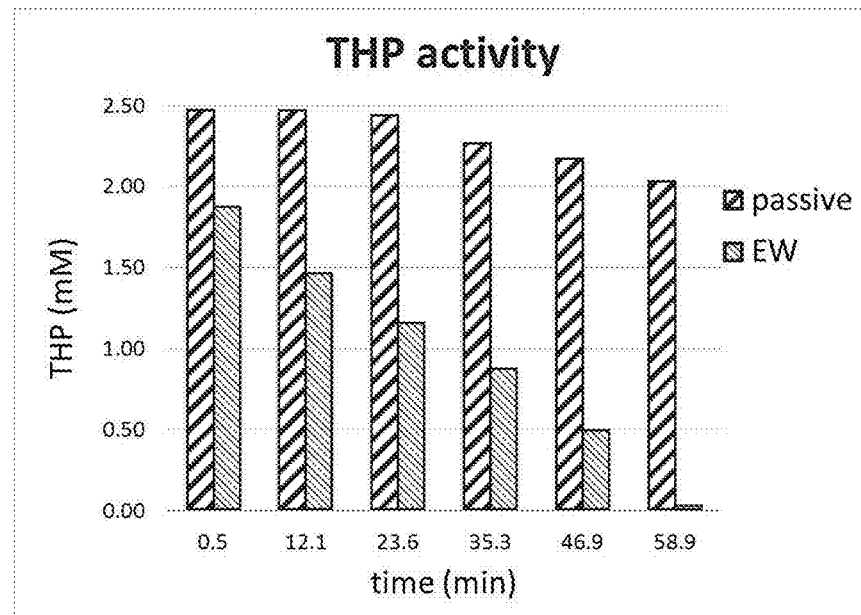
FIGS. 20A and 20B are bar graphs showing the effects of droplet electrowetting on THP activity and droplet electrowetting on TCEP activity.
Figure 20B:
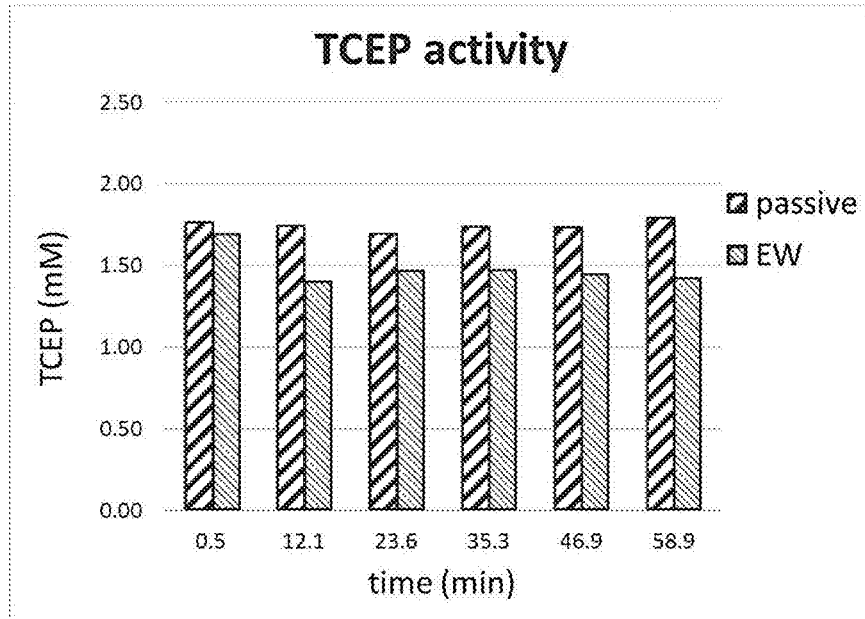

FIGS. 20A and 20B are bar graphs of the effects of droplet electrowetting on THP activity and droplet electrowetting on TCEP activity. Two different incubation conditions were used (1) "passive" where the sample solution was exposed to filler fluid on a droplet actuator reservoir but did not undergo active electrowetting and (2) "EW" where the sample solution was exposed to active electrowetting. The THP or TCEP sample solution was loaded onto a droplet actuator that includes electrode arrangement 1900 of FIG. 19. The electrowetting parameters were 300 V, 58° C. (oil), 400 second droplet transport rate, and 30 Hz switching frequency. In one example, the sample solution was loaded onto reservoir electrode 1915*i* of electrode arrangement 1900. Individual sample droplets, e.g., 6 sample droplets (8 µL (1 droplet unit)) were dispensed from reservoir electrode 1915*i* and transported using droplet operations to looped track 1920. A first sample droplet was immediately transported to incubation pedestal 1925 and incubated for 10 seconds prior to transport to collection port 1930 for manual retrieval. The remaining 5 sample droplets were transported along looped track 1920 for about 10 minutes. After about 10 minutes of active transport, a second sample droplet was transported from looped track 1920 to incubation pedestal 1925 and incubated for 10 seconds prior to transport to collection port 1930 for manual retrieval. The process was repeated until all the sample droplets were collected. A "passive" sample droplet was manually retrieved from reservoir electrode 1915*i* at the appropriate time point. The retrieved sample droplets (i.e., EW and passive sample droplets) were stored on ice until all sample droplets were collected for assay. THP or TCEP activity in the recovered sample droplets was determined using the colorimetric assay described above with reference to FIG. 12.

In the bar graphs shown in FIGS. 20A and 20B, the first bar at each time point represents the passive sample and the second bar represents the active electrowetting sample (EW). Referring now to FIG. 20A, the data show that in the absence of active electrowetting (i.e., "passive" incubation on a droplet actuator), THP activity is decreased about 15% after about 1 hour. The rate of THP activity loss is accelerated by active electrowetting (i.e., EW samples). THP activity decreases from 2.35 mM THP (i.e., the activity of the "bench" solution prior to loading on a droplet actuator) to about 1.8 mM THP in the first EW droplet collected (t=0.5 min). Referring now to FIG. 20B, the data show that the rate of TCEP activity loss is minimal over a 1 hour time course for both the passive incubation and active electrowetting (EW) samples.

Example 7. Effect of Filler Fluid on Bubble Formation, THP Oxidation, and DF Javelin 3 types of filler fluids were tested for their effects on bubble formation, THP oxidation, and DF Javelin reaction: Standard Mondrian filler fluid composed of 5 cSt PDMS with 0.0025% Span 85 (StdOil); 5 cSt PDMS with 0.05% CMS-222; and Triple blend (2% FMS-141, 10% SIB1816.0, 0.1% CMS-222 in 5 cSt PDMS). THP activity, bubble impact and DF Javelin products were quantified.

Figure 22:
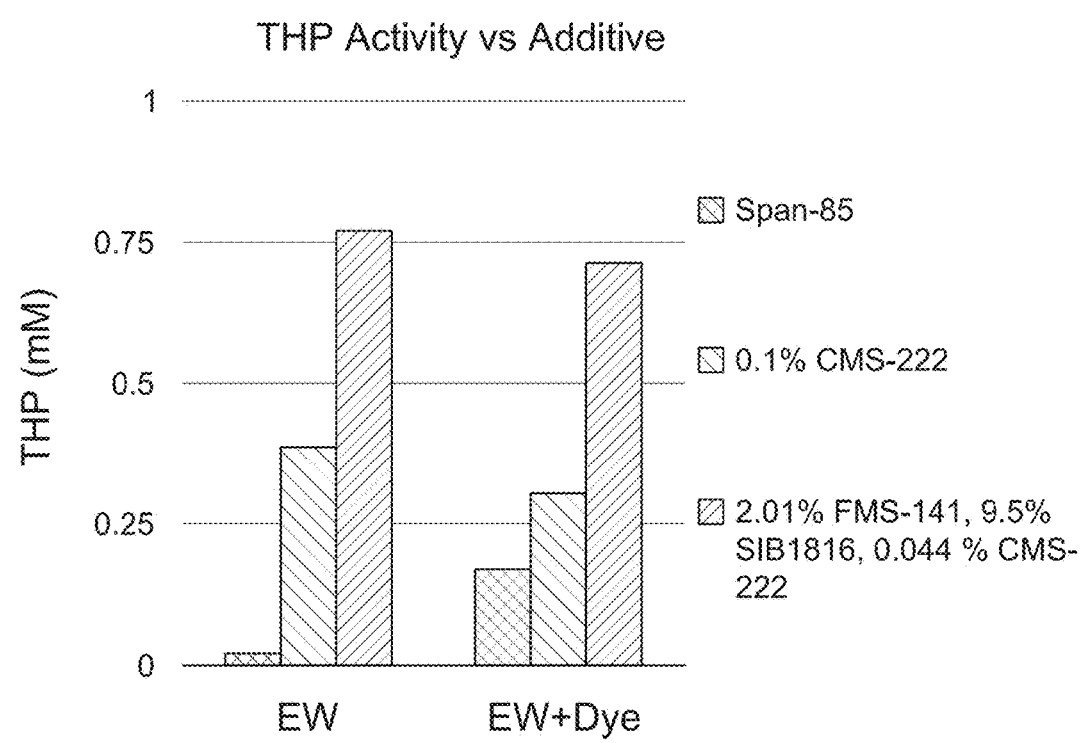
FIG. 22 is a bar graph showing the effects of CMS-222 and FMS-141 on THP activity during electrowetting.

FIG. 22 shows result on THP activity vs oil additive. A mild THP protective effect was observed with 0.01% dye with standard Mondrian filler fluid (5 cSt PDMS with 0.025% Span-85). Substituting Span-85 with 0.1% CMS-222 or a triple blend formulation decreased bubble generation and THP oxidation.

The triple blend formulation of 2% FMS-141, 10% SIB1816.0, 0.1% CMS-222 in 5 cSt PDMS decreased bubble generation during electrowetting.

Figure 23:
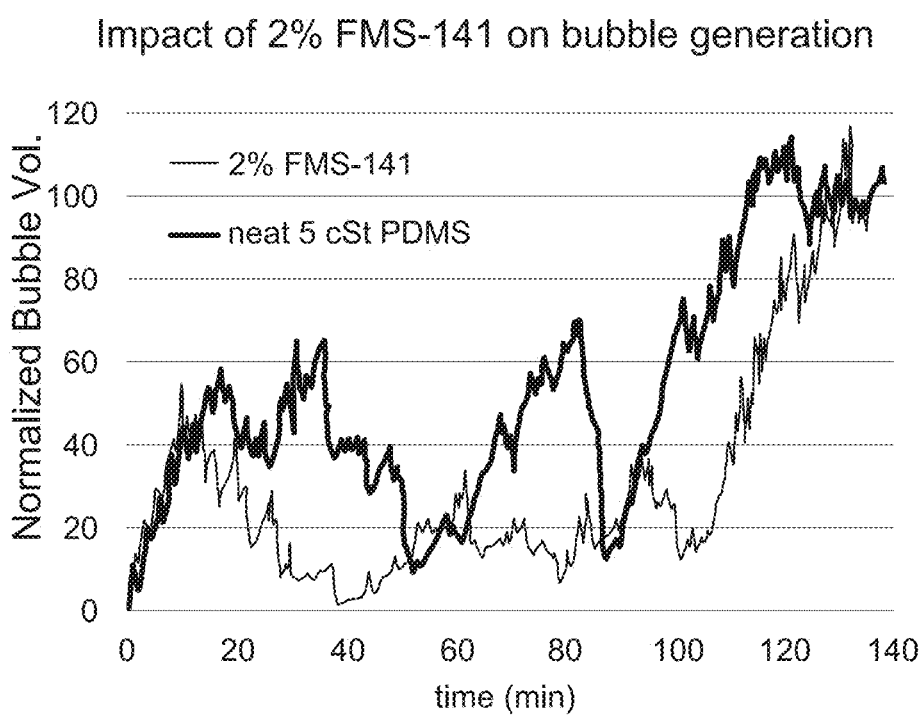
FIG. 23 is a graph showing the impact of 2% FMS-141 on bubble generation.

FIG. 23 shows bubble volume generated vs oil additive. Substituting neat 5 cSt PDMS with 2% FMS-141, 10% SIB1816.0 and 0.1% CMS-222 (Triple blend) decreased bubble generation for up to 120 min.

Figure 24A:
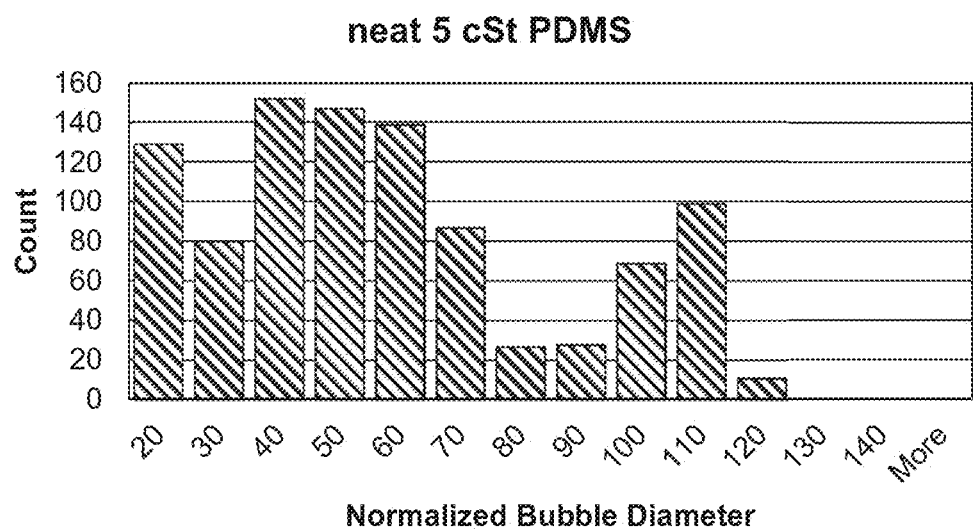
FIGS. 24A and 24B are bar graphs showing reduced bubble generation and bubble size during electrowetting in (A) 5 cSt PDMS filler fluid; and (B) 5 cSt PDMS filler fluid with 2.01% FMS-141, 9.5% SIB1816, and 0.0442% CMS-222 (Triple Blend)
Figure 24B:
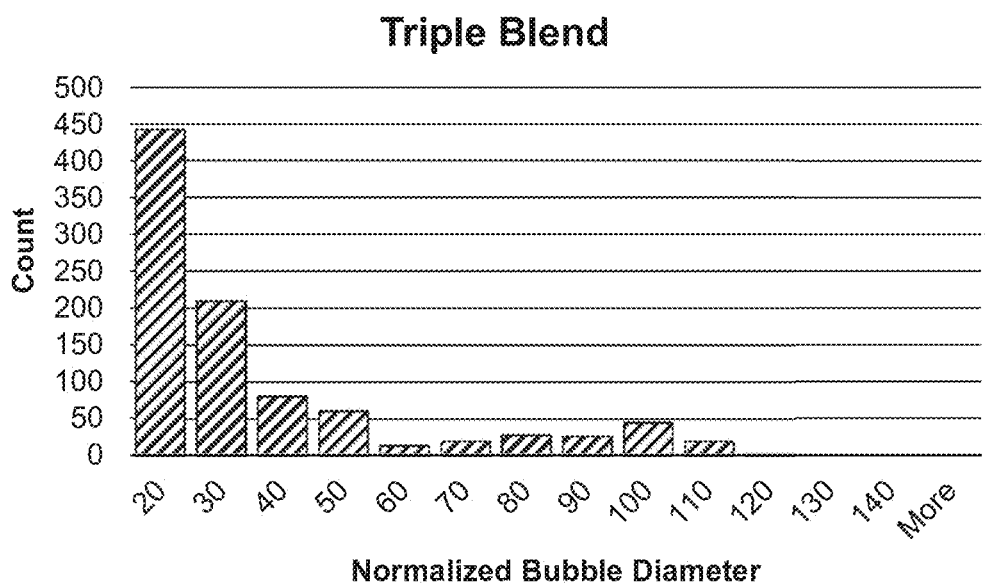

FIGS. 24A and 24B show 2% FMS-141 measurably reduced bubble generation and bubble size during electrowetting.

Figure 25A:
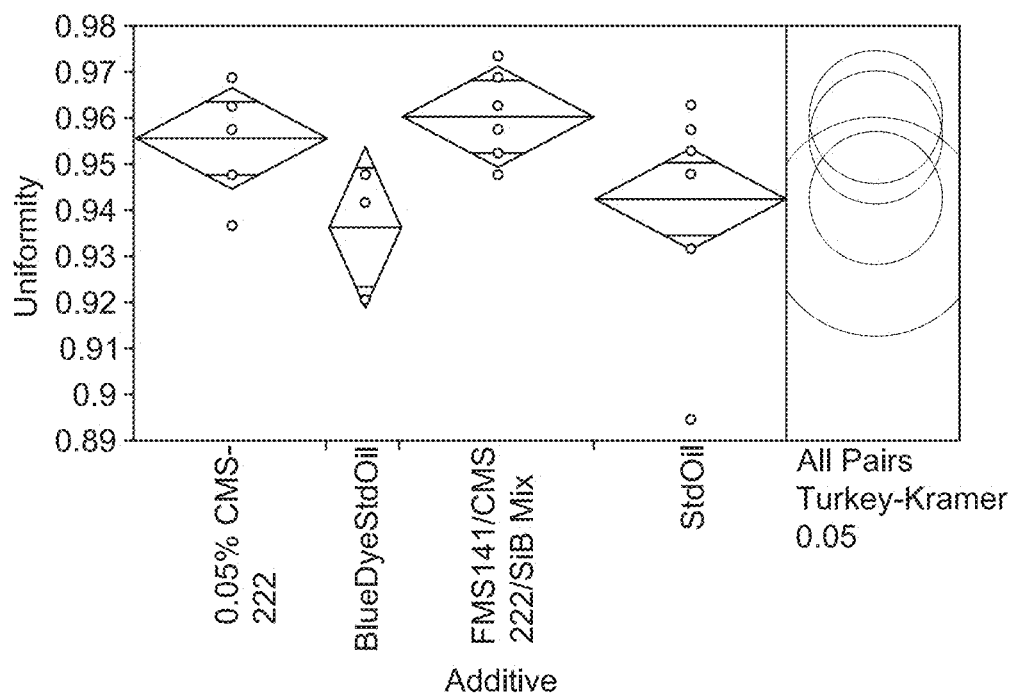
FIGS. 25A and 25B are graphs showing the effects on (A) uniformity; and (B) uniformity CV during sequencing experiments conducted in filler fluids with the following additives: 0.05% CMS-222; 0.01% Euroglaucine in the aqueous solution (BlueDyeStdOil); FMS141/CMS222/SIB Mix (a triple blend formulation composed of 2% FMS-141, 0.1% CMS-222 and 10% SIB in 5 cSt PDMS); and Mondrian filler fluid (StdOil)
Figure 25B:
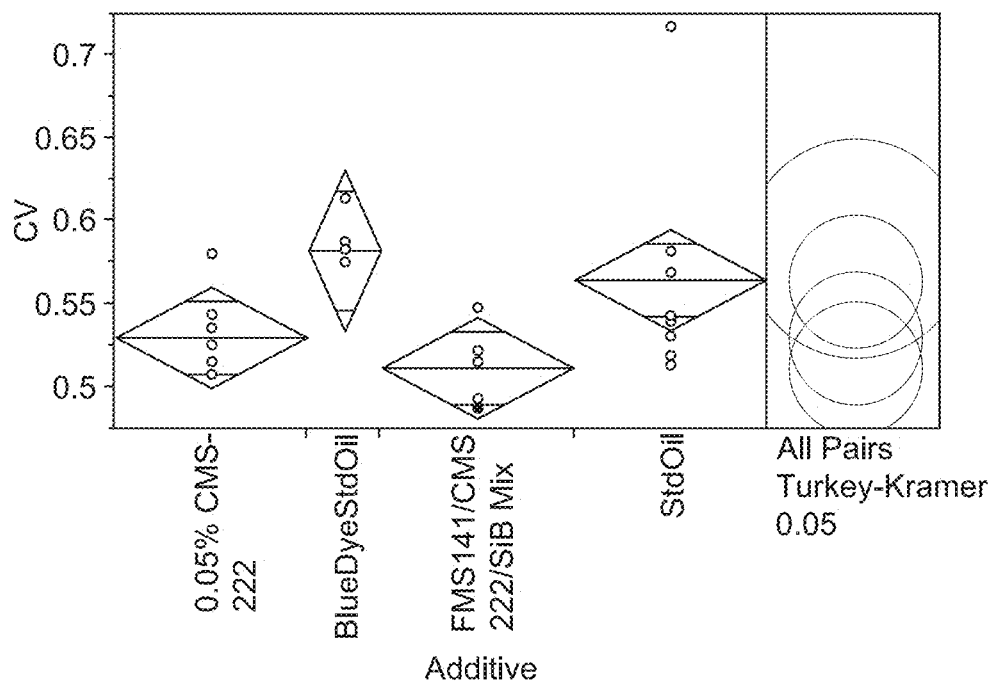

FIGS. 25A and 25B show there were significant differences between the (A) uniformity results and (B) uniformity CV results for the three experiments carried out with the following additives: 0.05% CMS-222, 0.01% Euroglaucine in the aqueous solution (BlueDyeStdOil), FMS141/CMS222/SIB Mix (a triple blend formulation composed of 2% FMS-141, 0.1% CMS-222 and 10% SIB in 5 cSt PDMS) and Mondrian filler fluid (StdOil). The Uniformity CV had the lowest amount of bubble formation for the triple blend formulation.

Example 8. Effect of CYTOP Thickness on Bubble Formation, THP Oxidation, and DF Javelin Fluidics cartridges with top plates and PCB coated with CYTOP with different thickness were tested for their effects on bubble formation, THP oxidation, and DF Javelin reaction.

3×CYTOP thickness significantly reduced bubble formation in comparison to regular CYTOP thickness (~650 nm). Cartridges were coated (top plate and PCB) with Cytop at regular thickness (~650 nm) or approximately 3× thickness Cytop. Electrowetted 2 mM MgCl2, 25 mM KCl and 80 mM TMAC for 58 minutes at 120 V, 90° C., 1 sec transport rate. Bubbles were observed in some lanes of the 1× Cytop control cartridge as early as 1 min and in all 16 lanes after 13 min. Bubbles were observed in the 3× Cytop coated cartridge in only 2 of 16 lanes after 33 minutes.

Example 9. Effect of Temperature and Immiscible Fluid Additives on Bubble Formation, THP Oxidation An Oracle cartridge was tested at 12 DU, RT, 60° C. or 80° C., 30 Hz switching frequency, 5 sec transport rate, 300 V, 30 cycles (1 h), linear slug travel. THP solution composition: 2 mM THP, 0.2 mM Ascorbate, 5 mM Tris-HCl pH 7.5, 1 M NaCl, 0.5 mM EDTA, 0.01% Tween-20. THP loss was measured sequentially with Ellman's reagent post electrowetting.

Figure 26:
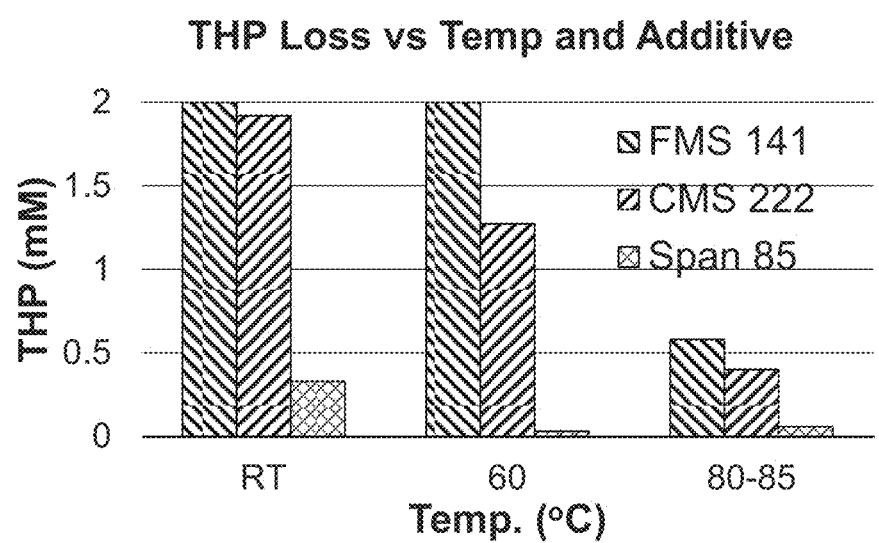
FIG. 26 shows impact of temperature and filler fluid additives on THP activity.

FIG. 26 shows THP loss due to electrowetting was reduced by substituting Span 85 with either 1% FMS 141 or 0.1% CMS 222 including under bubble generation temperatures (80-85° C.). Electrowetting 2 mM THP solution from (A) at 80-85° C. with degassed commercial filler fluid (5 cSt PMDS) led to bubble generation at 10 min. Substituting Span 85 with 0.1% CMS-222 inhibited bubble generation at 10 min.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

All publications, including patent documents and scientific articles, referred to in this application and the bibliography and attachments are incorporated by reference for the referenced materials and in their entireties for all purposes to the same extent as if each individual publication were individually incorporated by reference.

Citation of the above publications or documents is not intended as an admission that any of the foregoing is pertinent prior art, nor does it constitute any admission as to the contents or date of these publications or documents.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

Terms and phrases used in this document, and embodiments thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless apparent from the context or expressly stated otherwise. Similarly, a group of items linked with the conjunction "or" should not be read as requiring mutual exclusivity among that group, but rather should also be read as "and/or" unless it is apparent from the context or expressly stated otherwise. Furthermore, although items, elements or components of the invention may be described or claimed in the singular, the plural is contemplated to be within the scope thereof unless limitation to the singular is explicitly stated. For example, "at least one" may refer to a single or plural and is not limited to either. The presence of broadening words and phrases such as "one or more," "at least," "but not limited to", or other like phrases in some instances shall not be read to mean that the narrower case is intended or required in instances where such broadening phrases may be absent.

What is claimed is:

1. A method of reducing reactive molecular species in a reaction carried out in a digital fluidics device having one or more electrodes, the method comprising:
   providing a reaction mixture comprising one or more reagents and an electron acceptor additive;
   forming a reaction droplet from the reaction mixture; and
   activating the one or more electrodes to conduct a reaction, wherein the presence of the electron acceptor additive reduces the presence of reactive molecular species in the reaction mixture, wherein the reduction in the formation of reactive molecular species reduces the formation of bubbles.

2. The method of claim 1, wherein the electron acceptor additive comprises a redox potential lower than 830 mV.

3. The method of claim 1, wherein the electron acceptor additive comprises phenazine ethosulfate (PES), phenazine methosulfate (PMS), or a combination thereof.

4. The method of claim 1, wherein the electron acceptor additive prevents the electrolysis of water.

5. The method of claim 1, wherein the electron acceptor additive is not a reactant in the reaction.

6. The method of claim 1, wherein the electron acceptor additive does not form a gas when reduced.

7. The method of claim 1, wherein the reaction mixture comprises low conductivity in a range of about 2.5±0.2 µS/cm to about 5±0.8 µS/cm.

8. The method of claim 1, wherein the reaction mixture comprises low pH of about pH 2.0 to pH 7.0.

9. The method of claim 1, wherein activating the one or more electrodes comprises selecting droplet electrowetting parameters that result in a reduction in the formation of reactive molecular species.

10. The method of claim 9, wherein the droplet electrowetting parameters comprise one or more of droplet size, transport rate, and electrode exposure.

11. The method of claim 10, wherein droplet size is less than 8 digital units.

12. The method of claim 1, wherein the reaction is a sequencing-by-synthesis (SBS) reaction.

13. The method of claim 1, wherein the reaction is a nucleic acid amplification reaction.

14. The method of claim 1, wherein the reactive molecular species comprise reactive oxygen species (ROS) or hypochlorite.

15. The method of claim 1, further comprising surrounding the reaction droplet with an immiscible fluid.

16. The method of claim 15, wherein the immiscible fluid comprises a modified polysiloxane polymer.

17. A method of reducing reactive molecular species in a reaction carried out in a digital fluidics device having one or more electrodes, the method comprising:
providing a reaction droplet;
surrounding the reaction droplet with an immiscible fluid comprising a modified polysiloxane polymer; and
activating the one or more electrodes to conduct a reaction, wherein the presence of the polysiloxane polymer reduces the presence of reactive molecular species in the reaction droplet, wherein the reduction in the formation of reactive molecular species reduces the formation of bubbles.

18. The method of claim 17, wherein the modified polysiloxane polymer has the following formula:

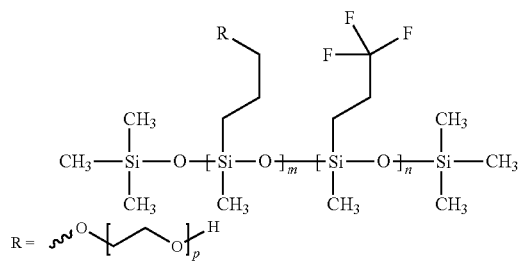

wherein m=1-300, n=1-300, and p=1-50.

19. The method of claim 18, wherein the modified polysiloxane polymer comprises POLY(3,3,3-TRIFLUOROPROPYLMETHYLSILOXANE), HYDROXYPROPYLENEOXYPROPYL)METHYLSILOXANE-DIMETHYLSILOXANE COPOLYMER, 1,3-BIS(TRIDECAFLUORO-1,1,2,2-TETRAHYDROOCTYL)TETRAMETHYLDISILOXANE, or a combination thereof.

20. The method of claim 17, wherein the modified polysiloxane polymer has the following formula:

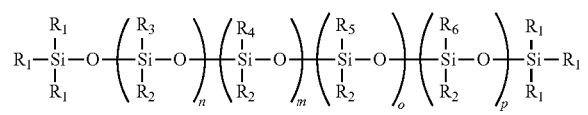

wherein each $R_1$ is, independently, hydrogen, $C_{1-8}$ alkyl, $C_{6-30}$ aryl, or $C_{1-15}$ alkyl-substituted $C_{6-30}$ aryl;
$R_2$ is, independently, $R_1$, $R_3$, $R_4$, $R_5$, or $R_6$;
$R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination;
$R_4$ is, independently, a polyalkylene glycol moiety, where the alkylene groups are, independently, $C_{2-4}$, and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof;

$R_5$ is, independently, a dye selected from the group consisting of erioglaucine, Nile blue, methylene blue, methyl viologen, methyl brilliant green, popop brilliant green, caffeine dye, proton sponge dye, and DDT black, linked to the polymer at any position;
$R_6$ is an electron acceptor;
m is a whole number from 0 to about 300,
n is a whole number from 0 to about 300,
o is a whole number from 0 to about 300, and
p is a whole number from 0 to about 300,
wherein at least one of m, n, o, and p is not 0.

21. The system of claim 20, wherein each $R_1$ is independently hydrogen, methyl, ethyl, propyl, isopropyl, butyl, sec-butyl, t-butyl, isobutyl, isoamyl, or t-amyl.

22. A system for conducting a reaction in the presence of an activated electrode while reducing the formation of reactive molecular species, wherein the reduction in the formation of reactive molecular species reduces the formation of bubbles, the system comprising:
a fluidics cartridge comprising an electrowetting array having a plurality of electrodes, wherein the fluidics cartridge comprises a substrate having a hydrophobic coating having a thickness of greater than about 1,000 nm.

23. The system of claim 22, further comprising an immiscible fluid, wherein the immiscible fluid comprises a modified polysiloxane polymer.

24. The system of claim 23, wherein the modified polysiloxane polymer has the following formula:

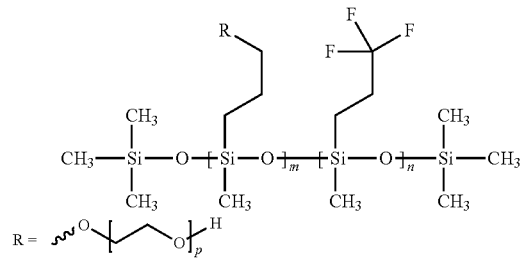

wherein m=1-300, n=1-300, and p=1-50.

25. The system of claim 23, wherein the modified polysiloxane polymer comprises POLY(3,3,3-TRIFLUOROPROPYLMETHYLSILOXANE), HYDROXYPROPYLENEOXYPROPYL)METHYLSILOXANE-DIMETHYLSILOXANE COPOLYMER, 1,3-BIS(TRIDECAFLUORO-1,1,2,2-TETRAHYDROOCTYL)TETRAMETHYLDISILOXANE, or a combination thereof.

26. The system of claim 23, wherein the modified polysiloxane polymer has the following formula:

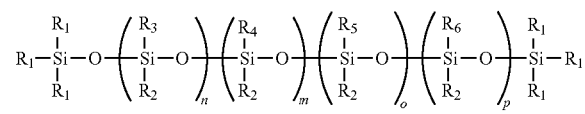

wherein each $R_1$ is, independently, hydrogen, $C_{1-8}$ alkyl, $C_{6-30}$ aryl, or $C_{1-15}$ alkyl-substituted $C_{6-30}$ aryl;
$R_2$ is, independently, $R_1$, $R_3$, $R_4$, $R_5$, or $R_6$;
$R_3$ is, independently, a $C_{1-10}$ fluoroalkyl or $C_{1-15}$ fluoroalkyl-substituted $C_{6-30}$ aryl, where fluoroalkyl is defined as having anywhere from 1 fluorine atom to complete fluorination;

$R_4$ is, independently, a polyalkylene glycol moiety, where the alkylene groups are, independently, $C_{2-4}$, and the number of repeat units in the moiety is between 1 and 1000, more typically, between 1 and 150, and still more typically, between 1 and 50 repeat units, wherein specific polyalkylene glycol moieties include polyethylene glycol, polypropylene glycol, and copolymers thereof;

$R_5$ is, independently, a dye selected from the group consisting of erioglaucine, Nile blue, methylene blue, methyl viologen, methyl brilliant green, popop brilliant green, caffeine dye, proton sponge dye, and DDT black, linked to the polymer at any position;

$R_6$ is an electron acceptor;

m is a whole number from 0 to about 300, n is a whole number from 0 to about 300, o is a whole number from 0 to about 300, and p is a whole number from 0 to about 300, wherein at least one of m, n, o, and p is not 0.

27. The system of claim 26, wherein each $R_1$ is independently hydrogen, methyl, ethyl, propyl, isopropyl, butyl, sec-butyl, t-butyl, isobutyl, isoamyl, or t-amyl.

* * * * *

UNITED STATES PATENT AND TRADEMARK OFFICE
CERTIFICATE OF CORRECTION

PATENT NO. : 10,309,927 B2
APPLICATION NO. : 15/093529
DATED : June 4, 2019
INVENTOR(S) : Rigo Pantoja et al.

It is certified that error appears in the above-identified patent and that said Letters Patent is hereby corrected as shown below:

In the Claims

In Column 66, Line 12, in Claim 21, delete "system" and insert -- method --, therefor.

Signed and Sealed this
Seventeenth Day of September, 2019

Andrei Iancu
*Director of the United States Patent and Trademark Office*